(12) United States Patent
Romine et al.

(10) Patent No.: US 7,183,302 B2
(45) Date of Patent: Feb. 27, 2007

(54) IMINOTHIAZOLIDINONES AS INHIBITORS OF HCV REPLICATION

(75) Inventors: Jeffrey Lee Romine, Meriden, CT (US); Scott W. Martin, Middletown, CT (US); Lawrence B. Snyder, Clinton, CT (US); Michael Serrano-Wu, Guilford, CT (US); Milind Deshpande, Madison, CT (US); Darren Whitehouse, Westbrook, CT (US); Julie Lemm, Durham, CT (US); Donald O'Boyle, Clinton, CT (US); Min Gao, Madison, CT (US); Richard Colonno, Farmington, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 210 days.

(21) Appl. No.: 10/637,099

(22) Filed: Aug. 8, 2003

(65) Prior Publication Data

US 2005/0096364 A1    May 5, 2005

Related U.S. Application Data

(60) Provisional application No. 60/403,694, filed on Aug. 15, 2002, provisional application No. 60/402,661, filed on Aug. 12, 2002.

(51) Int. Cl.
*A61K 43/78* (2006.01)
*C07D 277/18* (2006.01)

(52) U.S. Cl. .................. 514/369; 514/236.8; 514/277; 514/370; 514/422; 544/159; 544/166; 546/270.7; 548/185; 548/524

(58) Field of Classification Search ................ 514/369, 514/236.8, 277, 370, 422; 544/159, 166; 546/270.7; 548/185, 524
See application file for complete search history.

(56) References Cited

U.S. PATENT DOCUMENTS

| 6,030,785 A | 2/2000 | Katze et al. |
| 6,323,180 B1 | 11/2001 | Llinas-Brunet et al. |
| 2005/0069522 A1* | 3/2005 | Colonno et al. ........... 424/85.7 |

FOREIGN PATENT DOCUMENTS

WO   WO2001-JP9790   * 10/2001   ............. 514/230.5

OTHER PUBLICATIONS

Lauer et al. (2001) New England Journal of Medicine, vol. 345, No. 1, pp. 41-52.
Poynard et al. (1998) The Lancet, vol. 352, pp. 1426-1432.
Zeuzem et al. (2000) The New England Journal of Medicine, vol. 343, No. 23, pp. 1666-1672.
De Clercq. (2001) Journal of Clinical Virology, vol. 22, pp. 73-89.
Tan et al. (2001) Virology, vol. 284, pp. 1-12.
Park et al. (2003) The Journal of Biological Chemistry, vol. 278, No. 33, pp. 30711-30718.
Sarrazin, C. et al., "Mutations in the Protein Kinase-Binding Domain of the NS5A Protein in Patients Infected with Hepatitis C Virus Type 1a Are Associated with Treatment Response," The Journal of Infectious Diseases, vol. 181, pp. 432-441 (2000).
Frangeul, L. et al., "Mutations in NS5A Region of Hepatitis C Virus Genome Correlate With Presence of NS5A Anitbodies and Response to Interferon Therapy for Most Common European Hepatitis C Virus Genotypes," Hepatology, vol. 28, No. 6, pp. 1674-1679 (1998).
Woitas, R.P. et al., "Differential expansion of T-cell receptor variable beta subsets after antigenice stimulation in patients with different outcomes of hepatitis C infection," Immunology, vol. 106, pp. 419-427 (2002).
Wang, Y.S. et al., "Structural and biological characterization of pegylated recombinant interferon alpha-2b and its therapeutic implications," Advanced Drug Delivery Reviews, vol. 54, pp. 547-570 (2002).

* cited by examiner

*Primary Examiner*—Kamal A. Saeed
*Assistant Examiner*—Yong Chu
(74) *Attorney, Agent, or Firm*—Pamela A. Mingo

(57) ABSTRACT

Compounds having the structure of formula I are described

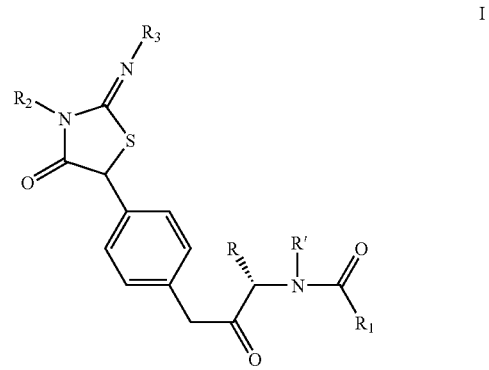

wherein R, R', $R_1$, $R_2$, and $R_3$ are as defined in the specification. The compounds can inhibit hepatitis C virus (HCV) replication, and in particular the function of the HCV NS5A protein.

19 Claims, No Drawings

IMINOTHIAZOLIDINONES AS INHIBITORS OF HCV REPLICATION

CROSS REFERENCE TO RELATED APPLICATIONS

This application claims priority from U.S. provisional application U.S. Ser. No. 60/402,661 filed Aug. 12, 2002 and U.S. provisional application U.S. Ser. No. 60/403,694 filed Aug. 15, 2002.

FIELD OF THE INVENTION

The present invention is generally directed to antiviral compounds, and more specifically directed to compounds which can inhibit the function of the NS5A protein encoded by Hepatitis C virus (HCV), compositions comprising such compounds and methods for inhibiting the function of the NS5A protein.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. N. Engl. J. Med. (2001), 345, 41–52).

Presently, the most effective HCV therapy employs a combination of alpha-interferon and ribavirin, leading to sustained efficacy in 40% of patients. (Poynard, T. et al. Lancet (1998), 352, 1426–1432). Recent clinical results demonstrate that pegylated alpha-interferon is superior to unmodified alpha-interferon as monotherapy (Zeuzem, S. et al. N. Engl. J. Med. (2000), 343, 1666–1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Among the compounds that have demonstrated efficacy in inhibiting HCV replication, as selective HCV serine protease inhibitors, are the peptide compounds disclosed in U.S. Pat. No. 6,323,180. NS5B polymerase inhibitors have also demonstrated activity. However, none of these compounds have, to date, progressed beyond clinical trials (De Clercq, E. J. Clin. Virol. 2001 22 73–89).

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L.,; Katzel, M. G. Virology (2001) 284, 1–12, and in Park, K.-J.; Choi, S.-H, J. Biological Chemistry (2003).

SUMMARY OF THE INVENTION

The present invention relates to compounds compound of formula I

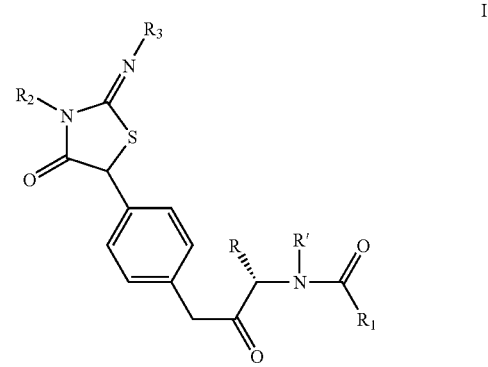

wherein R is $C_{1-4}$ alkyl, optionally substituted with 1–3 halogen atoms, 1–3 oxygen atoms or 1–3 nitrogen atoms, said R having an S stereoconfiguration; R' is H or a bond wherein R and R' are joined to form a cyclic structure;

$R_1$ is a member selected from the group consisting of $C_{1-6}$ alkyl, $C_{3-7}$ cycloalkyl, $C_{6-10}$ aryl, $C_{1-6}$ alkoxy, $C_{6-10}$ aryloxy, $C_{6-10}$ aryl ($C_{1-6}$) alkyl, $C_{6-10}$ aryl ($C_{1-6}$) alkoxy, aryl-substituted $C_{1-6}$ alkyl ($C_{6-10}$) aryl and Het; and $R_2$ and $R_3$ are each independently selected from the group consisting of $C_{1-6}$ alkyl, $C_{3-7}$ cycloalkyl, $C_{6-10}$ aryl, $C_{1-6}$ alkoxy, $C_{6-10}$ aryloxy, Het, $C_{6-10}$ aryl ($C_{1-6}$) alkyl, $C_{6-10}$ aryl ($C_{1-6}$) alkoxy, acyl ($C_{1-6}$) alkoxy, with the proviso that one of $R_2$ or $R_3$ can be a bond wherein $R_2$ and $R_3$ are joined to form a cyclic structure;

or pharmaceutically acceptable enantiomer, diastereomer, solvate, prodrug or salt thereof.

The present invention also provides compositions comprising the compounds of the invention or pharmaceutically acceptable enantiomers, diastereomers, salts, solvates or prodrugs thereof and a pharmaceutically acceptable carrier. In particular, the present invention provides pharmaceutical compositions useful for inhibiting the function of the HCV N5A protein comprising a compound of the present invention, or a pharmaceutically acceptable enantiomer, diastereomer, salt, solvate or prodrug thereof, and a pharmaceutically acceptable carrier.

The present invention further provides methods for treating patients infected with HCV, comprising administering to the patient a therapeutically effective amount of a compound of the present invention, or a pharmaceutically acceptable enantiomer, diastereomer, salt, solvate or prodrug thereof. Additionally, the present invention provides methods of inhibiting the function of HCV NS5A protein by contacting the HCV NS5A protein with a compound of the present invention.

By virtue of the present invention, it is now possible to provide improved drugs comprising the compounds of the invention which can be effective in the treatment of patients infected with HCV. Specifically, the present invention provides compounds that can inhibit the function of the NS5A protein. Further, the present invention makes it possible to administer combination therapy to a patient whereby a compound in accordance with the present invention, which is effective to inhibit the HCV NS5A protein, can be administered with another compound having anti-HCV activity, e.g., a compound which is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

The compounds of the present invention can inhibit the RNA replication in a cell culture system (replicon), preferably with a therapeutic index (TI, $CC_{50}/EC_{50}$) approaching or exceeding 100-fold. They have been found to be specific inhibitors of HCV replication and inactive against other viruses (HRV, RSV, HIV, Flu, BVDV) and the BVDV replicon. HCV replicon mutants conferring resistance were selected and resistant cell lines indicate that NS5A is the major target of the compounds of the present invention.

DETAILED DESCRIPTION OF THE INVENTION

The compounds of the present invention provide therapeutic agents which inhibit hepatitis C virus (HCV) replication, and can provide a safe and effective treatment for HCV infection. Iminothiazolidones are described which inhibit RNA replication in a cell culture system (replicon) with a therapeutic index (TI $CC_{50}/EC_{50}$) of greater than 100-fold. A clear structure-activity relationship was observed resulting in low nanomolar potency for compounds evaluated in the replicon system. Typically, the compounds of the present invention exhibit $EC_{50}$ values of <5 micromolar ("µM").

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture. With reference to the instances where (R) or (S) is used, it is to designate the absolute configuration of a substituent in context to the whole compound and not in context to the substituent alone.

Unless otherwise specifically noted herein, the terms set forth below will have the following definitions.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445. The compounds of the present invention are useful in the form of the free base or acid or in the form of a pharmaceutically acceptable salt thereof. All forms are within the scope of the invention.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of formula I, and pharmaceutically acceptable enantiomer, diastereomer salts, and solvates, e.g. hydrates, and prodrugs. Similarly, references to intermediates, are meant to embrace their salts, and solvates, where the context so permits. References to the compound of the invention also include the preferred compounds, e.g. formula II and A–M.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The term "substituted" as used herein includes substitution at from one to the maximum number of possible binding sites on the core, e.p., organic radical, to which the subsitutent is bonded, e.g., mono-, di-, tri- or tetra-substituted, unless otherwise specifically stated.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine or arylalkyl, include all possible stable configurations, unless otherwise specifically stated. Certain radicals and combinations are defined below for purposes of illustration.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents having the specified number of carbon atoms and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specfically stated. This a $C_{4-10}$ alkylcycloalkyl may contain from 1–7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralalkyl" mean an aryl group substituted with one or more alkyl groups. Unless the carbon range of each group is specified, the stated range applies to the entire substituent. Thus, a $C_{7-14}$ alkylaryl group many have from 1–8 carbon atoms in the alkyl group for a monocyclic aromatic and from 1–4 carbon atoms in the alkyl group for a fused aromatic. The attachment of the group to bonding site on the molecule can be either at the aryl group or the alkyl group. Unless a specific aryl radical is specified, e.g., fluoro-phenyl, or the radical is stated to be unsubstituted, the aryl radicals include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl(alkoxy)amine. Examples of alkylaryl groups include benzyl, butylphenyl and 1-naphthylmethyl.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "alkylamide" as used herein means an amide mono-substituted with an alkyl, such as

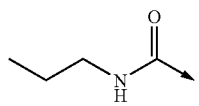

The term "heterocycle", also referred to as "Het", as used herein means 7–12 membered bicyclic heterocycles and 5–7 membered monocyclic heterocycles.

Preferred bicyclic heterocycles are 7–12 membered fused bicyclic ring systems (both rings share an adjacent pair of atoms) containing from one to four heteroatoms selected from nitrogen, oxygen and sulfur, wherein both rings of the heterocycle are fully unsaturated. The nitrogen and sulfur heteroatoms atoms may be optionally oxidized. The bicyclic heterocycle may contain the heteroatoms in one or both rings. Unless a specific heterocycle is specified, e.g., a fluorinated 7–12 membered bicyclic heterocycle, or the heterocycle is stated to be unsubstituted, the heterocycles include those substituted with typical substituents known to those skilled in the art. For example, the bicyclic heterocycle may also contain substituents on any of the ring carbon atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, $C_{1-6}$ alkylsulfoxide, di ($C_{1-6}$) alkyl (alkoxy)amine, $C_{6-10}$ aryl, $C_{7-14}$ alkylaryl, and a 5–7 membered monocyclic heterocycle. When two substituents are attached to vicinal carbon atoms of the bicyclic heterocycle, they can join to form a ring, e.g., a five, six or seven membered ring system containing up to two heteroatoms selecting from oxygen and nitrogen. The bicyclic heterocycle may be attached to the molecule, e.g. $R_1$ in formula I, at any atom in the ring and preferably carbon.

Examples of bicyclic heterocycles include, but are not limited to, the following ring systems:

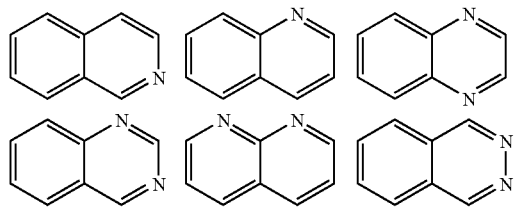

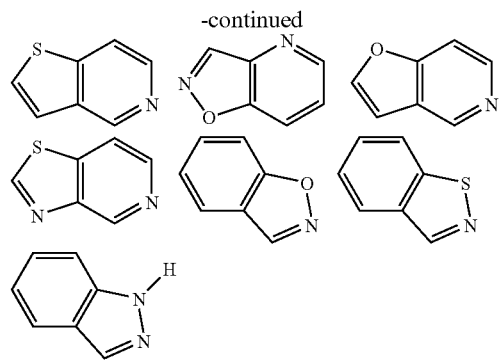

Preferred monocyclic heterocycles are 5–7 membered saturated, partially saturated or fully unsaturated ring system (this latter subset also herein referred to as unsaturated heteroaromatic) containing in the ring from one to four heteroatoms selected from nitrogen, oxygen and sulfur, wherein the sulfur and nitrogen heteroatoms may be optionally oxidized. Unless a specific heterocycle is specified, e.g., a $C_{1-6}$ alkoxy substituted 5–7 membered monocyclic heterocycle, or the heterocycle is stated to be unsubstituted, the heterocycles include those substituted with typical substituents known to those skilled in the art. For example, the monocyclic heterocycle may also contain substituents on any of the ring atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfoxide, $C_{1-6}$ alkylsulfonamide, di ($C_{1-6}$) alkyl(alkoxy)amine, $C_{6-10}$ aryl, $C_{7-14}$ alkylaryl and an additional 5–7 membered monocyclic heterocycle. The monocyclic heterocycle may be attached to the molecule, e.g. $R_1$ in formula I, at any atom in the ring.

Examples of monocyclic heterocycles include, but are not limited to, the following (and their tautomers):

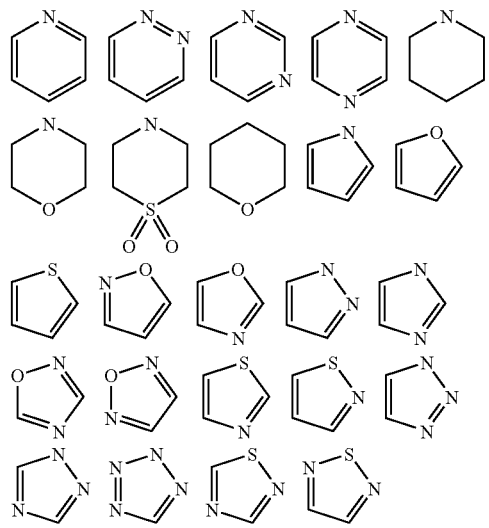

Those skilled in the art will recognize that the heterocycles used in the compounds of the present invention should be stable. Generally, stable compounds are those which can be synthesized, isolated and formulated using techniques known the those skilled in the art without degradation of the compound.

The term "substituent" with reference to an amino acid or amino acid derivative means a radical derived from the corresponding α-amino acid. For instance, the substituents methyl, iso-propyl, and phenyl represent the amino acids alanine, valine, and phenyl glycine, respectively.

Desirably, the compounds of the present invention have formula I

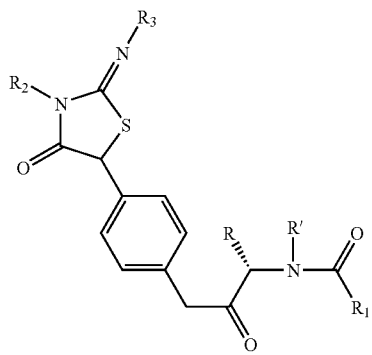

I wherein R is $C_{1-4}$ alkyl, optionally substituted with 1–3 halogen atoms, 1–3 oxygen atoms or 1–3 nitrogen atoms, said R having an S stereoconfiguration; R' is H or a bond wherein R and R' are joined to form a cyclic structure;

$R_1$ is a member selected from the group consisting of $C_{1-6}$ alkyl, $C_{3-7}$ cycloalkyl, $C_{6-10}$ aryl, $C_{1-6}$ alkoxy, $C_{6-10}$ aryloxy, $C_{6-10}$ aryl ($C_{1-6}$) alkyl, $C_{6-10}$ aryl ($C_{1-6}$) alkoxy, aryl-substituted $C_{1-6}$ alkyl ($C_{6-10}$) aryl and Het; and $R_2$ and $R_3$ are each independently selected from the group consisting of $C_{1-6}$ alkyl, $C_{3-7}$ cycloalkyl, $C_{6-10}$ aryl, $C_{1-6}$ alkoxy, $C_{6-10}$ aryloxy, Het, $C_{6-10}$ aryl ($C_{1-6}$) alkyl, $C_{6-10}$ aryl ($C_{1-6}$) alkoxy, acyl ($C_{1-6}$) alkoxy, with the proviso that one of $R_2$ or $R_3$ can be a bond wherein $R_2$ and $R_3$ are joined to form a cyclic structure;

or a pharmaceutically acceptable enantiomer, diastereomer, solvate, prodrug or salt thereof.

In one preferred aspect of the invention, R is methyl and R' is H. In another preferred aspect of the invention, R' is a bond and R is selected from propyl forming a cyclic structure with R', or propionyl forming a cyclic structure with R'.

Preferably, $R_1$ is selected from the group consisting of $C_{6-10}$ aryl ($C_{1-6}$) alkyl, $C_{6-10}$ aryl ($C_{1-6}$) alkoxy and a 5–7 membered monocylic heterocycle. More preferably, $R_1$ is selected from the group consisting of $C_6$ aryl ($C_{1-3}$) alkyl and $C_6$ aryl ($C_{1-3}$) alkoxy.

Preferably, $R_2$ and $R_3$ are each independently selected from the group consisting of $C_{6-10}$ aryl, 5–7 membered monocyclic heterocycle, $C_{1-3}$ alkyl substituted with a 5–7 membered heterocycle, $C_{6-10}$ aryl substituted with a 5–7 membered heterocycle, and a 7–12 membered bicyclic heterocycle. More preferably, $R_2$ and $R_3$ are each independently selected from a $C_{1-3}$ alkyl substituted with a 5–7 membered heterocycle and a halogenated 5–7 membered heterocycle. In another aspect of the invention, one of $R_2$ and $R_3$ is a bond and the other is a $C_{6-10}$ aryl ($C_{1-3}$) alkyl, e.g., benzyl, joined to the bond to form a cyclic structure.

In one preferred aspect of the invention, $R_1$ is selected from the group consisting of:

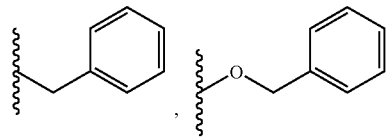

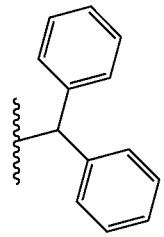

$R_2$ is selected from the group consisting of:

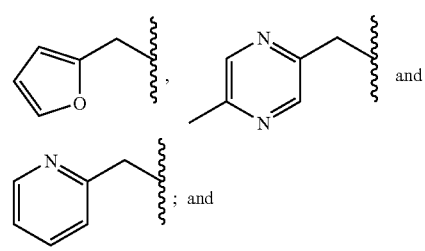

$R_3$ is selected from the group consisting of:

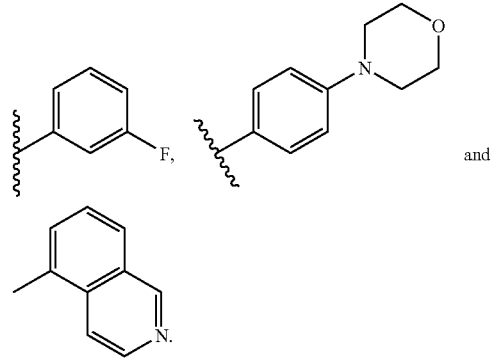

In a preferred aspect of the invention, the compounds are selected from those having the structures of formulas A to M:

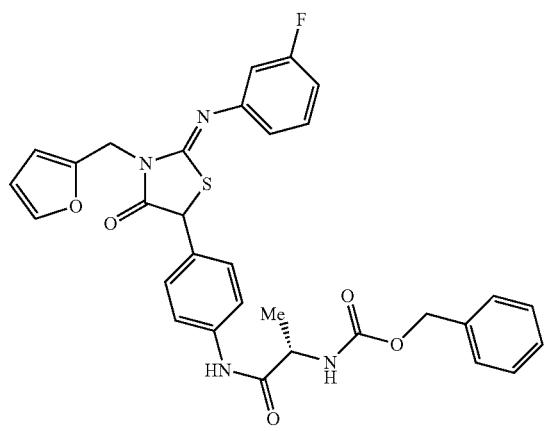

A

B
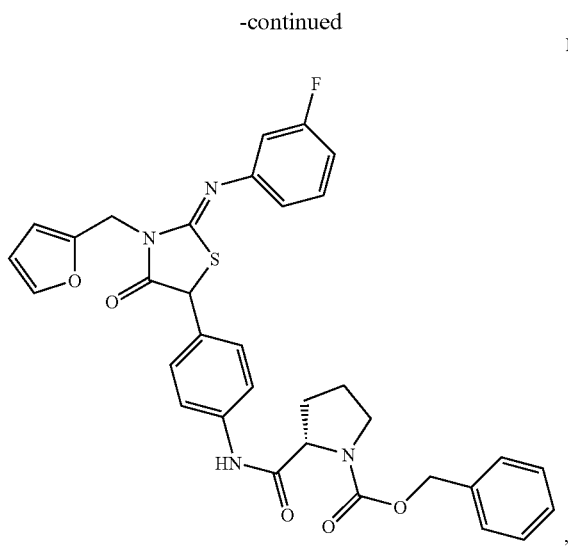
C
E
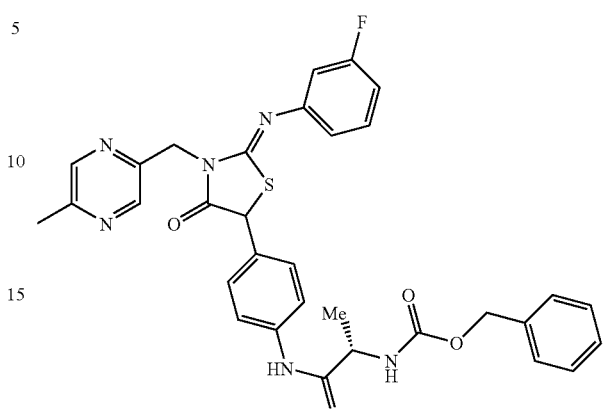
,
F
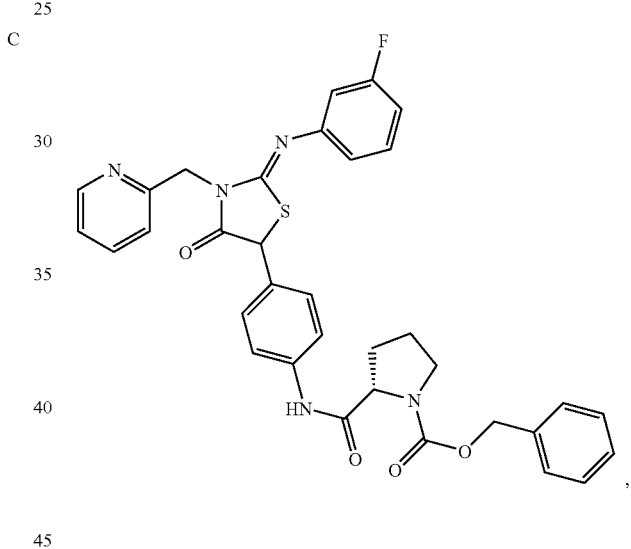
,
D
G
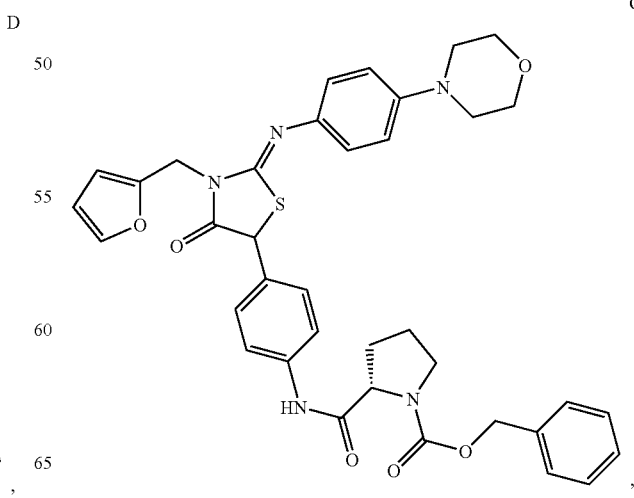
,

-continued
H
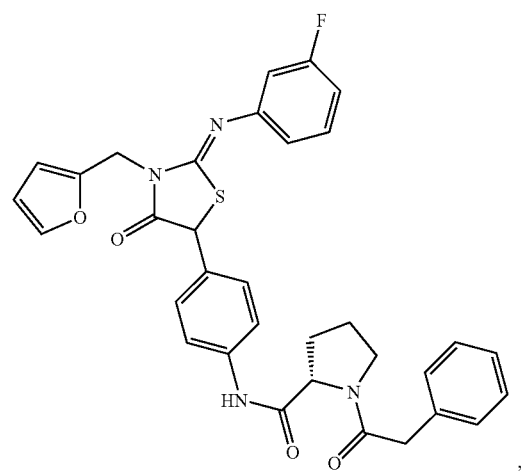,
I
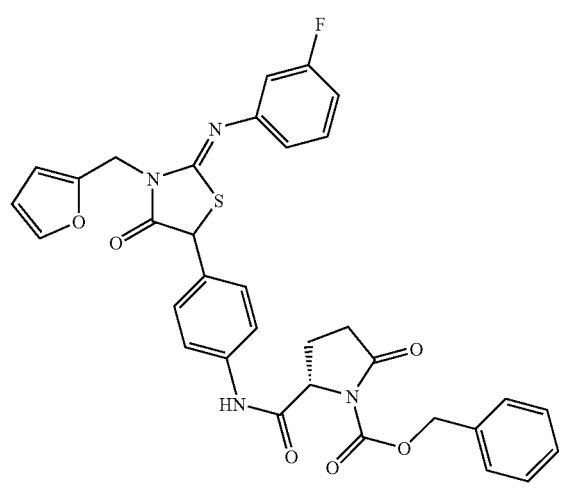,
J
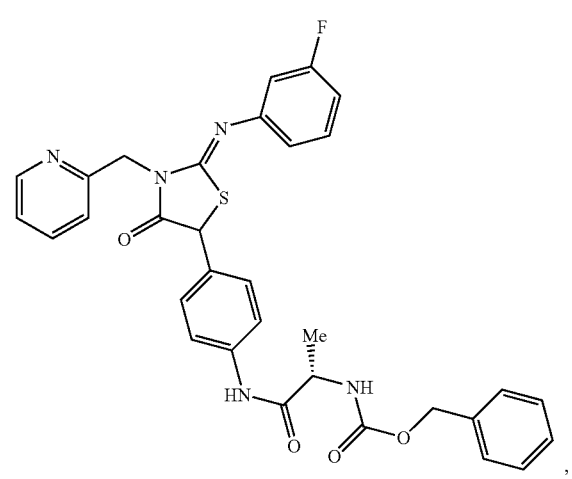,
-continued
K
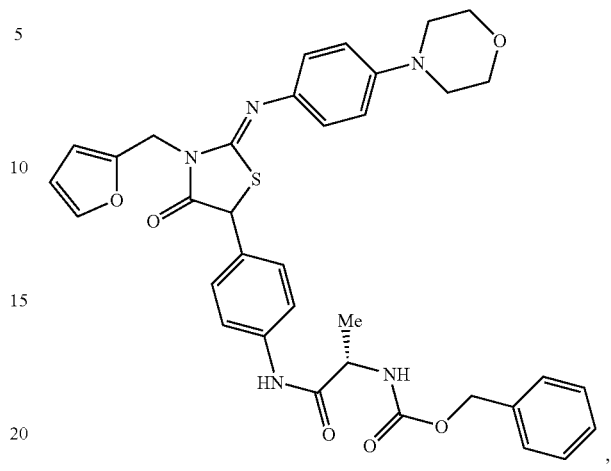,
L
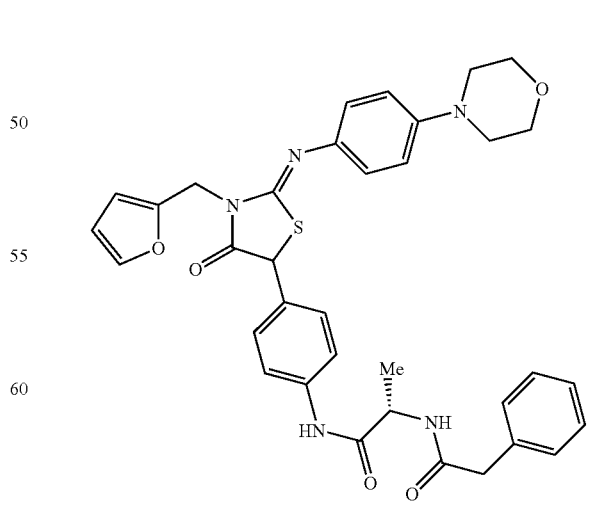 and
M
or pharmaceutically acceptable enantiomers, diastereomers, solvates, prodrugs or salts thereof.

In another preferred aspect of the invention, the compounds have the structure of formula II

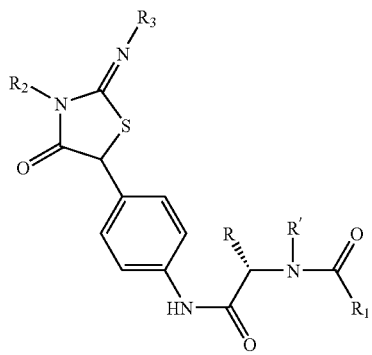

wherein R is $C_{1-4}$ alkyl, having an S stereoconfiguration; R' is H or a bond wherein R and R' are joined to form a cyclic structure;

$R_1$ is a member selected from the group consisting of $C_{6-10}$ aryl $(C_{1-6})$ alkyl, $C_{6-10}$ aryl $(C_{1-6})$ alkoxy and Het; and $R_2$ and $R_3$ are each independently selected from the group consisting of $C_{6-10}$ aryl, 5–7 membered monocyclic heterocycle, $C_{1-3}$ alkyl substituted with a 5–7 membered heterocycle, $C_{6-10}$ aryl substituted with a 5–7 membered heterocycle, and a 7–12 membered bicyclic heterocycle;

or a pharmaceutically acceptable enantiomer, diastereomer, solvate, prodrug or salt thereof.

In one preferred aspect, R is methyl and R' is H. In another preferred aspect, R' is a bond and R is propyl forming a cyclic structure with R'.

Preferably, $R_1$ is selected from the group consisting of $C_6$ aryl $(C_{1-3})$ alkyl and $C_6$ aryl $(C_{1-3})$ alkoxy. More preferably, $R_1$ is benzyl.

Preferably, $R_2$ is a 5–6 membered monocyclic heterocycle. More preferably, $R_2$ is selected from the group consisting of:

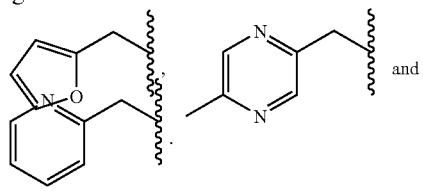

and

Preferably, $R_3$ is selected from the group consisting of a 5–6 membered monocyclic heterocycle, $C_{6-10}$ aryl substituted with a 5–7 membered heterocycle and a 7–12 membered bicyclic heterocycle. More preferably, $R_3$ is selected from the group consisting of:

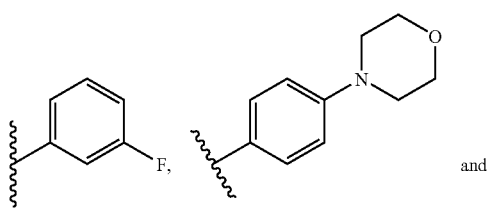

and

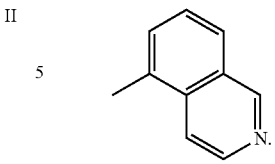

Compounds of the present invention which are substituted with a basic group, by virtue of their basic moiety, can form salts by the addition of a pharmaceutically acceptable acid. The acid addition salts are formed from a compound of formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

The present invention includes both enantiomers and mixtures of enantiomers such as racemic mixtures. All chiral, diastereomeric, racemic forms and all geometric forms of a particular structure are intended, unless the specific stereochemistry or isomer form is specifically indicated.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of the present invention may be in the form of a prodrug. Simple aliphatic or aromatic esters derived from, when present, acidic groups pendent on the compounds of this invention are preferred prodrugs. In some cases it is desirable to prepare double ester type prodrugs such as (acyloxy) alkyl esters or (alkoxycarbonyl)oxy)alkyl esters.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The present invention also provides compositions comprising a compound of the present invention, or a pharmaceutically acceptable enantiomer, diastereomer, salt, solvate or prodrug thereof, and a pharmaceutically acceptable carrier. Pharmaceutical compositions of the present invention comprise a therapeutically effective amount of a compound of the invention, or a pharmaceutically acceptable enantiomer, diastereomer, salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

Thus, in one aspect of the invention, there is provided a composition comprising the compound of formula 1 and a pharmaceutically acceptable carrier. Preferably, the composition further comprises a compound having anti-HCV activity. As used herein, the term "anti-HCV activity" means the compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection. Often, the other compound having anti-HCV activity is effective to inhibit the function of target in the HCV life cycle other than the HCV NS5A protein.

In one preferred aspect, the compound having anti-HCV activity is an interferon. Preferably, the interferon is selected from the group consisting of interferon alpha 2B, pegylated interferon alpha, consensus interferon, interferon alpha 2A, lymphoblastiod interferon tau.

In another aspect of the invention, the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In one preferred aspect of the invention, the composition comprises a compound of the invention, an interferon and ribavirin.

In another preferred aspect of the invention, the compound having anti-HCV activity is a small molecule compound. As used herein, the term "small molecule compound" means a compound having a molecular weight of less than 1,500 daltons, preferably less than 1000 daltons. Preferably, the small molecule compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, inosine monophophate dehydrogenase ("IMPDH") and a nucleoside analog for the treatment of an HCV infection.

Certain illustrative HCV inhibitor compounds which can be administered with the compounds of the present invention include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this invention. The compounds of the invention can be administered with other anti-HCV activity compounds in combination therapy, either jointly or separately, or by combining the compounds into a composition.

TABLE 1

| Brand Name | Type of Inhibitor or Target | Source Company |
| --- | --- | --- |
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |

TABLE 1-continued

| Brand Name | Type of Inhibitor or Target | Source Company |
| --- | --- | --- |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/ Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Other suitable carriers for the above noted compositions can be found in standard pharmaceutical texts, e.g. in "Remington's Pharmaceutical Sciences", 19th ed., Mack Publishing Company, Easton, Pa., 1995.

The pharmaceutical compositions can be prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable enantiomers, diastereomers, salts, solvates or prodrugs are formulated together with a pharmaceutically acceptable carrier, the resulting composition may be administered in vivo to mammals, such as man, to inhibit HCV NS5A or to treat or prevent HCV virus infection.

Accordingly, another aspect of this invention provides methods of inhibiting HVC NS5A activity in patients by administering a compound of the present invention or a pharmaceutically acceptable enantiomer, diastereomer, salt or solvate thereof.

In one aspect of the invention, there is provided a method of inhibiting the function of the HCV NS5A protein comprising contacting the HCV NS5A protein with a compound of the invention. In another aspect, there is provided a method of treating an HCV infection in a patient, comprising administering to the patient a therapeutically effective amount of the compound of the invention, or a pharmaceutically acceptable enantiomer, diastereomer, solvate, prodrug or salt thereof.

Preferably, the method of administering the compound is effective to inhibit the function of the HCV NS5A protein. In a preferred aspect, the method further comprises administering another compound having anti-HCV activity (as described above) prior to, after or concurrently with a compound of the invention.

The compounds of the invention may also be used as laboratory reagents. Compounds may be instrumental in providing research tools for designing of viral replication assays, validation of animal assay systems and structural biology studies to further enhance knowledge of the HCV disease mechanisms. Further, the compounds of the present invention are useful in establishing or determining the binding site of other antiviral compounds, for example, by competitive inhibition.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the invention can be used for the manufacture of a medicament for treating HCV infection in a patient.

REACTION SCHEMES AND EXAMPLES

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts ($\delta$) are reported in parts per million. Flash chromatography was carried out on silica gel ($SiO_2$) according to Still's flash chromatography technique (W. C. Still et al., J. Org. Chem., (1978), 43, 2923).

HPLC Method:
HPLC: Shimadzu Analytical HPLC running Discovery VP software
Column: YMC 3.0 millimeters ("mm")×50 mm ODS
Flow Rate: 5 milliliters/minute ("mL/min.")
Detector: Shimadzu SPD-10AV:UV at 220 nanometers ("nM")
Method: 0–100% B with 2 minute gradient and 1 minute hold (3 minute runtime)
Injection volume: 5 uL using Shimadzu SIL-10A auto injector.
% A: 10% Methanol/90% Water, 0.1% Trifluoroacetic acid
% B: 90% Methanol/10% Water, 0.1% Trifluoroacetic acid.

Mass Spectrometry (MS) data were determined with a Micromass Platform for LC in electrospray mode (ES+).

The abbreviations used in the present application, including particularly in the illustrative examples which follow, are well-known to those skilled in the art. Some of the abbreviations used are as follows:

| | |
|---|---|
| rt | room temperature |
| Boc | tert-butyloxycarbonyl |
| DMSO | dimethylsulfoxide |
| EtOAc | ethyl acetate |
| t-BuOK | potassium t-butoxide |
| $Et_2O$ | diethyl ether |
| TBME | tert-butylmethyl ether |
| THF | tetrahydrofuran |
| CDI | carbonyldiimidazole |
| DBU | 1,8-diazabicyclo[5.4.0]undec-7-ene |
| TFA | trifluoroacetic acid |
| NMM | N-methylmorpholine |
| HATU | O-7-azabenzotriazol-l-yl |
| HBTU | O-{1H-benzotriazol-1-yl)-N,N,N',N'-tetramethyluronium hexafluorophosphate |
| HOBT | N-hydroxybenzotriazole |
| PyBrop | bromo-bis-pyrrolidine-phosphonium hexafluorophosphate |
| DMF | dimethylformamide |
| MeOH | methanol |
| EDTA | ethylenediaminetetraacetic acid |
| HRMS | high resolution mass spectrometry |
| DMAP | 4-dimethylaminopyridine |
| DIPEA | diisopropylethylamine |
| DCM | dichloromethane |
| DCE | dichloroethane |
| nt | nucleotide |
| UTR | untranslated region |
| ORF | open reading frame |
| DMEM | Dulbecco's Modified Eagle Medium |
| FRET | fluorescence resonance energy transfer |
| 5× | five times the final concentration |
| HTS | high throughput screen |
| ABI | Applied Biosystem, Inc. |
| EDANS | 5-[(2'-aminoethyl)amino]naphthalenesulfonic acid |
| DABCYL | 4-[[4'-(dimethylamino)phenyl]azo]benzoic acid |
| HRP | horseradish peroxidase |
| SDS-PAGE | sodium dodecyl sulfate polyacrylamide gel electrophoresis |
| qRT-PCR | quantitative reverse transcriptase - polymerase chain reaction |
| G418 | geneticin |
| wt | wild type |

General methods useful for the syntheses of compounds of this invention is shown below. The preparations shown below are disclosed for the purpose of illustration and are not meant to be interpreted as limiting the processes to make the compounds by any other methods. The starting materials useful to synthesize the compounds of the present invention are known to those skilled in the art and can be readily manufactured or are commercially available. It will be appreciated by those skilled in the art that a number of methods are available for the preparation of the compounds of the present invention. These compounds may be prepared by processes which include processes known in the chemical art for the production of structurally analogous compounds or by a novel process described herein. A process for the preparation of these compounds (or a pharmaceutically acceptable salt thereof) and novel intermediates for the manufacture of these compounds provide further features of the invention and are illustrated by the following procedures in which the meanings of the generic radicals are as defined above, unless otherwise specified. It will be recognized that it may be preferred or necessary to prepare such a compound in which a functional group is protected using a conventional protecting group then to remove the protecting group to provide a compound of the present invention.

General synthetic scheme 1 outlines the route for preparation of compounds of formula I. Addition of an amine to an isothiocyanate, step 1a, gives a thiourea as depicted in intermediate A. The reaction of intermediate A with an α-bromophenylacetic ester (azido or nitro substituted) as in step 2a & 2a' provides an iminothiazolidinone ring system, intermediate B & B'. Reduction of an azido/nitro functional group in step 3a gives intermediate C which can be coupled with a protected amino acid as in step 4a to give formula I type compounds.

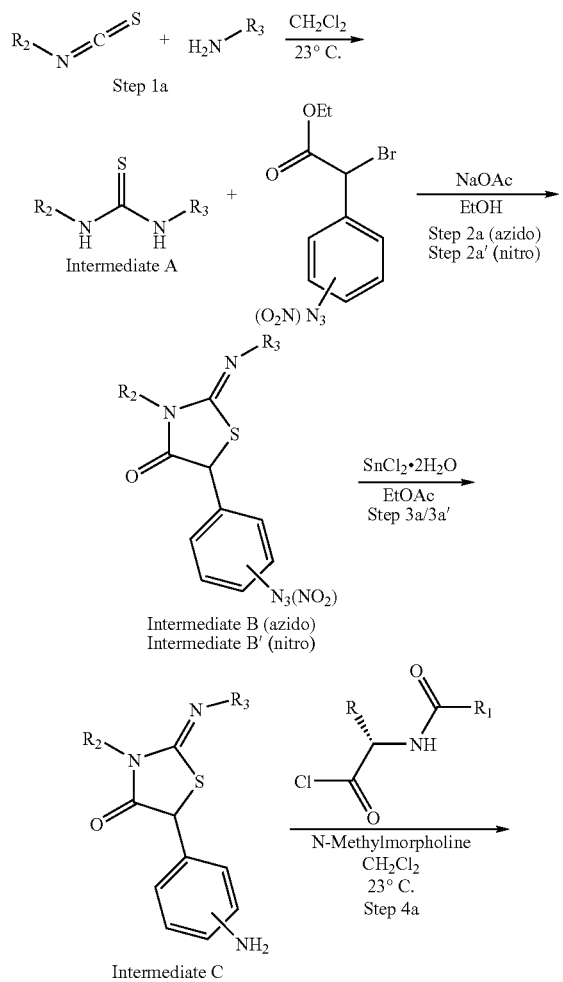

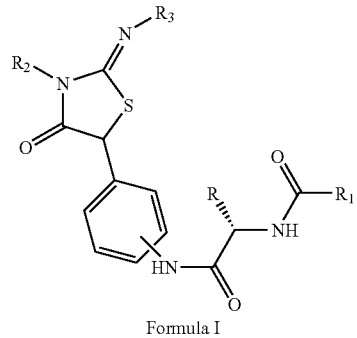

Formula I

Preparation of Reactants Used for Synthesis of Intermediates

α-Bromo-p-azidophenylacetic Acid Ethyl Ester (from p-azidophenylacetic acid). See: Vito Nacci, Giuseppe Campiani, Isabella Fiorini, Maria P. De Fillippis, Antonio Garofalo, Silvia M. Ciani, Giovanni Greco, Ettore Novellino, D. Clive Williams, Daniela M. Zisterer, Margaret J. Woods, Carmelia Mihai, Cristina Manzoni, Tiziana Mennini "Synthesis, Biological Activity and SARs of Pyrrolobenzoxazepine Derivatives, a new class of Specific "Peripheral-Type" Benzodiazepine Receptor Ligands" J. Med. Chem. 39 3435 (1996).

Preparation of Compound 1

As an example, compound I was prepared according the general synthetic scheme in the following way:

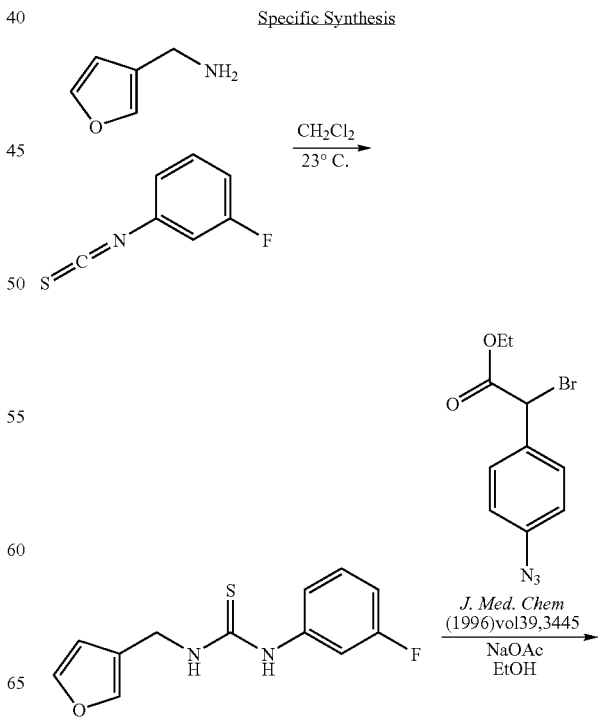

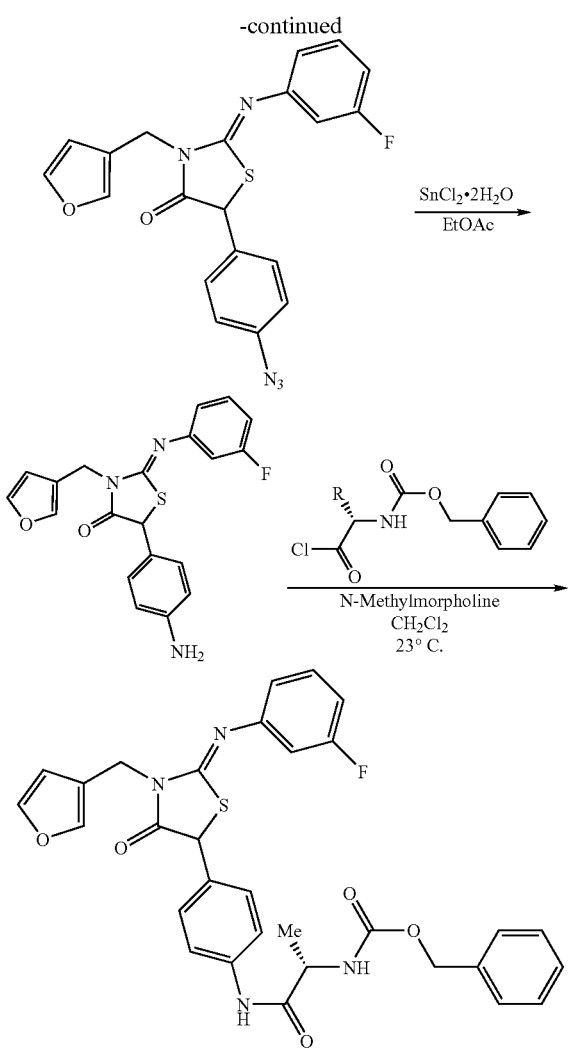

Preparation of Intermediate Compound A Using General Synthesis—Step 1a 1-(3-Fluorophenyl)-3-furan-2-ylmethyl-thiourea Furfuryl amine (3.81 g, 39 millimole ("mmol")) in 125 milliliters ("ml") of anhydrous dichloromethane was added dropwise to 3-fluorophenyl isothiocyanate (5.7 g, 37 mmol) in 30 ml of the same solvent. The reaction was stirred at room temperature for 3 days, concentrated, and subject to chromatography on silica gel (30% ethyl acetate/hexanes) to give 9.3 g (82%) which crystallized upon standing. $^1$H NMR (300 MHz) (CDCl3) δ 4.86 (d, J=5.1 Hz, 2H); 6.29–6.34 (m, 3H); 6.93–7.0 (m, 3H); 7.34–7.41 (m, 2H); 7.98 (br s., 1H); MS (ESI) m/z=251 (MH$^+$); HPLC rt 1.32 min; Purity (100%).

Preparation of Intermediate Compound B Using General Synthesis—Step 2a 5-(4-Azidophenyl)-2-(3-fluorophenylimino)-3-furan-2-ylmethylthiazolidin-4-one Bromo-p-azidophenylacetic acid ethyl ester (800 mg, 2.83 mmol) and 1-(3-fluorophenyl)-3-furan-2-ylmethyl thiourea (706 mg, 2.83 mmol) were dissolved in absolute ethanol (70 ml) and sodium acetate (3 g, 36.6 mmol) added. The solution was heated at 70° C. for 4.5 h, concentrated to ½ volume, diluted with water and ethyl acetate. The aqueous layer was extracted with diethyl ether prior to washing with brine, and the combined organic layers were concentrated and the resultant residue chromatographed on silica gel (elution with 10% ethyl acetate/hexanes). $^1$H NMR (300 MHz) (CDCl3) δ 5.00–5.12 (m, 2H); 5.15 (s, 1H); 6.33–6.35 (m, 1H), 6.40 (d, J=3.3 Hz, 1H); 6.74 (dt, J=9.9 Hz, J=2.2 Hz, 1H); 6.77–6.87 (m, 2H); 6.98–7.02 (m, 2H); 7.27–7.33 (m, 3H); 7.37–7.38 (m, 1H); MS (ESI) m/z=408.0 (MH$^+$); HPLC rt 1.76 min; Purity (80%).

Parallel Procedure For Cyclization Of Thioureas With Bromo-p-azidophenylacetic Acid Ethyl Ester: A Genevac Carousel Reactor was charged with an array of thioureas (0.16 to 0.17 mmol) and anhydrous sodium acetate (27 mg, 0.33 mmol to 32 mg, 0.39 mmol) was added to each vessel. A 1 ml stock solution (0.17 M) of (+/−)-α-bromo-p-azidophenyl-acetic acid ethyl ester (0.17 mmol) in absolute ethanol was added followed by further dilution with abs. ethanol (3.0 ml). The reactions were heated under nitrogen at 75° C. for 1.5 h, and products purified by preparative reverse phase HPLC (applied directly or as a 1:1 THF: ethanol with no intervening workup.

Preparation of Intermediate Compound C Using General Synthesis-Step 3a 5-(4-Aminophenyl)-2-(3-fluorophenylimino)-3-furan-2-ylmethylthiazolidin-4-one 5-(4-Azidophenyl)-2-(3-fluorophenylimino)-3-furan-2-ylmethyl-thiazolidin-4-one (913 mg, 2.24 mmol) was dissolved ethyl acetate (200 ml), tin (II) chloride dihydrate (1.53 g, 6.78 mmol) added, and the reaction mixture heated 2 h at 60° C. After being cooled, a precipitate was filtered and washed with ethyl acetate. The filtrate was washed with sodium bicarbonate solution and aqueous phase extracted with ethyl acetate, and the combined organic layers were washed with brine and dried (MgSO$_4$) to give an amber residue, 831 mg (97%). $^1$H NMR (300 MHz) (CDCl3) δ 4.99–5.11 (m, 3H); 6.32–6.34 (m, 1H), 6.39 (d, J=2.9 Hz, 1H); 6.61–6.65 (m, 2H); 6.72 (dt, J=9.9 Hz, J=2.2 Hz, 1H); 6.76–6.85 (m, 2H); 7.05–7.09 (m, 2H); 7.23–7.31 (m, 1H); 7.36–7.37 (m, 1H); MS (ESI) m/z=382.1 (MH$^+$); HPLC rt 1.44 min (Column: YMC XTerra); Purity (63%).

Parallel Procedure For Reduction Of Azides To Anilines: A Genevac Carousel Reactor was charged with an array of phenyl azide substrates (0.16 to 0.17 mmol) dissolved in 12 ml of ethyl acetate and tin(II) chloride dihydrate (110 mg, 0.5 mmol to 130 mg, 0.6 mmol) was added. The reaction mixture was flushed with nitrogen and heated at 65° C. for 2 h, cooled, and diluted with 7 ml aqueous NaHCO$_3$ soln (1 part saturated NaHCO$_3$: 2 parts de-ionized water). The organic layer was removed by pipet, and the aqueous phase extracted repeatedly (ethyl acetate). The combined organic layers were dried over MgSO$_4$ to give products used without further purification.

Preparation of Compound 1 Using General Synthesis—Step 4a (1S-(4-[2-(3-Fluorophenylimino)-3-furan-2-ylmethyl-4-oxo-thiazolidin-5-yl]-phenylcarbamoyl)ethyl)carbamic acid benzyl ester. An acid chloride solution, prepared from carbobenzyloxy-L-alanine (480 mg, 2.16 mmol) in dichloromethane (15 ml) and 1.0 ml of oxalyl chloride (2M in dichloromethane) at room temperature stirred under nitrogen for 30 min, was added dropwise to a solution of 5-(4-aminophenyl)-2-(3-fluorophenylimino)-3-furan-2-ylmethyl-thiazolidin-4-one (327 mg, 0.86 mmol) and 4-methylmorpholine (0.25 ml, 2.16 mmol) in 30 ml of dichloromethane. The reaction was stirred 10 min at ambient temperature, and then placed in a freezer at −5° C. for 48 h. Upon warming, the reaction was poured onto water, diluted with dichloromethane, and the organic phase washed with brine and dried (MgSO$_4$). Purification by flash chromatography (15% ethyl acetate/dichloromethane) on silica gel gave compound I as a foam. $^1$H NMR (500 MHz) (CD$_3$CN) δ 1.39 (d, J=7.0 Hz, 3H); 4.25 (m, 1H); 5.02 (s, 1H); 5.11 (br. M, 2H); 5.32 (s, 1H); 6.09 (br.s, 1H); 6.42 (m, 2H); 6.78 (td, J=10.4 Hz, J=2.4 Hz, 1H); 6.84 (d, J=7.9 Hz, 1H); 6.92 (dt, J=8.6 Hz, J=2.4 Hz, 1H); 7.25–7.44 (m, 8H); 7.48 (s, 1H); 7.58 (d, J=8.2 Hz, 2H); 8.65 (br.s, 1H); $^{13}$C NMR (125 MHz) (CD$_3$CN) δ 17.8, 39.8, 51.5, 51.9, 66.7, 108.7 (J$_{CF}$=22.3 Hz), 109.1, 111.1, 111.5 (J$_{CF}$=21.3 Hz), 117.4 (J$_{CF}$=2.2 Hz), 120.5, 128.3 (J$_{CF}$=22.1 Hz), 128.9, 129.4, 131.3, 131.4, 131.6, 137.5, 139.4, 142.9, 149.8, 150.4 (J$_{CF}$=9.4 Hz), 154.5, 156.5, 163.6 (J$_{CF}$=244.9 Hz), 171.9, 173.1. IR: (film, NaCl) CM$^{-1}$ 3321.0 (broad NH), 1724.6, 1685.1, 1638.1, 1602.4, 1535.1, 1515.6; MS (ESI) m/z=587 (MH$^+$); HPLC rt 2.45 min; Purity (100%).

Preparation of Compound 1 Using Alternate Resin Coupling in General Synthesis—Step 4a Resin coupling: A 48-well Bodhan Mini-Reactor was charged with N-cyclohexylcarbodiimide N-methylpolystyrene resin (195 mg, 0.32 mmol) from [Nova Biochem, loading=1.65 mMol/g] and carbobenzyloxy-L-alanine (29 mg, 0.12 mmol) and 1,2-dichloroethane (1.0 ml) and a solution of 5-(4-aminophenyl)-2-(3-fluorophenylimino)-3-furan-2-ylmethyl-thiazolidin-4-one (20 mg, 0.05 mmol) in 1,2-dichloroethane (1.0 ml). After being stirred 18 h at 600 rpm the reaction mixture was drained through a filter to remove resin and solvent removed in vacuo to give compound I as an amorphous yellow solid 16.2 mg (53%). MS (ESI) m/z=587 (MH$^+$); HPLC rt 2.45 min; Purity (85.3%).

General Procedure For Parallel Coupling Of Carboxylic Acids To 5-(4-aminophenyl)-2-(3-fluorophenylimino)-3-furan-2-ylmethyl-thiazolidin-4-one. A 48-well Bodan Mini-Reactor was charged with N-cyclohexylcarbodiimide N-methylpolystyrene resin (195 mg, 0.32 mmol) [Nova Biochem, loading=1.65 mmol/g) and N-protected amino acid (0.12 mmol) dissolved in 1.0 ml of 1,2-dichloroethane. A solution of 5-(4-Aminophenyl)-2-(3-fluorophenylimino)-3-furan-2-ylmethyl-thiazolidin-4-one (20 mg, 0.05 mmol) in the same solvent (0.5 ml) was added followed by an additional 0.5 ml solvent to bring the total reaction volume to 2 ml. After being stirred 18 h at 600 rpm the reaction mixtures were drained through a filter to remove resin and solvent removed in vacuo to give coupled product. Products may be purified by reverse phase preparative HPLC to enhance purity (>95%) and give products in 50% average yield.

Example Preparation of Intermediate B' Using General Synthesis—Step 2a'

2-Isopropylimino-5-(4-nitro-phenyl)-3-pyridin-2-ylmethyl-thiazolidin-4-one Bromo-(4-nitrophenyl)acetic acid ethyl ester was prepared via bromination (Br$_2$, 70° C., 6 h, followed by EtOH quench) of (4-nitrophenyl)acetyl chloride to afford the known α-bromo ester [Synth. Comm. (1994), 24: 965]. To this ester (6.88 g, 23.9 mmol) in 75 ml absolute ethanol was added 1-(isopropyl)-3-(pyridin-2-ylmethyl)-2-thiourea (5.0 g, 23.9 mmol) in one portion at room temperature under nitrogen. The mixture was heated to 80° C. for 2 h before it was allowed to stir at room temperature overnight. After solvent evaporation, the residue was taken up in ethyl acetate and washed with water and brine. The organic extracts were dried and concentrated to furnish the title compound (9.2 g) as a blood-red, viscous oil which was used directly: 1H NMR (400 MHz, CDCl3) δ 8.52–8.51 (m, 1H), 8.22 (d, J=8.8 Hz, 2H), 7.69 (d, J=8.8 Hz, 2H), 7.66–7.62 (m, 1H), 7.25–7.21 (m, 1H), 7.19–7.16 (m, 1H), 5.33 (s, 1H), 5.09 (s, 2H), 3.44 (septet, J=6.1 Hz, 1H), 1.09–1.06 (m, 6H); MS (ESI) m/z=371.1 (MH$^+$); HPLC rt 1.84 min. (3 min. grad.); Purity (90%).

Example Preparation of Intermediate C from Intermediate B' Using Step 3a'

5-(4-Amino-phenyl)-2-isopropylimino-3-pyridin-2-ylmethyl-thiazolidin-4-one

A solution of 2-isopropylimino-5-(4-nitrophenyl)-3-pyridin-2-ylmethyl-thiazolidin-4-one (4.6 g, 12.4 mmol) in dry methanol (50 ml) was subjected to hydrogenation at slightly above atmospheric pressure (balloon) room temperature for 20 h using Pearlman's catalyst (1.0 g). After 20 h at room temperature, additional catalyst (0.5 g) was added and the suspension was hydrogenated for an additional 24 h. When the reaction was judged complete by LC analysis, the mixture was suction-filtered through Celite and concentrated in vacuo to afford the title compound as a yellowish-tan foam which was used without further purification: $^1$H NMR (400 MHz, CDCl3) δ 8.50 (d, J=4.2 Hz, 1H), 7.61–7.57 (m, 1H), 7.21–7.16 (m, 1H), 7.18 (d, J=8.3 Hz, 2H), 7.14–7.12 (m, 1H), 6.63 (d, J=8.6 Hz, 2H), 5.15 (s, 1H), 5.08 (s, 2H), 3.85–3.60 (br m, 2H), 3.50–3.42 (m, 1H), 1.09–1.06 (m, 6H); MS (ESI) m/z=341.2 (MH$^+$); HPLC rt 1.07 min. (3 min. grad.); Purity (83.5%).

Compounds 2 to 68 were prepared according to General Synthetic Scheme 1 using Alternate Resin Coupling Step 4a. Certain compounds are characterized below.

Preparation of Compound 2

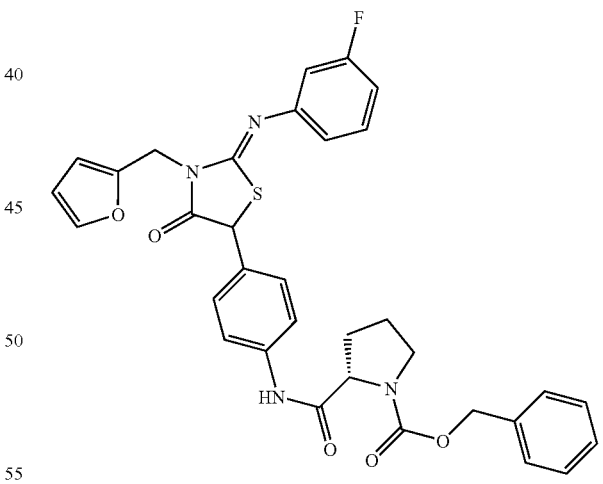

2S-{4-[2-(3-fluorophenylimino)-3-furan-2ylmethyl-4-oxo-thiazolidin-5yl]-phenylcarbamoyl}pyrrolidine-1-carboxylic Acid Benzyl Ester $^1$H NMR (300 MHz) (CD$_3$CN) δ 1.80–2.36 (m, 4H); 3.48–3.60 (m, 2H); 4.94–5.02 (m, 3H); 5.15–5.19 (m, 2H); 6.42 (s, 1H); 6.79 (d, J=10.3 Hz, 1H); 6.84 (d, J=7.7 Hz, 1H); 6.92 (t, J=8.8 Hz, 1H); 7.18–7.55 (m, 12H); 8.61 (br.s, 0.5H); 8.81 (br.s, 0.5H); $^{13}$C NMR (75 MHz) (CD$_3$CN) (rotomeric signals for proline portion of molecule observed) δ 23.8 (CH2, C4 proline), 24.6 (CH2, C4 proline), 30.0

(CH2, C3 proline), 31.6 (CH2, C3 proline), 39.8 (CH2, furfuryl), 47.4 (CH2, C5 proline), 47.8 (CH2, C5 proline), 51.5 (CH, thiazoline ring), 61.5 (CH, C2 proline), 67.0 (CH2, benzyl), 67.1 (CH2, benzyl), 108.7 ($J_{CF}$=23.0 Hz), 109.1, 111.1, 111.5 ($J_{CF}$=21.3 Hz), 117.4 ($J_{CF}$=2.9 Hz), 120.6, 120.7 (broaden CH adjacent to anilide), 128.0 ($J_{CF}$=23.0 Hz) 128.7–128.8 (broad), 129.3, 131.3, 131.4, 139.3, 142.9, 149.8, 150.4 ($J_{CF}$=9.8 Hz), 154.6, 163.6 ($J_{CF}$=244.8 Hz), 173.1 (note: Carbamate carbonyl at ~156.5 and anilide carbonyl at ~171.5 not resolved); MS (ESI) m/z=613 (MH$^+$); High Resolution MS Calc: $C_{33}H_{29}F_1N_4O_5S_1$ [MH$^-$] 611.17644; Found: 611.1754; Dev: 1.7 ppm; HPLC rt 1.74 min; Purity (100%).

Preparation of Compound 3

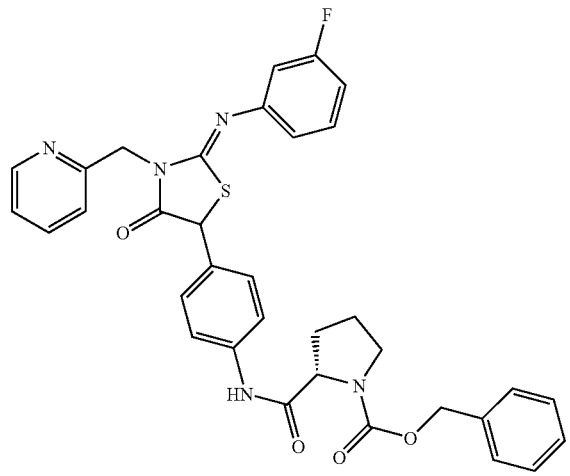

$^1$H NMR (500 MHz) (CD$_3$CN) δ 1.82–2.36 (m, 4H); 3.49–3.62 (m, 2H); 3.84 (s, 2H); 4.33 (br.s, 1H); 4.96–5.21 (m, 2H); 5.25–5.29 (m, 2H); 5.46 (s, 1H); 6.71 (d, J=10.4 Hz, 1H); 6.78 (d, J=7.9 Hz, 1H); 6.92 (td, J=8.2 Hz, J=2.7 Hz); 7.19–7.61 (m, 12H); 8.05 (t, J=7.9 Hz, 1H); 8.68 (d, J=4.6 Hz, 1H), 8.52 (br.s, 0.5H); 8.72 (br.s, 0.3H); LC/MS (ESI) m/z=624 (MH$^+$); High Resolution MS Calc: $C_{34}H_{30}F_1N_5O_4S_1$ [MH$^-$] 622.19243; Found: 622.1929; Dev: −0.8 ppm; HPLC rt 1.61 min; Purity (>95%).

Preparation of Compound 4

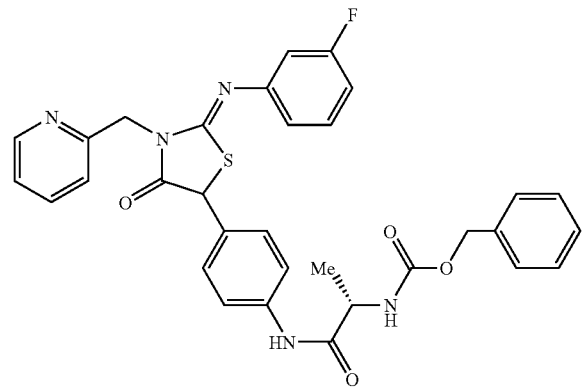

$^1$H NMR (500 MHz) (CD$_3$CN) δ 1.37 (d, J=7.0 Hz, 3H); 4.20 (q, J=6.7 Hz, 1H); 5.05–5.11 (m, 2H); 5.18–5.25 (m, 2H); 5.43 (s, 1H); 6.02 (br.s, 0.5H); 6.68 (dt, J=10.4 Hz, J=2.4 Hz, 1H); 6.73–6.75 (m, 1H); 6.88 (td, J=8.6 Hz, J=2.8 Hz, 1H); 7.31–7.60 (m, 13H); 8.00 (td, J=7.6 Hz, J=1.5 Hz, 1H); 8.57 (br.s, 0.8H); 8.65 (d, J=5.2 Hz, 1H); LC/MS (ESI) m/z=598 (MH$^+$); High Resolution MS Calc: $C_{32}H_{28}F_1N_5O_4S_1$ [MH$^-$] 596.17678; Found: 596.1746; Dev: 3.6 ppm; HPLC rt 1.59 min; Purity (>95%).

Preparation of Compound 5

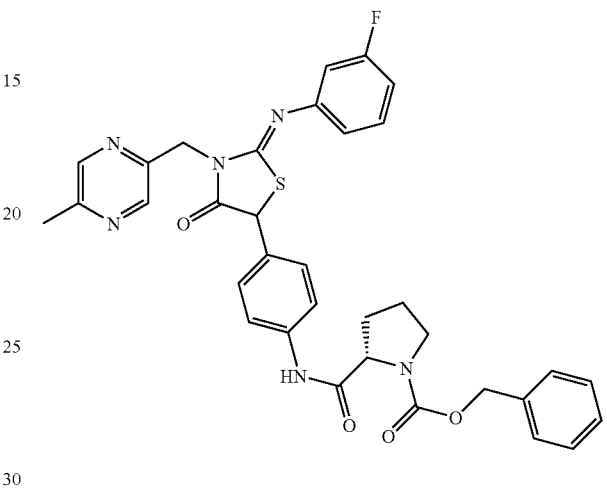

$^1$H NMR (500 MHz) (CD$_3$CN) δ 1.91–2.08 (m, 4H); 2.59 (s, 3H); 3.48–3.57 (m, 2H); 4.30 (br.s, 1H); 4.93–5.16 (m, 4H); 5.39 (s, 1H); 6.66 (d, J=10.4 Hz, 1H); 6.72 (d, J=7.6 Hz, 1H); 6.87 (td, J=8.5 Hz, J=2.4 Hz, 1H); 7.15–7.59 (m, 10H); 8.45 (s, 1H); 8.49 (br.s, 0.4H); 8.52 (s, 1H); LC/MS (ESI) m/z=639 (MH$^+$); High Resolution MS Calc: $C_{34}H_{31}F_1N_6O_4S_1$ [MH$^-$] 637.20333; Found: 637.2042; Dev: 1.4 ppm; HPLC rt 1.74 min; Purity (>95%).

Preparation of Compound 6

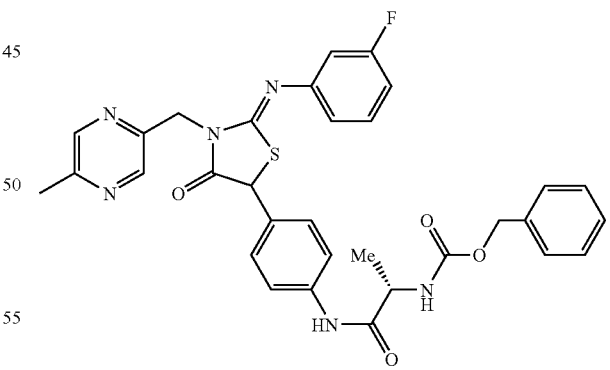

$^1$H NMR (300 MHz) (CD$_3$CN) δ 1.37 (d, J=7.0 Hz, 3H); 2.51 (s, 3H); 4.20 (q, J=7.0 Hz, 1H); 5.09 (s, 2H); 5.13 (s, 2H); 5.39 (s, 1H); 6.02 (br.s, 0.4H); 6.65 (dt, J=10.6 Hz, J=2.2 Hz, 1H); 6.70–6.73 (m, 1H); 6.87 (td, J=8.8 Hz, J=2.6 Hz, 1H); 7.29–7.60 (m, 10H); 8.45 (s, 1H); 8.52 (s, 1H); 8.57 (br.s, 0.8H); LC/MS (ESI) m/z=613 (MH$^+$); High Resolution MS Calc: $C_{32}H_{29}F_1N_6O_4S_1$ [MH$^-$] 611.18768; Found: 611.1901; Dev: −4.0 ppm; HPLc rt 1.73 min; Purity (>98%).

Preparation of Compound 7

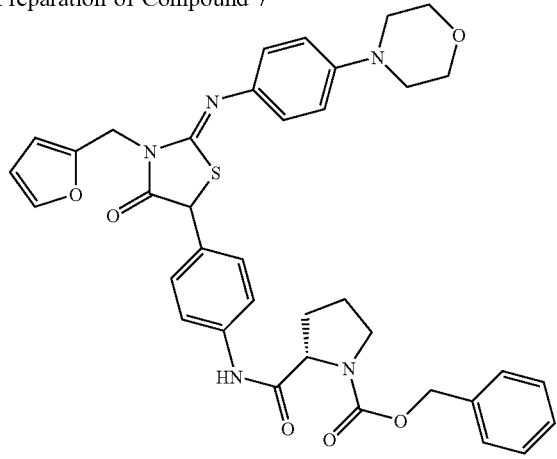

¹H NMR (500 MHz) (CD₃CN) δ 1.85–1.92 (m, 2H); 1.99–2.31 (m, 4H); 3.09 (br.s, 1H); 3.25–3.27 (m, 6H); 3.4–3.6 (m, 10H); 3.72 (br.s, 1H); 3.81 (s, 3H); 3.86–3.88 (m, 4H); 4.29–4.30 (m, 2H); 4.93–5.01 (m, 3H); 5.30 (s, 1H); 6.39–6.40 (m, 2H); 6.81 (m, 0.5H); 7.01 (d, J=8.8 Hz, 2H); 7.15–7.58 (m, 16H); 8.48 (br.s, 0.5H); 8.69 (br.s, 0.5H) NOTE: integration and additional peaks indicate impurities in sample; MS (ESI) m/z=680.4 (MH⁺); High Resolution MS Calc: $C_{37}H_{37}N_5O_6S_1$ [MH⁺] 680.25429; Found: 680.2538; Dev: 0.7 ppm; HPLC rt 1.43 min; Purity (>90%).

Preparation of Compound 8

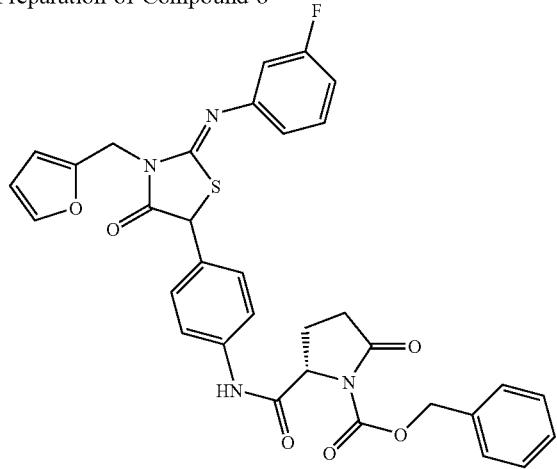

MS(ESI) m/z=627.3 (MH⁺); HPLC rt=1.80 min; Purity (97%).

Preparation of Compound 9

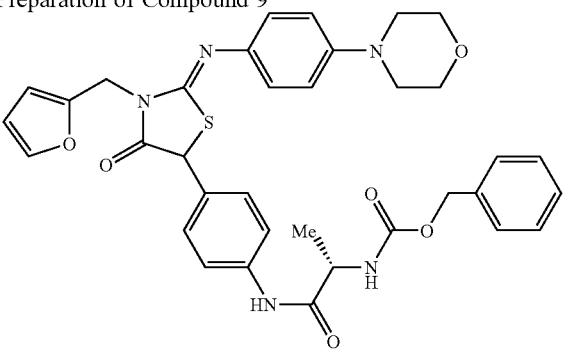

MS(ESI) m/z=573.3 (MH⁺); HPLC rt=1.79 min; Purity (>97%).

Preparation of Compound 10

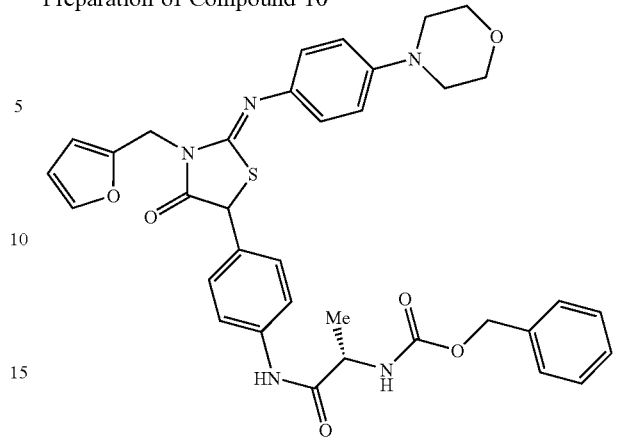

MS (ESI) m/z=654.3 (MH⁺) High Resolution MS Calc: $C_{35}H_{35}N_5O_6S_1$ [MH⁻] 652.22298; Found: 652.2248; Dev: −2.8 ppm; HPLC rt 1.62 min; Purity (>90%).

Preparation of Compound 11

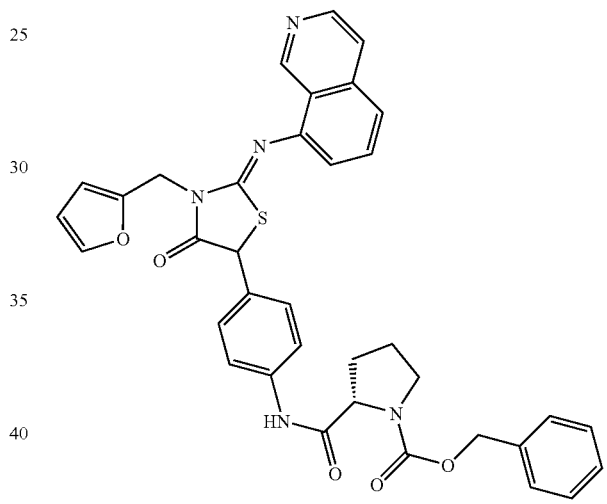

MS (ESI) m/z=646.3 (MH⁺) High Resolution MS Calc: $C_{36}H_{31}N_5O_5S_1$ [MH⁻] 644.19676; Found: 644.1985; Dev: −2.6 ppm; Purity (95%).

Preparation of Compound 12

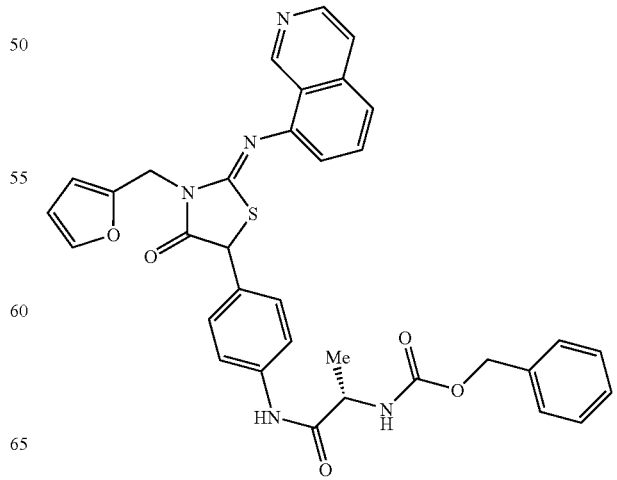

MS (ESI) m/z=620.3 (MH+) High Resolution MS Calc: $C_{34}H_{29}N_5O_5S_1$ [MH−] 620.19677; Found: 620.1979; Dev: −1.8 ppm; HPLC rt 1.30 min; Purity (91%).

Preparation of Compound 13

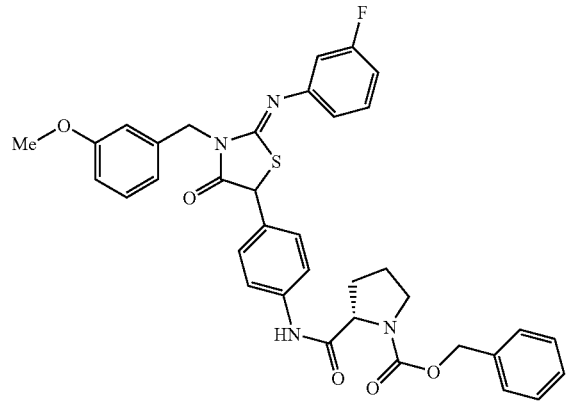

MS(ESI) m/z=653.3 (MH+); HPLC rt 1.97 min; Purity (95%).

Preparation of Compound 14

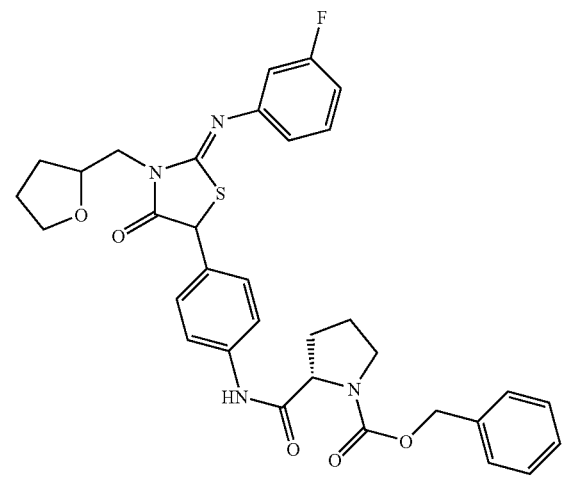

MS(ESI) m/z=617.2 (MH+); HPLC rt 1.84 min; Purity (98%).

Preparation of Compound 15

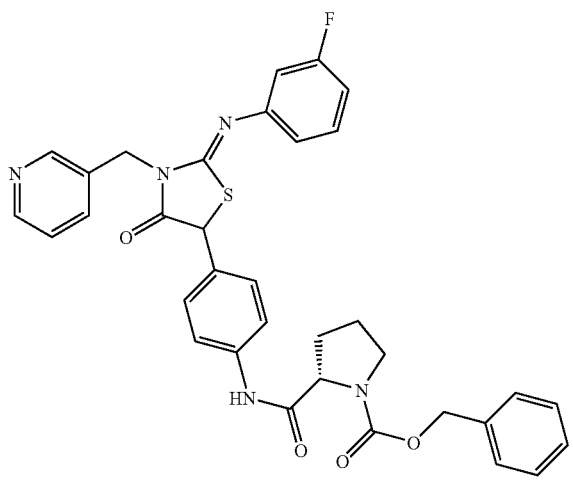

MS(ESI) m/z=624.2 (MH+); HPLC rt 1.58 min; Purity (98%).

Preparation of Compound 16

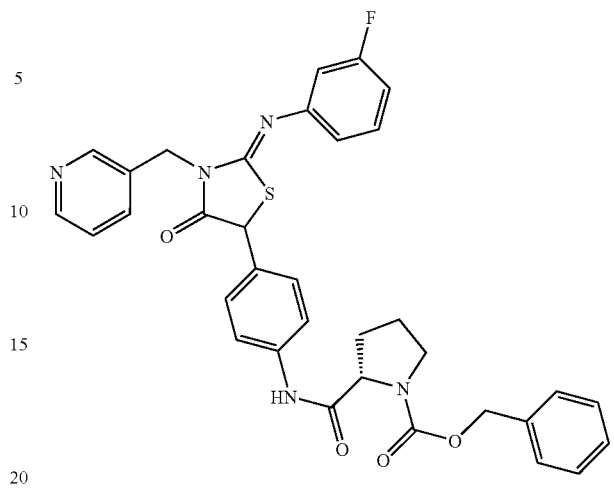

MS(ESI) m/z=623.2 (MH+); HPLC rt 1.96 min; Purity (98%).

Preparation of Compound 17

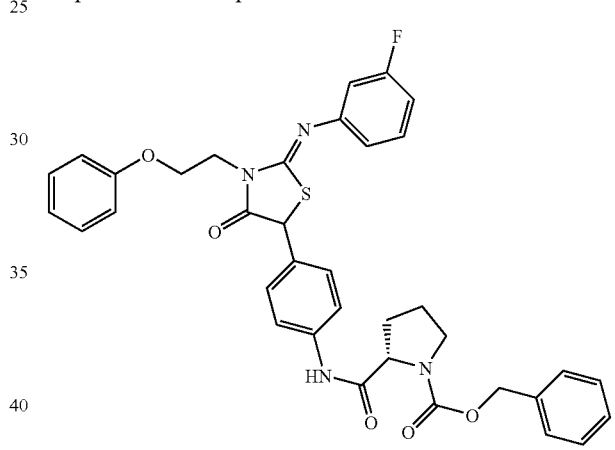

MS(ESI) m/z=653.4 (MH+); HPLC rt 1.91 min; Purity (98%).

Preparation of Compound 18

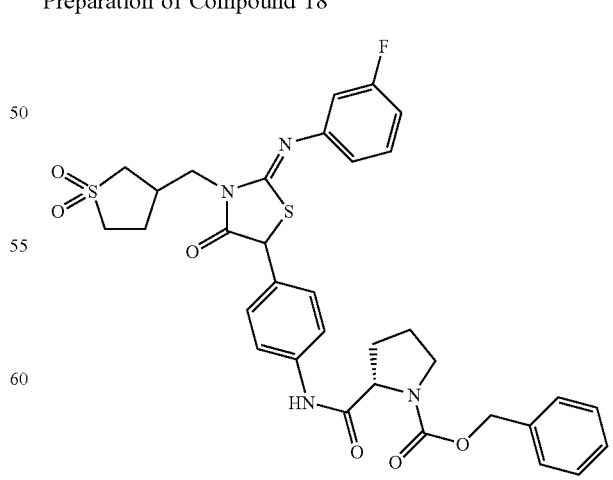

MS(ESI) m/z=651.3 (MH+); HPLC rt 1.63 min; Purity (98%).

Preparation of Compound 19
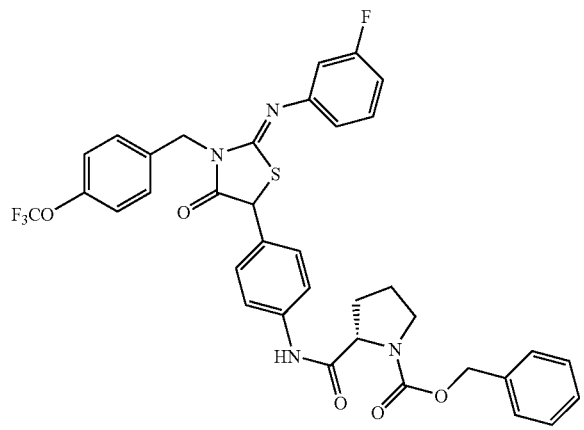
MS(ESI) m/z=707.4 (MH+); HPLC rt 2.04 min; Purity (98%).
Preparation of Compound 20
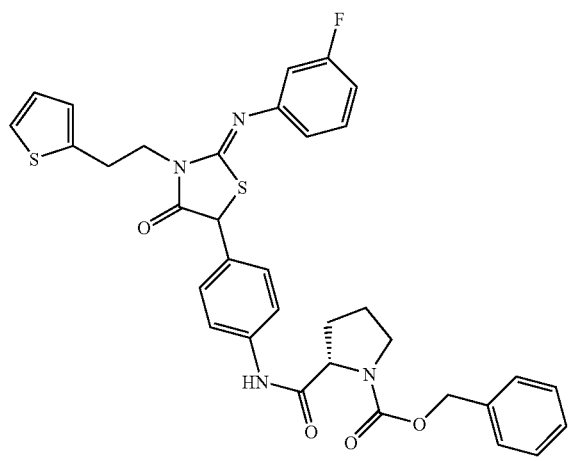
MS(ESI) m/z=643.3 (MH+); HPLC rt 1.95 min; Purity (98%).
Preparation of Compound 21
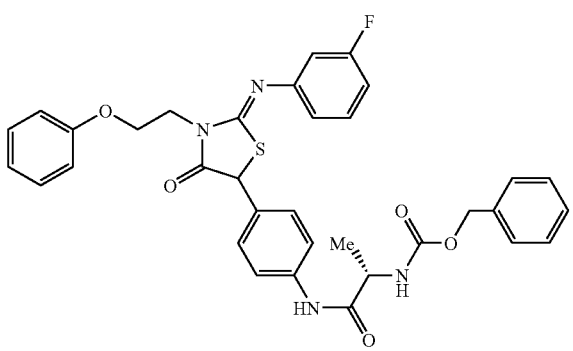
MS(ESI) m/z=627.4 (MH+); HPLC rt 1.80 min; Purity (98%).
Preparation of Compound 22
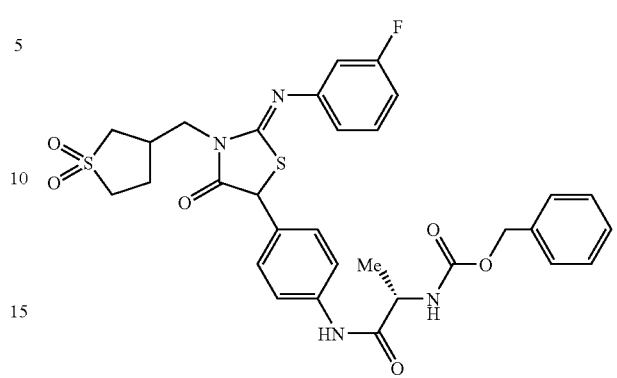
MS(ESI) m/z=625.3 (MH+); HPLC rt 1.52 min; Purity (75%).
Preparation of Compound 23
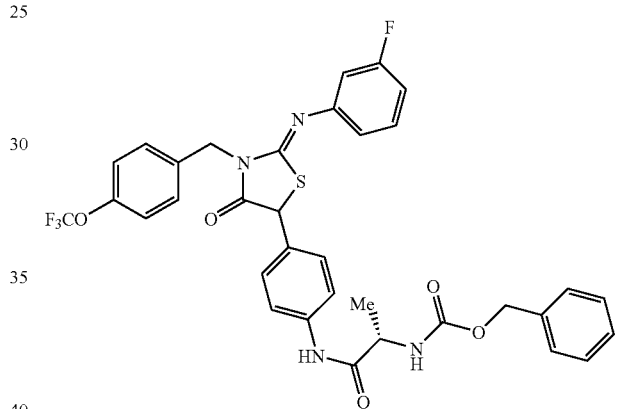
MS(ESI) m/z=681.3 (MH+); HPLC rt 2.02 min; Purity (99%).
Preparation of Compound 24
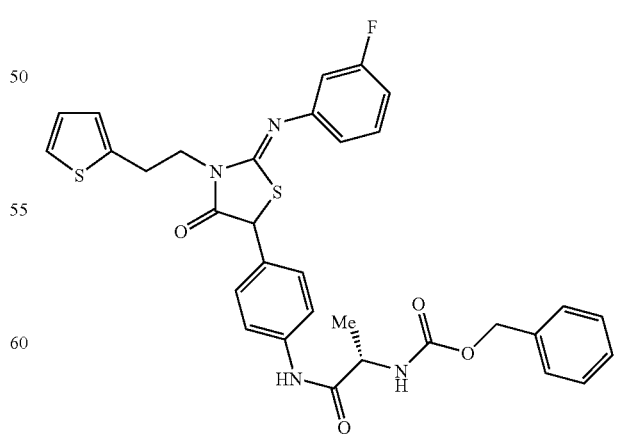
MS(ESI) m/z=617.3 (MH+); HPLC rt 1.91 min; Purity (98%).

Preparation of Compound 25
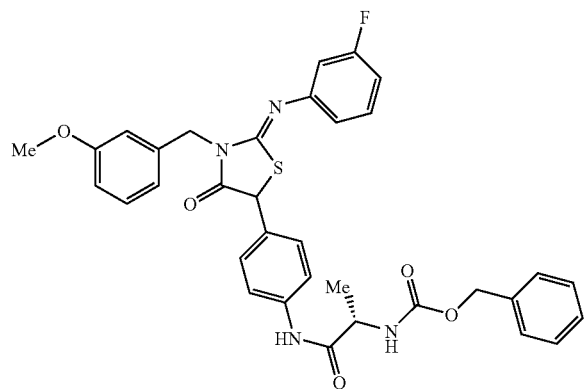
MS(ESI) m/z=627.2 (MH⁺); HPLC rt 1.96 min; Purity (97%).
Preparation of Compound 26
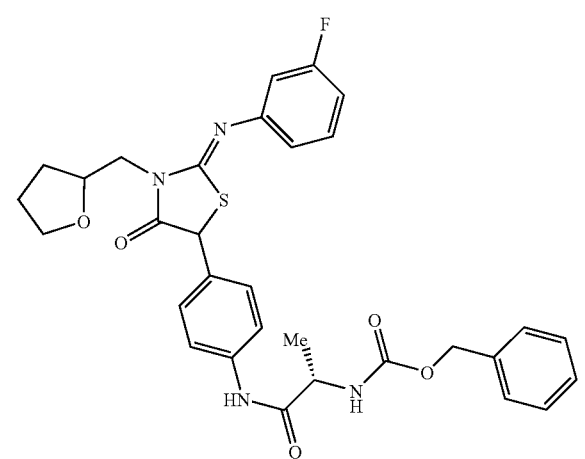
MS(ESI) m/z=591.2 (MH⁺); HPLC rt 1.84 min; Purity (98%).
Preparation of Compound 27
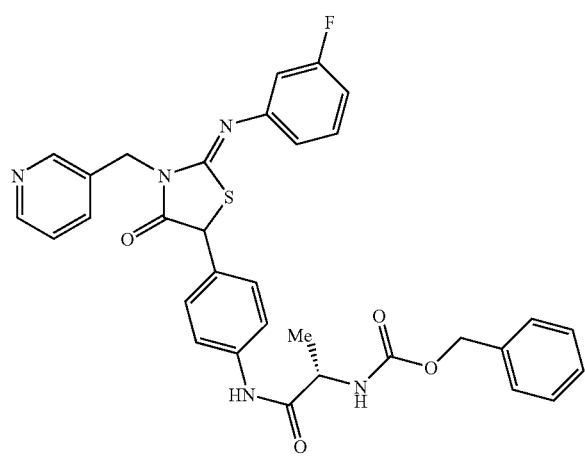
MS(ESI) m/z=598.1 (MH⁺); HPLC rt 1.58 min; Purity (97%).
Preparation of Compound 28
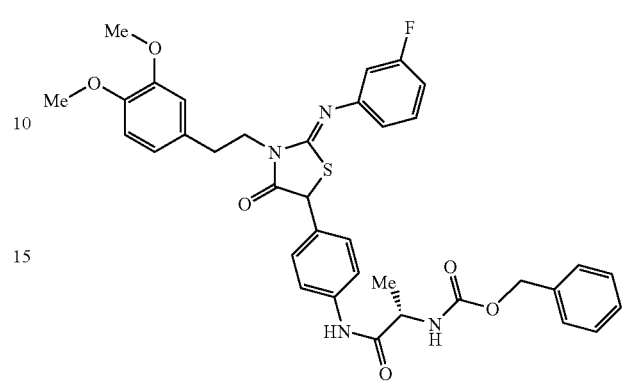
MS(ESI) m/z=671.4 (MH⁺); HPLC rt 1.86 min; Purity (99%).
Preparation of Compound 29
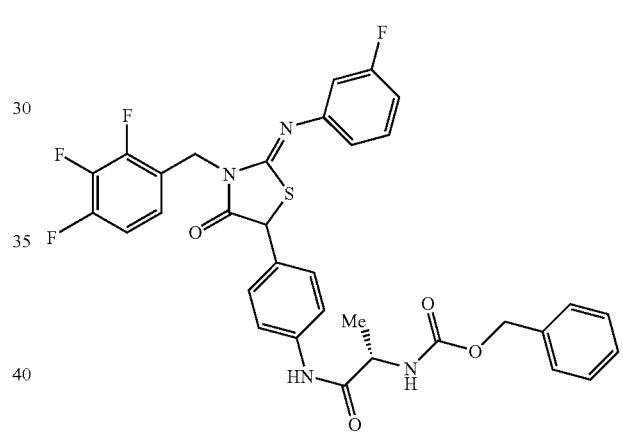
MS(ESI) m/z=651.4 (MH⁺); HPLC rt 1.95 min; Purity (99%).
Preparation of Compound 30
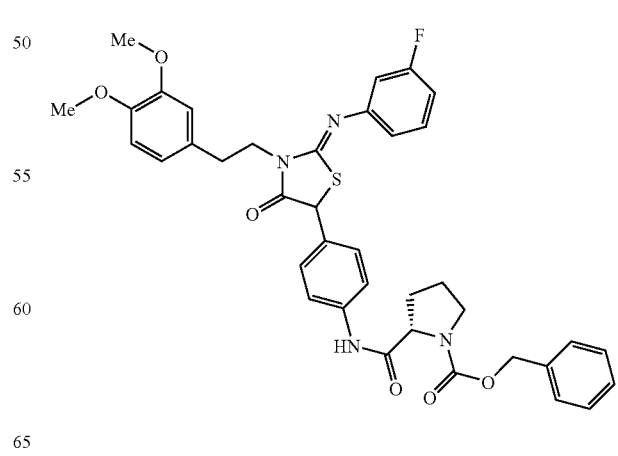
MS(ESI) m/z=697.5 (MH⁺); HPLC rt 1.99 min; Purity (99%).

Preparation of Compound 31
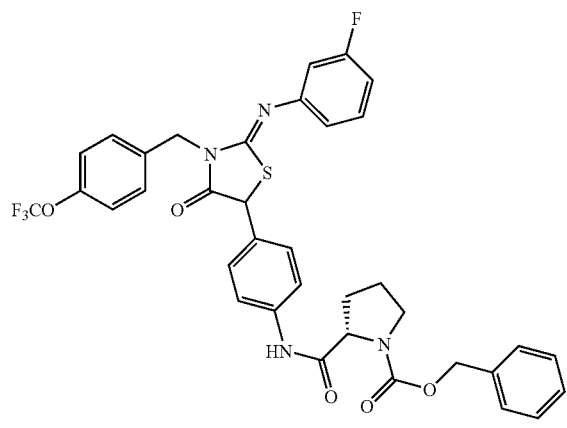
MS(ESI) m/z=6774 (MH⁺); HPLC rt 1.96 min; Purity (99%).
Preparation of Compound 32
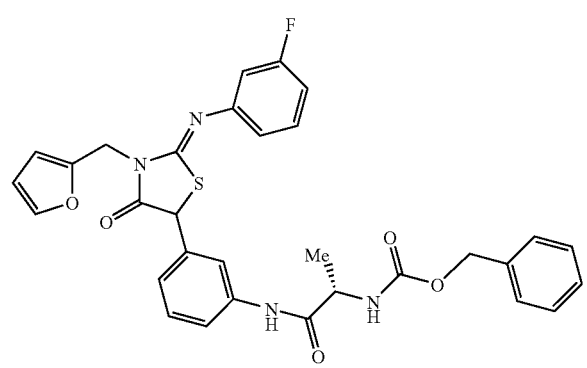
MS(ESI) m/z=587.2 (MH⁺); HPLC rt 1.90 min; Purity (94%).
Preparation of Compound 33
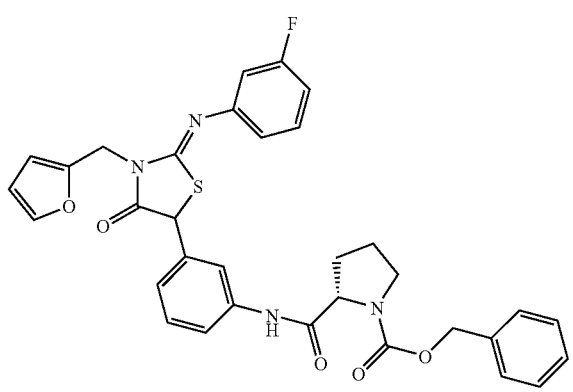
MS(ESI) m/z=613.4 (MH⁺); HPLC rt 1.85 min; Purity (94%).
Preparation of Compound 34
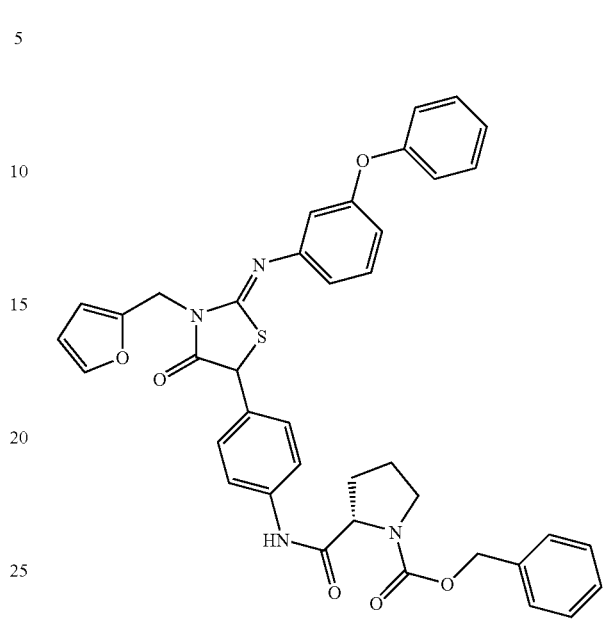
MS(ESI) m/z=678.2 (MH⁺); HPLC rt 2.05 min; Purity (98%).
Preparation of Compound 35
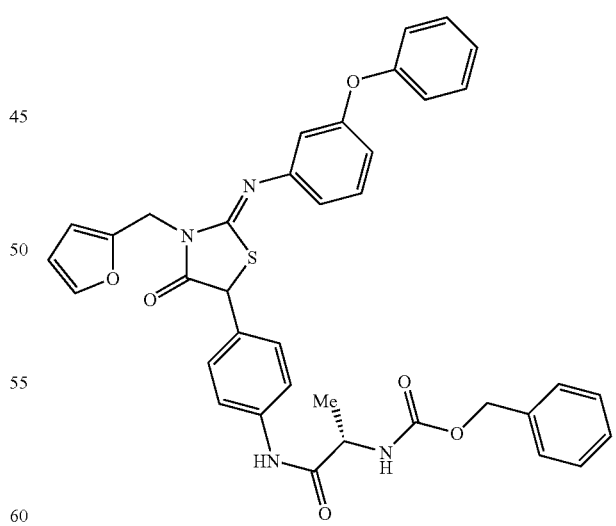
MS(ESI) m/z=667.9 (MH⁺); HPLC rt 2.05 min; Purity (98%).

Preparation of Compound 36
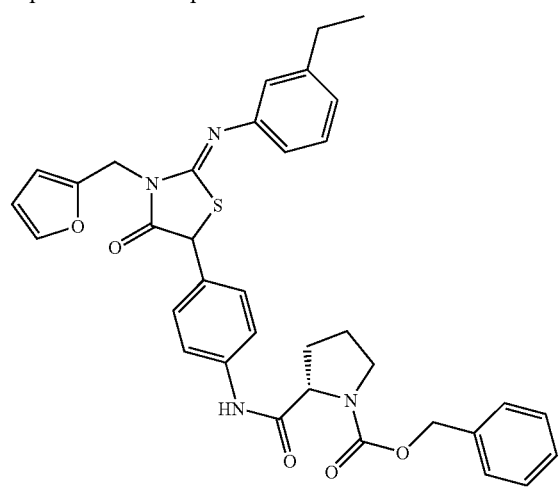
MS(ESI) m/z=623.3 (MH+); HPLC rt 1.99 min; Purity (100%).
Preparation of Compound 37
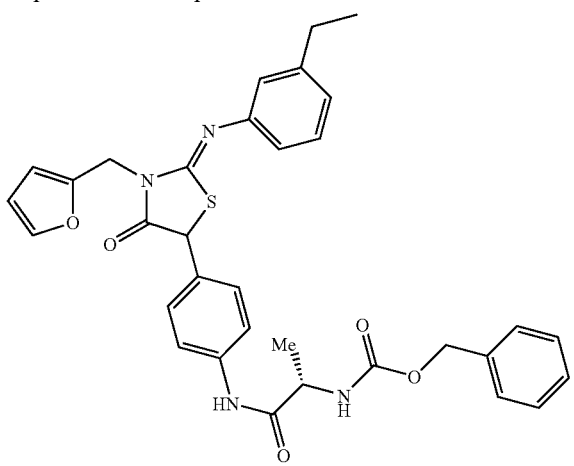
MS(ESI) m/z=597.2 (MH+); HPLC rt 1.98 min; Purity (100%).
Preparation of Compound 38
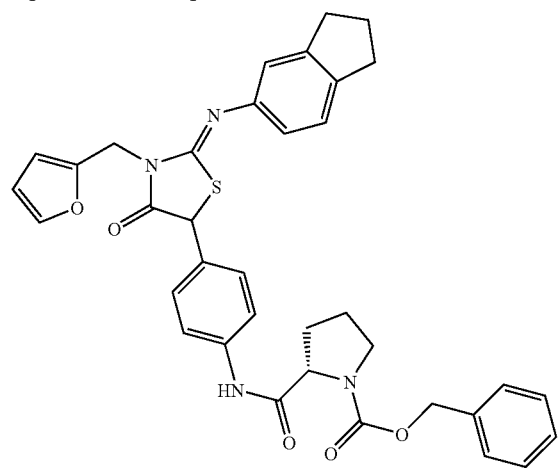
MS(ESI) m/z=635.2 (MH+); HPLC rt 2.03 min; Purity (100%).
Preparation of Compound 39
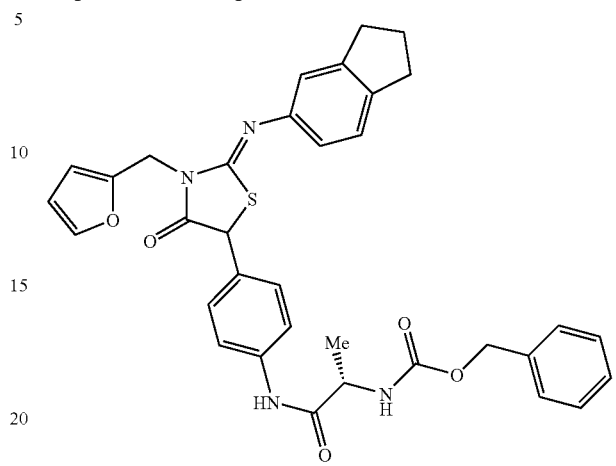
MS(ESI) m/z=608.1 (MH+); HPLC rt 2.04 min; Purity (95%).
Preparation of Compound 40
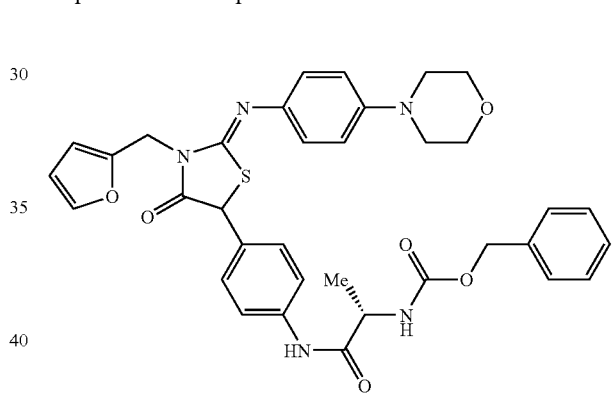
MS(ESI) m/z=643.2 (MH+); HPLC rt 2.04 min; Purity (99%).
Preparation of Compound 41
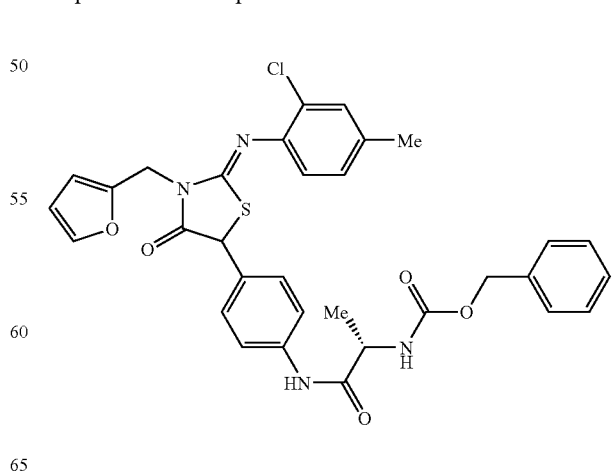
MS(ESI) m/z=617.2 (MH+); HPLC rt 2.03 min; Purity (99%).

Preparation of Compound 42
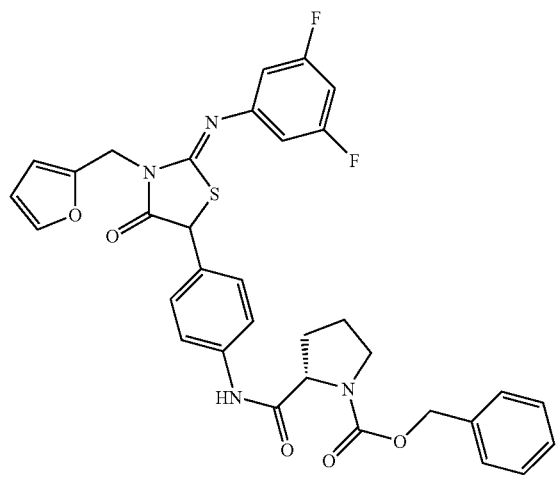
MS(ESI) m/z=631.2 (MH⁺); HPLC rt 1.96 min; Purity (99%).
Preparation of Compound 43
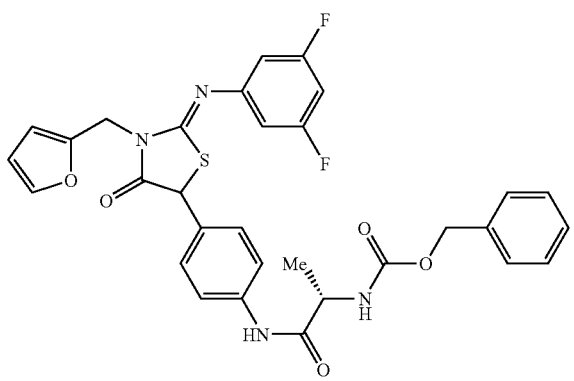
MS(ESI) m/z=605.2 (MH⁺); HPLC rt 2.04 min; Purity (98%).
Preparation of Compound 44
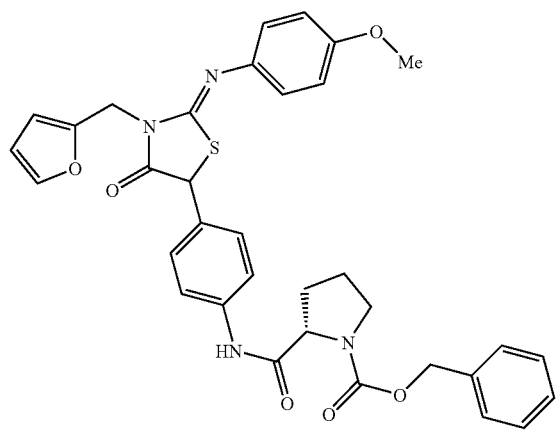
MS(ESI) m/z=626.3 (MH⁺); HPLC rt 1.77 min; Purity (99%).
Preparation of Compound 45
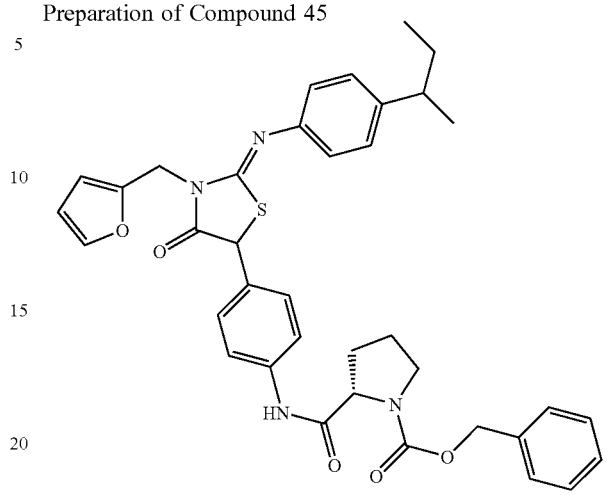
MS(ESI) m/z=651.2 (MH⁺); HPLC rt 2.14 min; Purity (99%).
Preparation of Compound 46
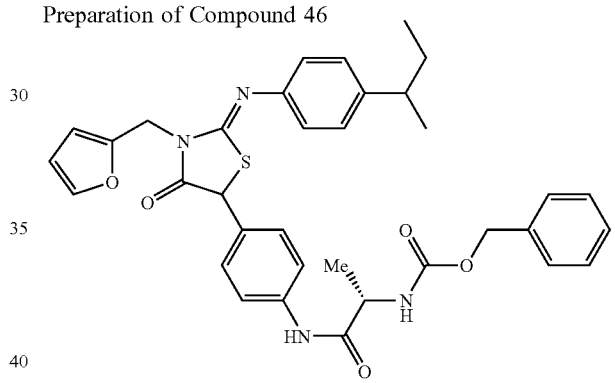
MS(ESI) m/z=625.2 (MH⁺); HPLC rt 2.1 min; Purity (100%).
Preparation of Compound 47
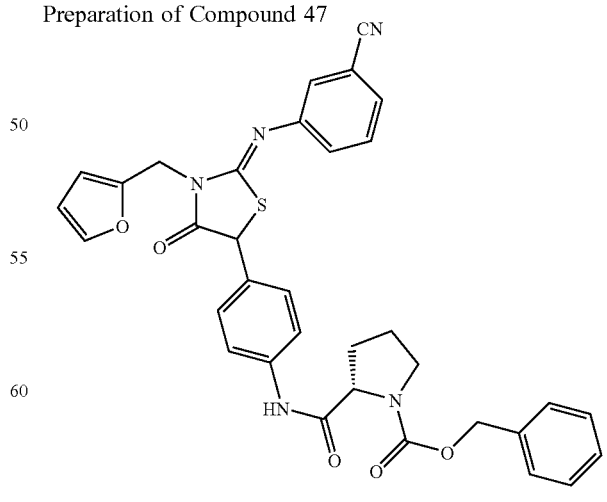
MS(ESI) m/z=620.2 (MH⁺); HPLC rt 1.8 min; Purity (98%).

Preparation of Compound 48
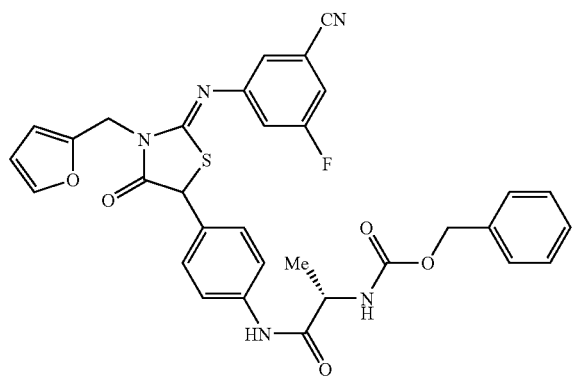
MS(ESI) m/z=594.2 (MH⁺); HPLC rt 1.78 min; Purity (98%).
Preparation of Compound 49
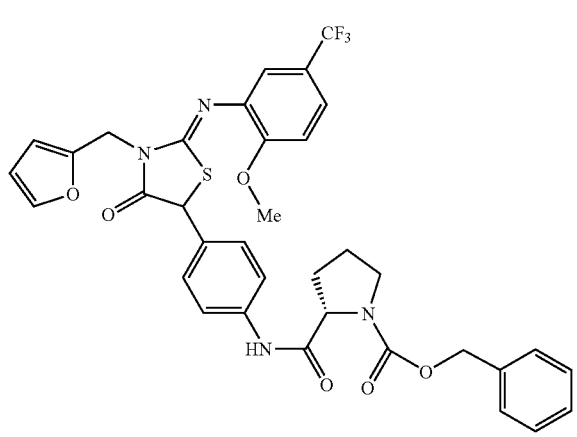
MS(ESI) m/z=693.2 (MH⁺); HPLC rt 1.98 min; Purity (98%).
Preparation of Compound 50
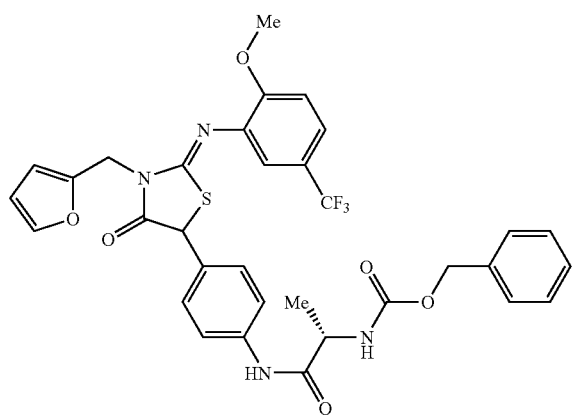
MS(ESI) m/z=667.1 (MH⁺); HPLC rt 1.97 min; Purity (84%).
Preparation of Compound 51
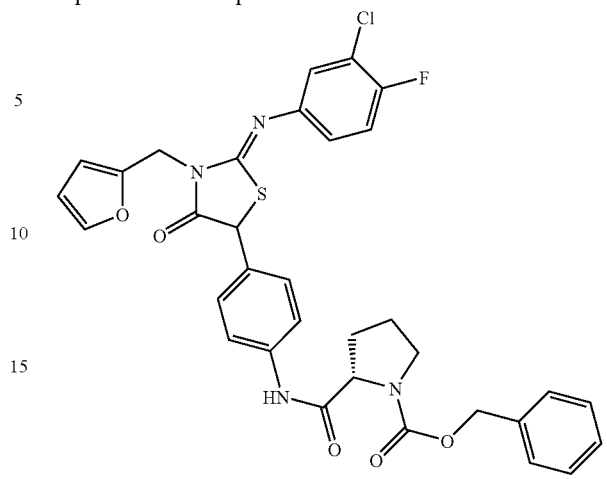
MS(ESI) m/z=647.1 (MH⁺); HPLC rt 2.06 min; Purity (99%).
Preparation of Compound 52
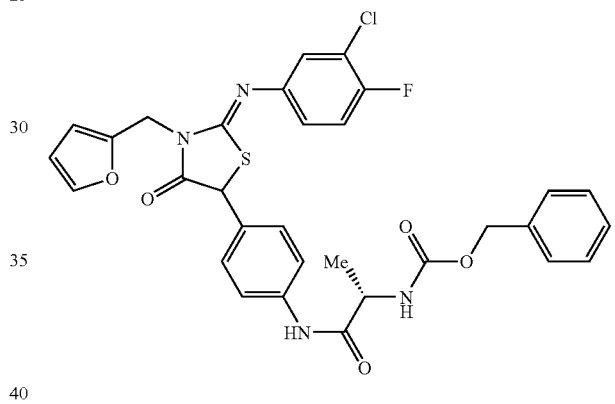
MS(ESI) m/z=621.2 (MH⁺); HPLC rt 1.97 min; Purity (95%).
Preparation of Compound 53
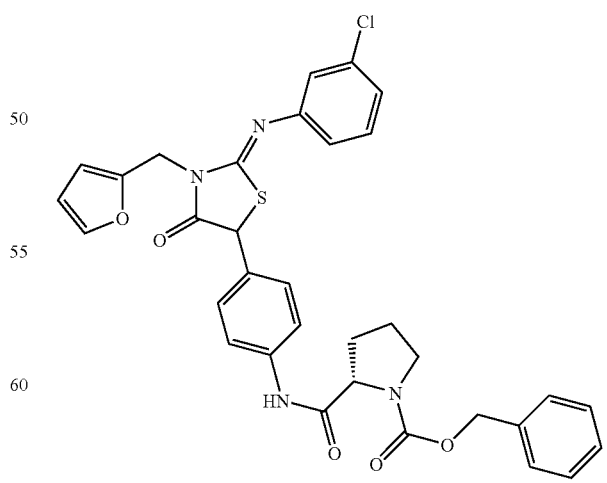
MS(ESI) m/z=629.2 (MH⁺); HPLC rt 1.98 min; Purity (98%).

Preparation of Compound 54
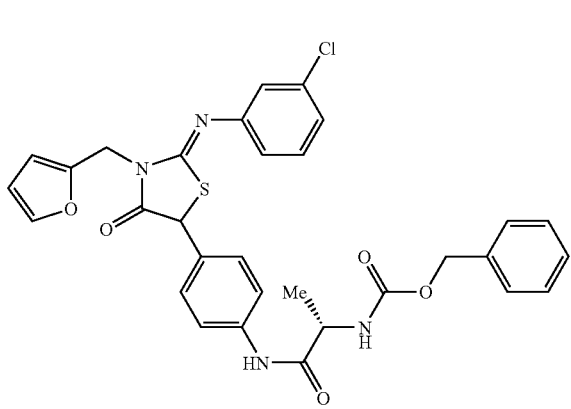
MS(ESI) m/z=603.2 (MH+); HPLC rt 1.96 min; Purity (98%).
Preparation of Compound 55
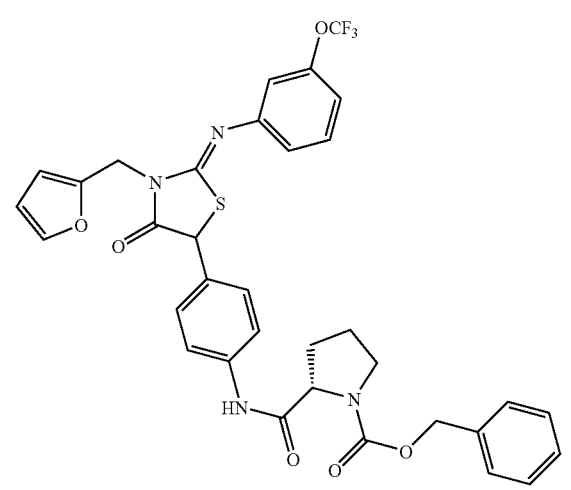
MS(ESI) m/z=679.2 (MH+); HPLC rt 1.99 min; Purity (99%).
Preparation of Compound 56
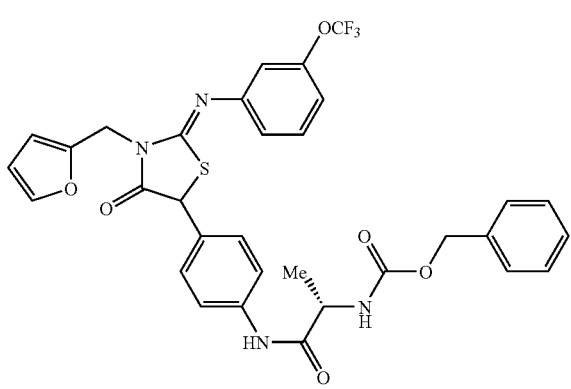
MS(ESI) m/z=653.1 (MH+); HPLC rt 1.97 min; Purity (>96%).
Preparation of Compound 57
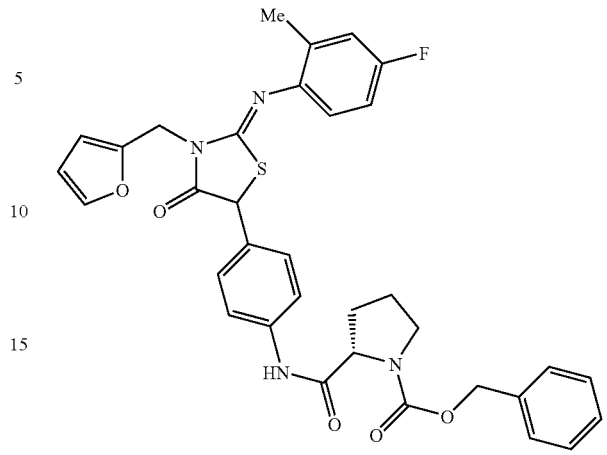
MS(ESI) m/z=627.2 (MH+); HPLC rt 2.02 min; Purity (99%).
Preparation of Compound 58
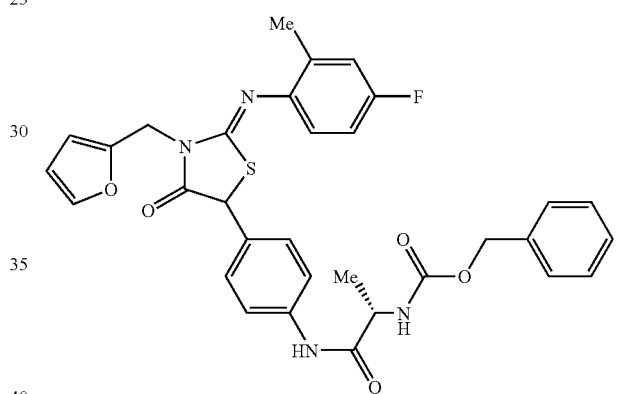
MS(ESI) m/z=601.22 (MH+); HPLC rt 2.01 min; Purity (99%).
Preparation of Compound 59
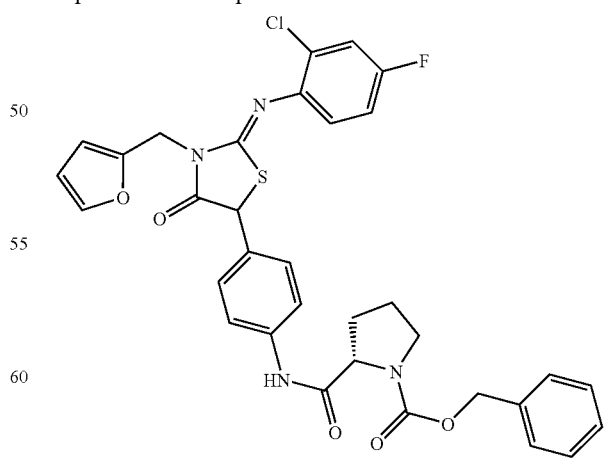
MS(ESI) m/z=647.3 (MH+); HPLC rt 2.12 min; Purity (95%).

Preparation of Compound 60
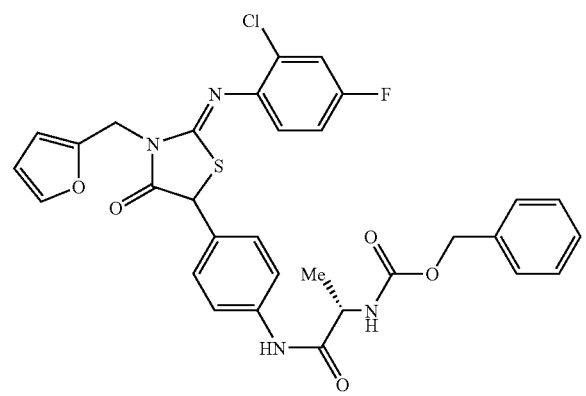
MS(ESI) m/z=621.3 (MH+); HPLC rt 1.95 min; Purity (97%).
Preparation of Compound 61
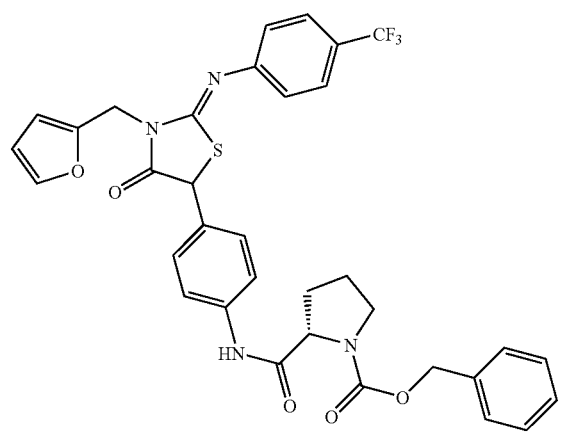
MS(ESI) m/z=623.4 (MH+); HPLC rt 2.01 min; Purity (97%).
Preparation of Compound 62
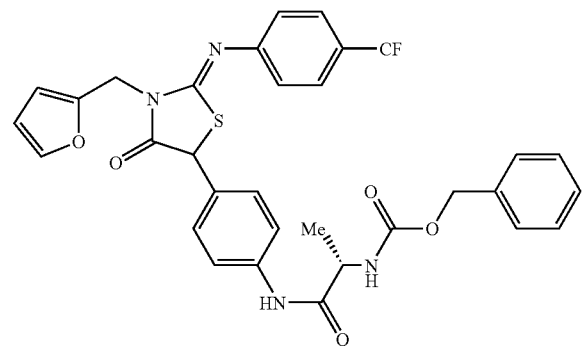
MS(ESI) m/z=637.15 (MH+); HPLC rt 2.05 min; Purity (97%).
Preparation of Compound 63
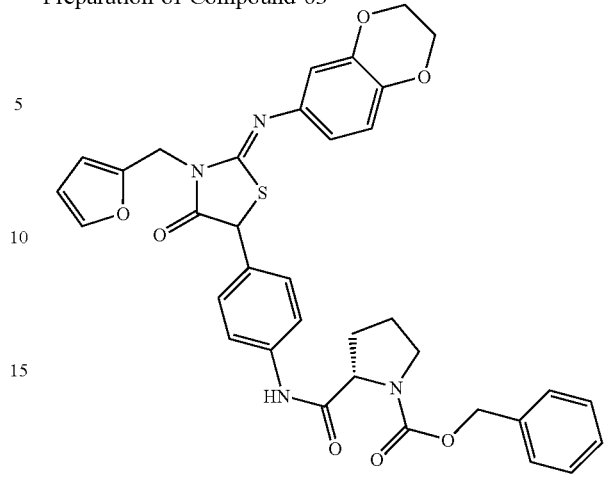
MS(ESI) m/z=653.4 (MH+); HPLC rt 1.85 min; Purity (98%).
Preparation of Compound 64
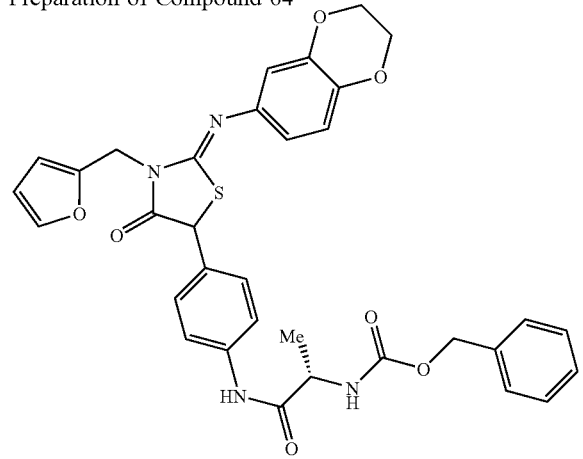
MS(ESI) m/z=627.2 (MH+); HPLC rt 1.95 min; Purity (98%).
Preparation of Compound 65
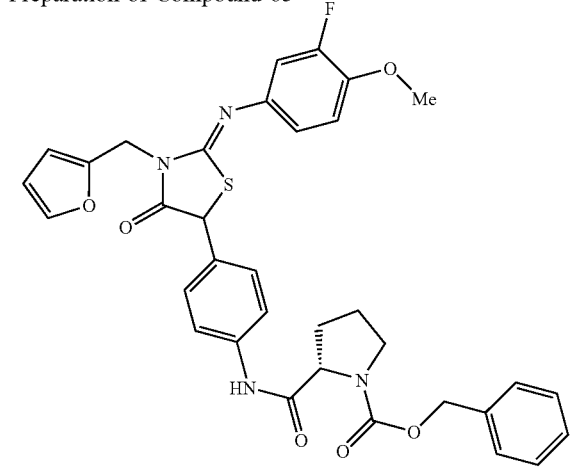
MS(ESI) m/z=643.2 (MH+); HPLC rt 1.95 min; Purity (98%).

Preparation of Compound 66

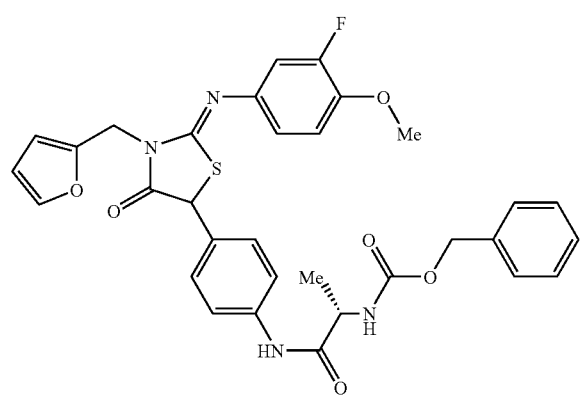

MS(ESI) m/z=617.2 (MH+); HPLC rt 1.89 min; Purity (98%).

Preparation of Compound 67

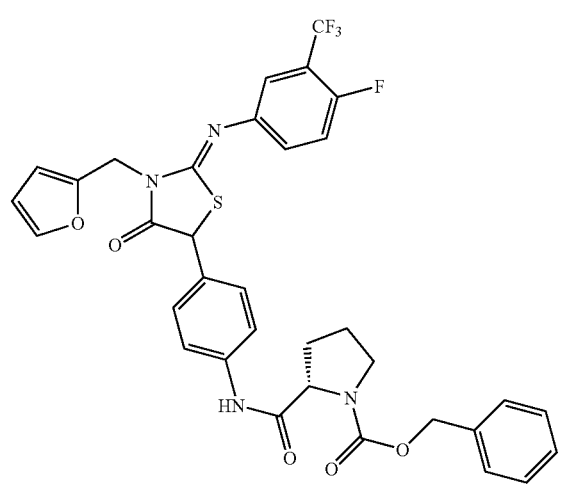

MS(ESI) m/z=681.1 (MH+); HPLC rt 1.98 min; Purity (98%).

Preparation of Compound 68

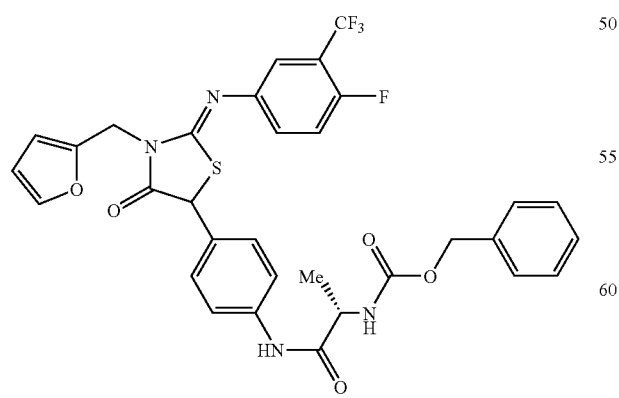

MS(ESI) m/z=655.1 (MH+); HPLC rt 2.05 min; Purity (98%).

General Synthetic Scheme 2

General synthetic scheme 2 provides another method to prepare the iminothiazolidinone ring system based upon an ipso type substitution (step 5a) to give intermediate B'. Intermediate A of General synthetic scheme 1 can be treated with ethyl bromoacetate to give intermediate E, an unsubstituted iminothiazolidinone. Alternatively, intermediate E can also be obtained upon treatment of intermediate D with a mercury reagent and an amine. Substitution via an ipso type reaction on 4-fluoronitrobenzene gives intermediate B' which upon reduction of the nitro group, step 3a', gives the same intermediate C of general synthetic scheme 1.

General Synthetic Scheme 2

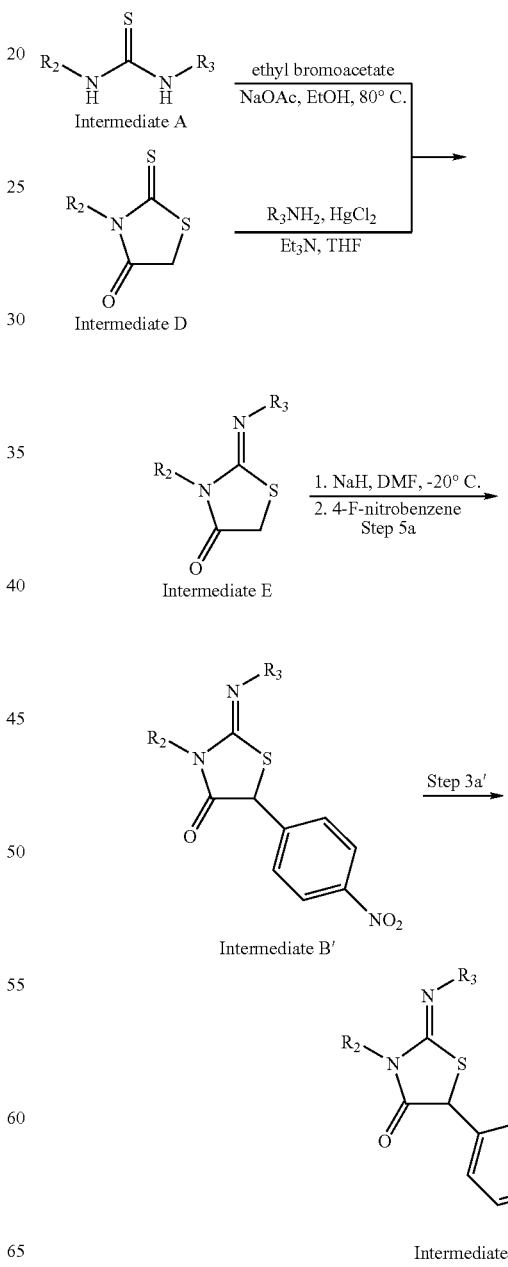

Specific Synthesis via Intermediate E

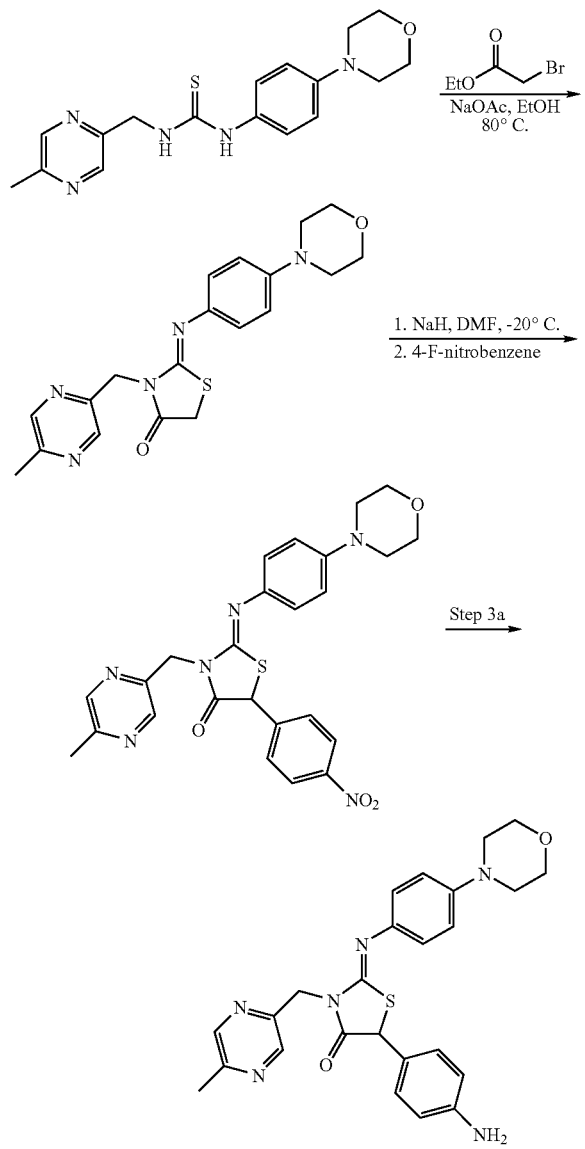

Preparation of Intermediate E (General Synthetic Scheme 2)

3-(5-Methylpyrazin-2-ylmethyl)-2-(4-morpholin-4-ylphenylimino)-thiazolidin-4-one A suspension of 1-(5-Methylpyrazin-2-ylmethyl)-3-(4-morpholin-4-ylphenyl)-thiourea (1.7 g, 5.0 mmol, 1.0 equiv) and NaOAc (0.82 g, 10.0 mmol, 2.0 equiv) in 30 mL ethanol was treated with ethyl bromoacetate (0.55 ml, 5.0 mmol, 1.0 equiv) as a neat liquid via syringe. The heterogeneous mixture was heated to 80° C. overnight. The solvent was removed in vacuo, and the residue was partitioned between EtOAc and saturated NaHCO₃. After drying the organic layer with brine and Na2SO4, the product was purified by flash chromatography (40 to 90% EtOAc in hexanes) to afford 1.4 g (73%) of the title compound as a yellow-orange foam: 1H NMR (500 MHz, CDCl3) δ 8.53 (d, 1H, J=1.5 Hz), 8.39 (d, 1H, J=1.5 Hz), 6.85 (s, 4H), 5.15 (s, 2H), 3.90 (s, 2H), 3.85 (m, 4H), 3.12 (m, 4H), 2.54 (s, 3H); MS (ESI) m/z=384.2 (MH⁺).

Preparation of Intermediate B' (Synthetic Scheme 2)

3-(5-Methylpyrazin-2-ylmethyl)-2-(4-morpholin-4-ylphenylimino)-5-(4-nitrophenyl)thiazolidin-4-one A solution of intermediate E (1.0 g, 2.71 mmol) in DMF (5 ml) was added via cannula into a −30° C. suspension of NaH (0.24 g, 6.0 mmol, 2.2 equiv) in DMF (10 mL) under nitrogen. After 15 min at −30° C., a solution of 4-fluoronitrobenzene (0.35 ml, 3.25 mmol, 1.2 equiv) in DMF (3 ml) was added dropwise which afforded a deep blue solution. The cold bath was removed and the mixture was warmed to room temperature overnight. The reaction mixture was quenched with saturated ammonium chloride solution and then extracted with EtOAc. Flash chromatography on silica gel (gradient elution from 40% EtOAc/hexanes to 80% EtOAc/hexanes) afforded the title compound (0.60 g, 44%) as a reddish-brown foam: 1H NMR (500 MHz, CD3CN) δ 8.60–8.58 (m, 1H), 8.51 (m, 1H), 8.27 (d, J=8.9 Hz, 2H), 7.77 (d, J=8.9 Hz, 2H), 7.32 (d, J=9.2 Hz, 2H), 6.98 (d, J=8.9 Hz, 2H), 5.59 (s, 1H), 5.18 (s, 2H), 3.95–3.93 (m, 4H), 3.39–3.36 (m, 4H), 2.55 (2s, 3H); MS (ESI) m/z=505.1 (MH+); HPLC rt 1.28 min.; Purity (92%).

Preparation of Intermediate C (Synthetic Scheme 2)

5-(4-Aminophenyl)-3-(5-methylpyrazin-2-ylmethyl)-2-(4-morpholin-4-yl-phenylimino)thiazolidin-4-one Tin(II) chloride dihydrate (0.40 g, 1.79 mmol, 3.0 equiv) was added in one portion to a solution of intermediate B' (0.50 g, 1.03 mmol) in ethyl acetate (10 ml) at room temperature under nitrogen. The mixture was heated to 75° C. for 4 h before it was cooled to room temperature, diluted with ethyl acetate (20 ml) and filtered though Celite. The filtrate was washed with saturated sodium bicarbonate solution and brine prior to drying and solvent evaporation. The title compound (0.52 g, 100%) was isolated as a tan foam which was used without further purification: 1H NMR (500 MHz, CD3CN) δ 12.1–10.1 (v br m, 4H), 8.59 (s, 1H), 8.52 (s, 1H), 7.52 (d, J=8.6 Hz, 2H), 7.26 (d, J=8.6 Hz, 2H), 6.96 (d, J=8.9 Hz, 2H), 6.81 (d, J=8.9 Hz, 2H), 5.78 (s, 1H), 5.17–5.10 (m, 2H), 3.74–3.72 (m, 4H), 3.10–3.08 (m, 4H), 2.49 (s, 3H); MS (ESI) m/z=475.1 (MH+); HPLC rt 0.75 min.; Purity (99%).

Compounds 69–92 were prepared according to General Synthetic Scheme 2, then completed according to General Synthetic Scheme 1 using Step 4a or Alternate Resin Coupling Step 4a.

Preparation of Compound 69

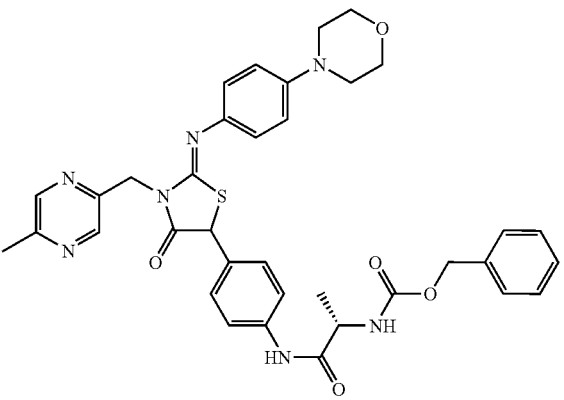

MS(ESI) m/z=680.2 (MH⁺); HPLC rt 1.26 min; Purity (99%).

Preparation of Compound 70

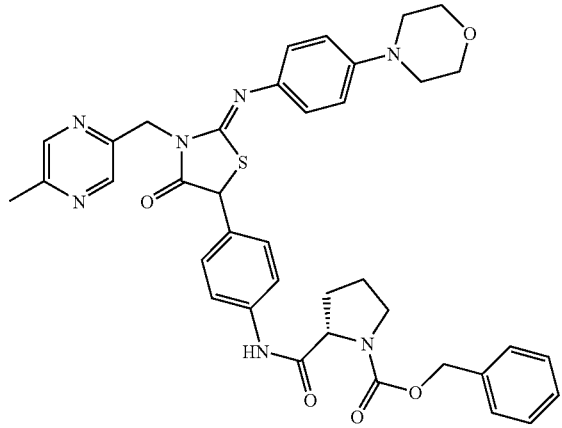

MS(ESI) m/z=706.2 (MH+); HPLC rt 1.29 min; Purity (99%).

Preparation of Compound 71

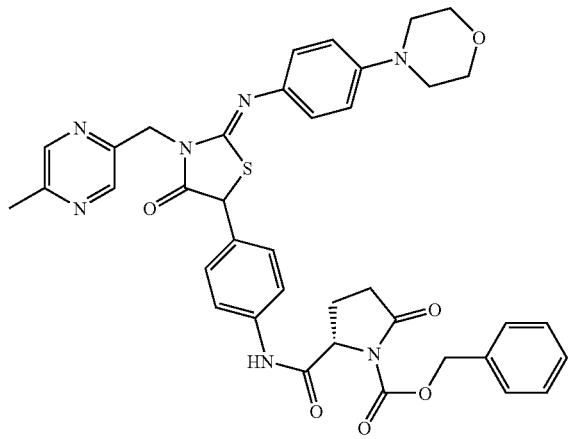

MS(ESI) m/z=720.1 (MH+); HPLC rt 1.90 min (3 min. grad.); Purity (91.5%).

Preparation of Compound 72

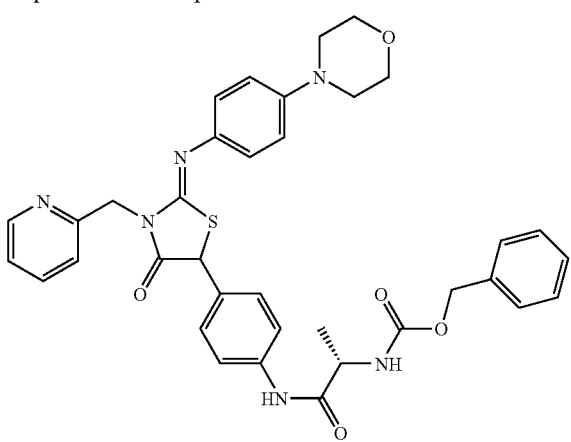

MS(ESI) m/z=665.3 (MH+); HPLC rt 1.21 min; Purity (99%).

Compound 72(c)—For comparison purposes, a D-alanine analog of compound 72 wherein the methyl group has an R configuration was prepared following the general procedure for the preparation of compound 72.

Preparation of Compound 73

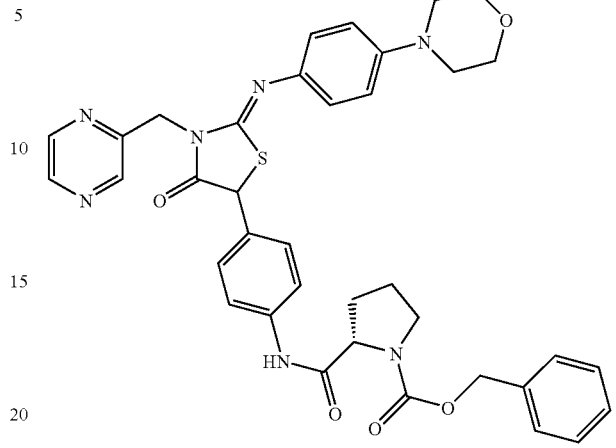

MS(ESI) m/z=691.3 (MH+); HPLC rt 1.23 min; Purity (99%).

Preparation of Compound 74

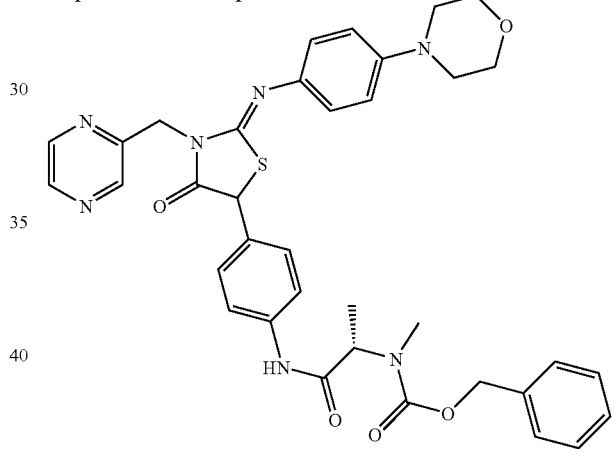

MS(ESI) m/z=679.4 (MH+); HPLC rt 1.26 min; Purity (99%).

Preparation of Compound 75

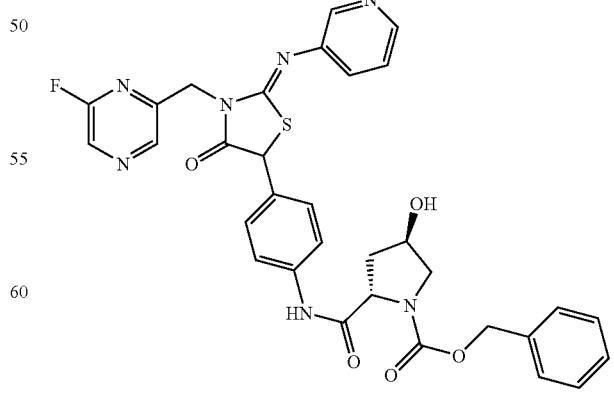

MS(ESI) m/z=640.3 (MH+); HPLC rt 1.36 min; Purity (98%).

Preparation of Compound 76
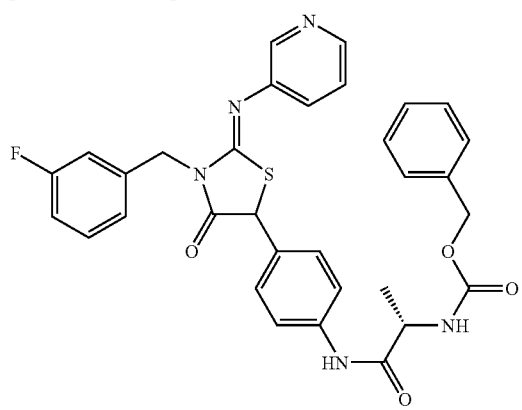
MS(ESI) m/z=598.2 (MH+); HPLC rt 1.32 min; Purity (99%).
Preparation of Compound 77
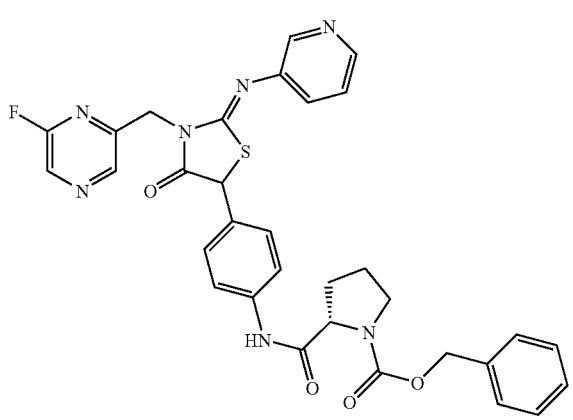
MS(ESI) m/z=624.3 (MH+); HPLC rt 1.34 min; Purity (99%).
Preparation of Compound 78
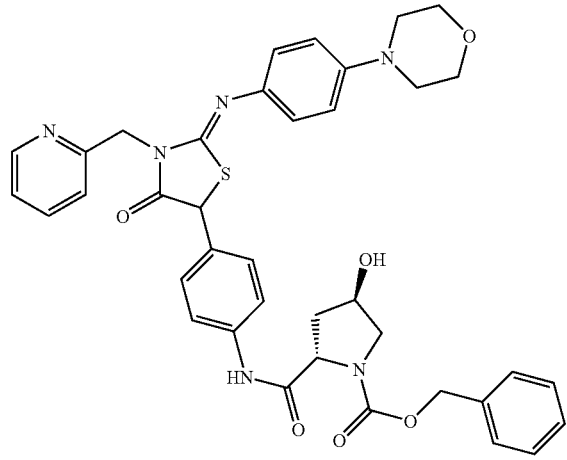
MS(ESI) m/z=707.3 (MH+); HPLC rt 1.23 min; Purity (99%).
Preparation of Compound 79
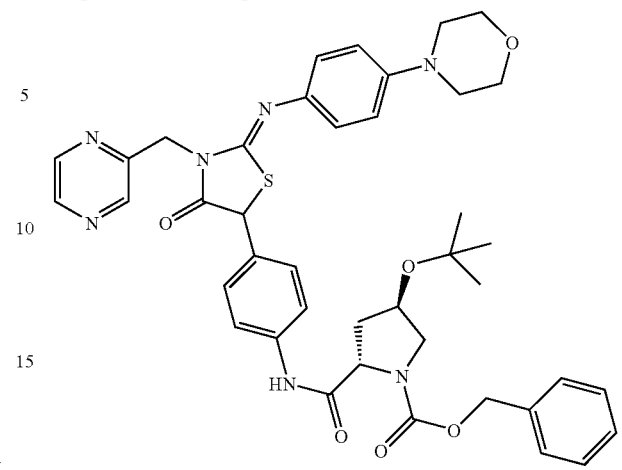
MS(ESI) m/z=763.3 (MH+); HPLC rt 1.41 min; Purity (99%).
Preparation of Compound 80
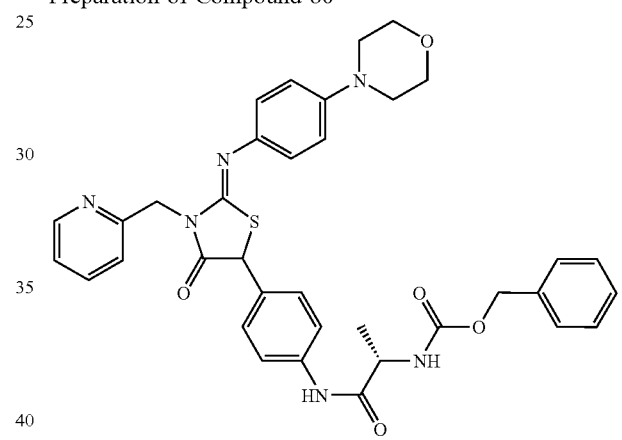
MS(ESI) m/z=665.2 (MH+); HPLC rt 1.19 min; Purity (99%).
Preparation of Compound 81
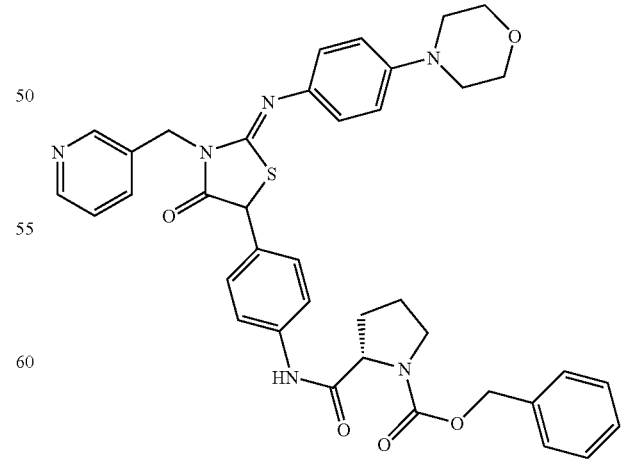
MS(ESI) m/z=691.2 (MH+); HPLC rt 1.21 min; Purity (99%).

Preparation of Compound 82

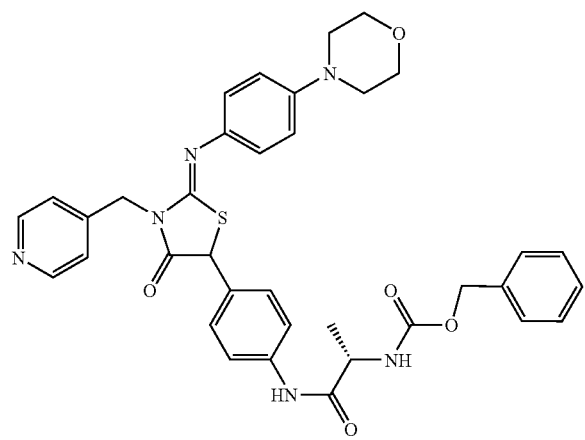

MS(ESI) m/z=665.2 (MH+); HPLC rt 1.18 min; Purity (99%).

Preparation of Compound 83

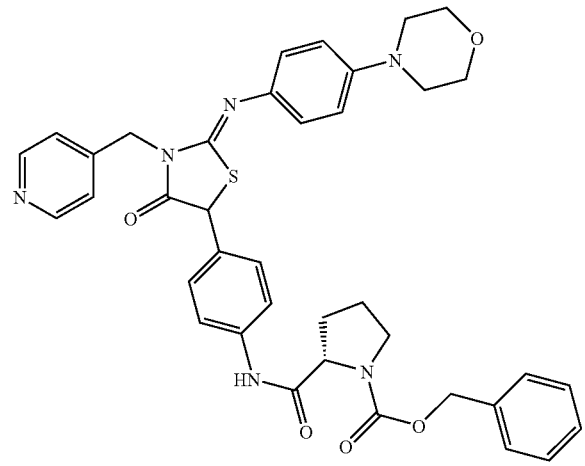

MS(ESI) m/z=691.2 (MH+); HPLC rt 1.20 min; Purity (95%).

Preparation of Compound 84

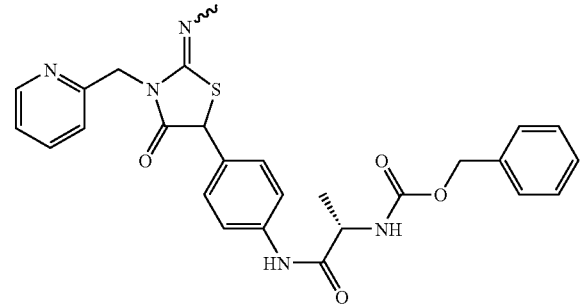

MS(ESI) m/z=518.1 (MH+); HPLC rt 1.67 and 1.94 min; Purity (99%).

Preparation of Compound 85

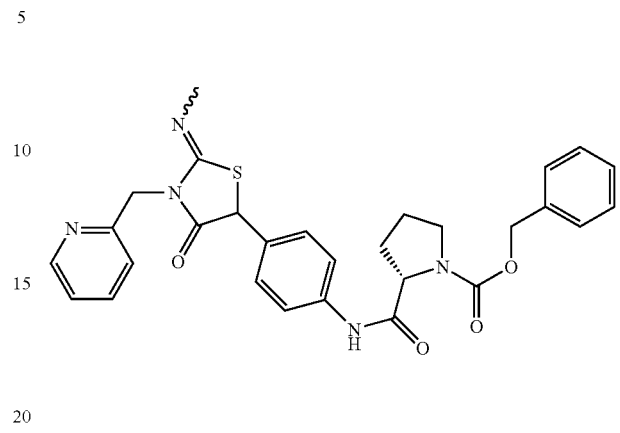

MS(ESI) m/z=544.2 (MH+); HPLC rt 1.05 and 1.17 min; Purity (99%).

Preparation of Compound 86

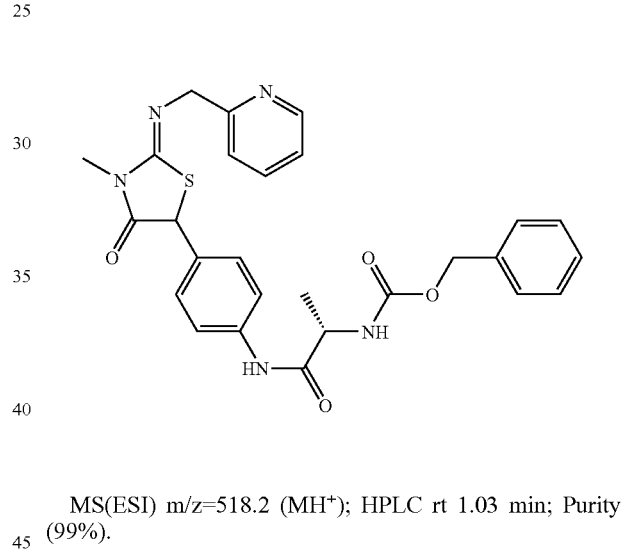

MS(ESI) m/z=518.2 (MH+); HPLC rt 1.03 min; Purity (99%).

Preparation of Compound 87

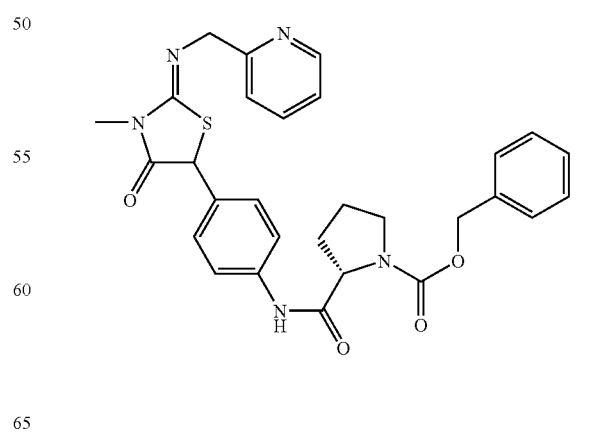

MS(ESI) m/z=544.2 (MH+); HPLC rt 1.07 min; Purity (99%).

Preparation of Compound 88

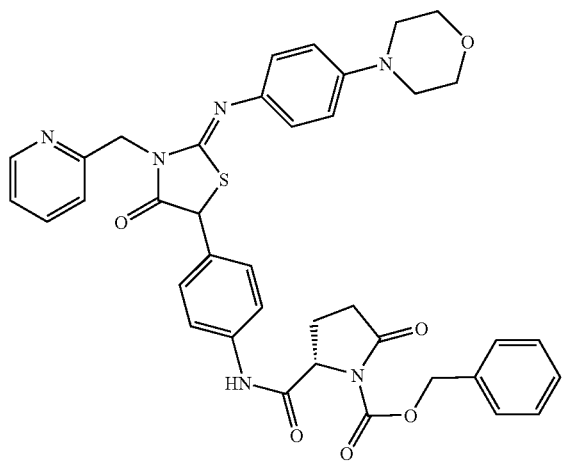

MS(ESI) m/z=704.7 (MH+); HPLC rt 1.72 min (3 min. grad.); Purity (94.5%).

Preparation of Compound 89

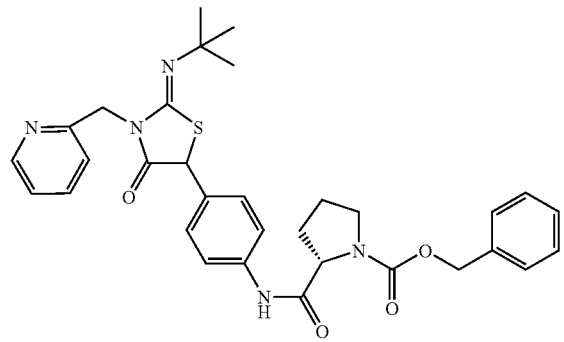

MS(ESI) m/z=586.4 (MH+); HPLC rt 1.57; Purity (95%).

Preparation of Compound 90

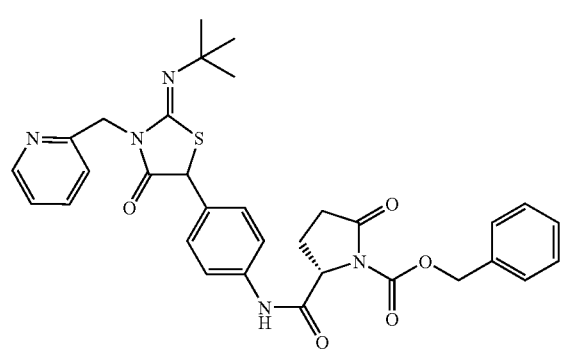

MS(ESI) m/z=601.2 (MH+); HPLC rt 1.35 min; Purity (90%).

Preparation of Compound 91

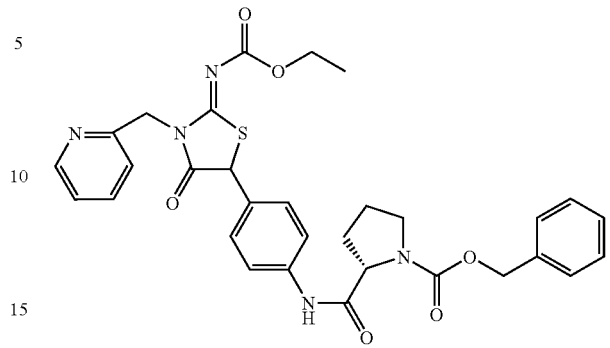

MS(ESI) m/z=602.3 (MH+); HPLC rt 2.01 min (3 min. grad.); Purity (97.3%).

Preparation of Compound 92

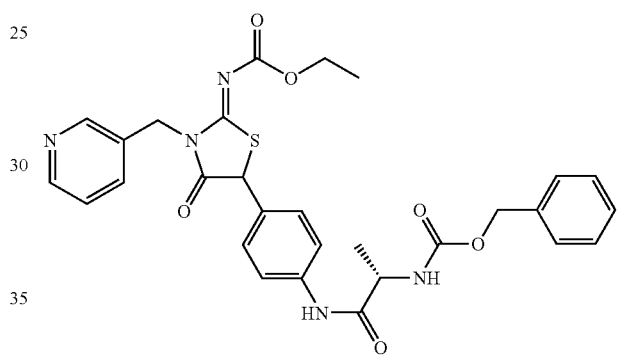

MS(ESI) m/z=576.2 (MH+); HPLC rt 1.97 min (3 min. grad.); Purity (98%).

Specific Synthesis via Intermediate D

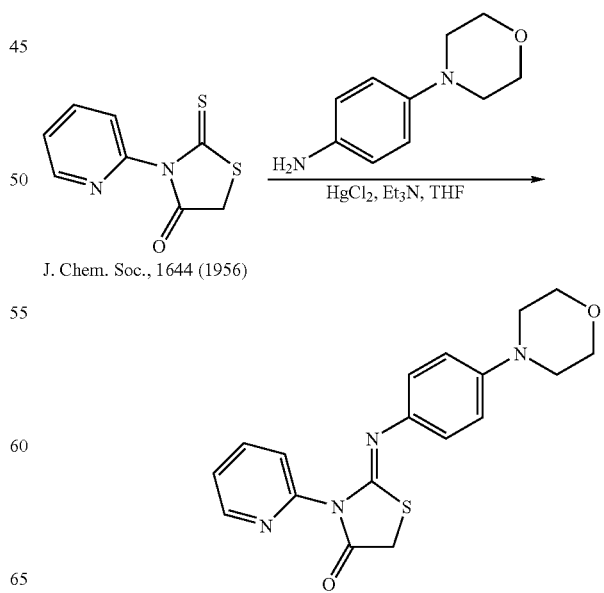

J. Chem. Soc., 1644 (1956)

2-(4-Morpholin-4-yl-phenylimino)-3-pyridin-2-yl-thiazolidin-4-one 3-(2-pyridyl)-2-thioxo-thiazolidin-4-one (1.1 g, 5.3 mmol, 1.0 equiv), prepared as described in J. Chem. Soc. (1956) 1644, was dissolved in 30 ml THF and charged with 4-morpholin-4-yl aniline (0.94 g, 5.28 mmol, 1.0 equiv) and Et$_3$N (1.47 ml, 10.6 mmol, 2.0 equiv). Mercury (II) chloride (1.4 g, 5.28 mmol, 1.0 equiv) was added in one portion as a solid, and the heterogeneous mixture was stirred at ambient temperature overnight. The reaction mixture was filtered through Celite, and the filtrate was partitioned between EtOAc and saturated NH$_4$Cl. The organic layer was washed with brine, dried over Na2SO4, and concentrated in vacuo. Flash chromatography (40% to 100% EtOAc in hexanes, silica) afforded 0.83 g (44%) of the title compound: 1H NMR (300 MHz, CDCl3) δ 8.70 (m, 1H), 7.90 (m, 1H), 7.37–7.44 (m, 2H), 3.99 (s, 2H), 3.84 (m, 4H), 3.11 (m, 4H); MS (ESI) m/z=355.3 (MH$^+$).

Compounds 93–94 were prepared according to specific synthes Scheme D and completed using General Synthesis Scheme 2 and Step 4a or Alternate Resin Coupling Step 4a of General Synthesis Scheme 1.

Preparation of Compound 93

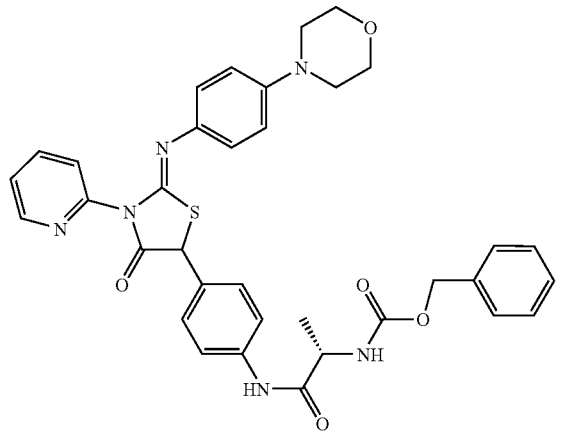

MS(ESI) m/z=651.2 (MH$^+$); HPLC rt 1.29 min; Purity (99%).

Preparation of Compound 94

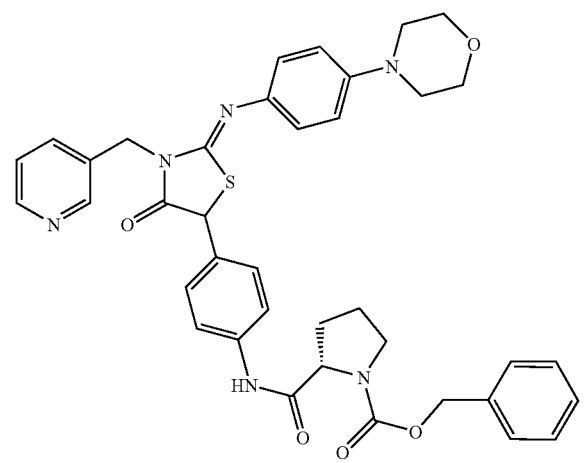

MS(ESI) m/z=677.5 (MH$^+$); HPLC rt 1.30 min; Purity (99%).

Continuation in General Synthetic Scheme 1

A continuation in the general synthetic scheme 1 depicts the method of preparation for compounds derived from intermediate G, or the proline amino acid analog thereof. The N-Boc protecting group was removed in the presence of trifluoroacetic acid to give the salt, intermediate F, which was converted to the free base intermediate G. Treatment of intermediate G with various acylating agents gave amide derivatives, or treatment of intermediate G with isocyanates/isothiocyanates gave urea/thiourea derivatives as described below.

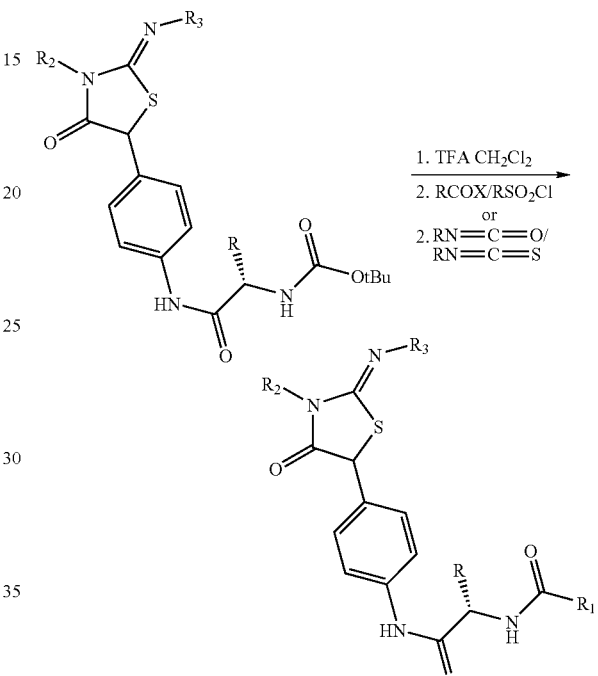

Preparation of Intermediate F

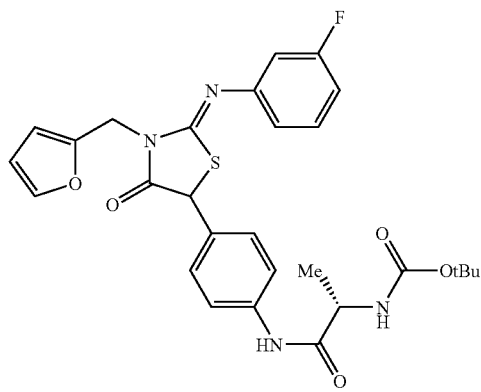

(1S-{4-[2-(3-Fluorophenylimino)-3-furan-2-ylmethyl-4-oxo-thiazolidin-5-yl]-phenylcarbamoyl}ethyl)carbamic acid tert-butyl ester. The product was prepared by coupling procedure described above upon reaction of 5-(4-aminophenyl)-2-(3-fluorophenylimino)-3-furan-2-ylmethyl-thiazolidin-4-one (437 mg, 1.15 mmol) with N-Boc-L-alanine (540 mg, 2.85 mmol) in anhydrous dichloromethane (50 ml). Silica gel chromatography (ISCO: 10 g SiO$_2$, CH$_2$Cl$_2$ to 10% EtOAc/CH$_2$Cl$_2$ gradient) gave 409 mg (62%); HPLC rt 1.84 min; Purity (86.6%); MS (ESI) m/z=553.2 (MH$^+$).

Preparation of Intermediate G

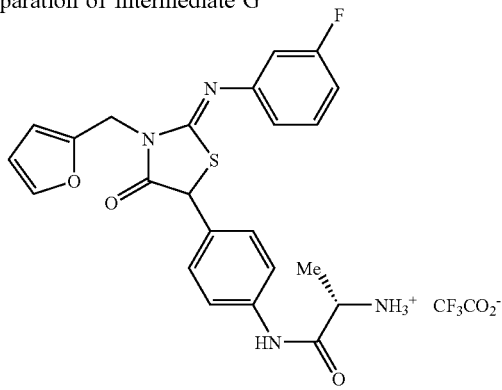

2S-amino-N-{4-[2-(3-fluorophenylimino)-3-furan-2yl-4-oxo-thiazolidin-5-yl]phenyl}propionamide, Trifluoroacetic acid salt (1S-{4-[2-(3-Fluorophenylimino)-3-furan-2-ylmethyl-4-oxo-thiazolidin-5-yl]-phenylcarbamoyl}ethyl)-carbamic acid tert-butyl ester (413 mg, 0.75 mmol) was dissolved in dichloromethane (50 ml) under nitrogen and 5 ml of trifluoroacetic acid added slowly over 2 min. The reaction was stirred 3 h, volatiles were removed in vacuo to give 486 mg (crude) HPLC rt 1.51 min; Purity (88.4%). Purification of a 30 mg sample by reverse phase HPLC gave a pure sample: $^1$H NMR (300 MHz) (CD3CN) δ 1.56 (d, J=7.0 Hz, 3H); 4.15 (quad, J=7.0 Hz, 1H); 4.99 (s, 2H); 5.32 (s, 1H); 6.38–6.41 (m, 2H); 6.75 (dt, J=10.2 Hz, J=2.2 Hz, 1H); 6.79–6.83 (m, 1H); 6.91 (td, J=8.7 Hz, J=2.2 Hz, 1H); 7.31–7.60 (m, 9H) (includes broad baseline rise, presumably NH$_2$H$^+$); 9.10 (s, 1H); MS (ESI) m/z=453.2 (MH$^+$).

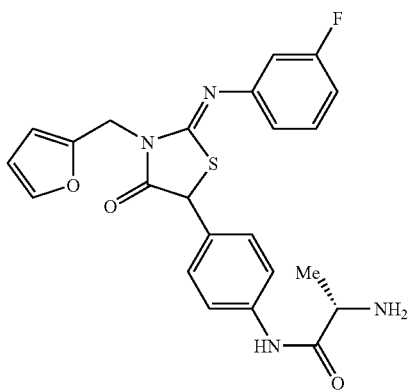

2S-amino-N-{4-[2-(3-fluorophenylimino)-3-furan-2yl-4-oxo-thiazolidin-5-yl]phenyl}propionamide, Free base. The free base form was obtained upon dissolving the trifluoroacetic acid salt in dichloromethane and eluting over excess anhydrous potassium carbonate. A stock solution (20 mg/ml) of the free amine was prepared by dissolving 250 mg free base in 12.5 ml of anhydrous dichloromethane.

Amide Formation Using Carbodiimide Resin/Carboxylic Acid Method: A 2 dram vial was charged with 0.09 mmol (2 equiv.) carboxylic acid dissolved in 1 ml anhydrous dichloromethane and N-cyclohexylcarbodiimide, N-methyl polystyrene resin (105 mg, 0.17 mmol) [Nova Biochem, loading 1.65 mMol/g]. The solution shaken (600 rpm) for a 2–5 min and 1.0 ml freebase stock solution (20 mg, 0.04 mmol) of 2S-amino-N-{4-[2-(3-fluorophenylimino)-3-furan-2yl-4-oxo-thiazolidin-5-yl]phenyl}propionamide was added. The reactions were capped and shaken for 18 h, filtered, and the resin rinsed with dichloromethane. Removal of volatiles in vacuo gave products which were purified by reverse phase preparative HPLC.

Compounds 95–122 were prepared according to the Continuation of General Synthesis Scheme 1/Amide Formation.

Preparation of Compound 95

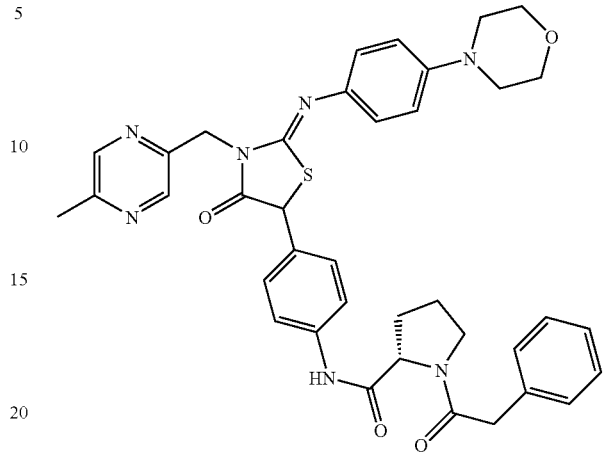

MS(ESI) m/z=690.2 (MH$^+$); HPLC rt 1.24 min; Purity (99%).

Preparation of Compound 96

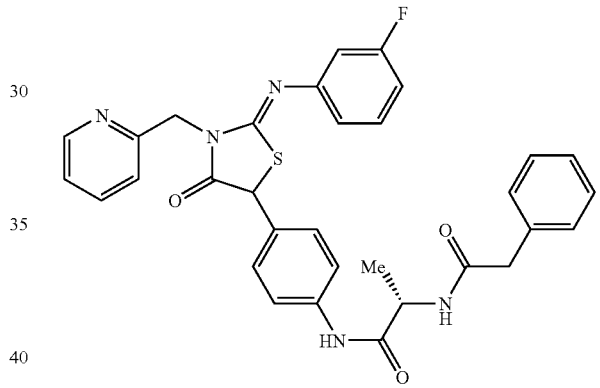

MS(ESI) m/z=581.9 (MH$^+$); HPLC rt 1.56 min; Purity (95%).

Preparation of Compound 97

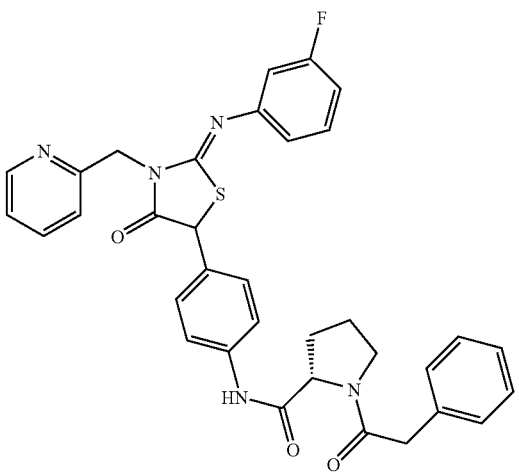

MS(ESI) m/z=607.9 (M<); HPLC rt 1.59 min; Purity (99%).

Preparation of Compound 98

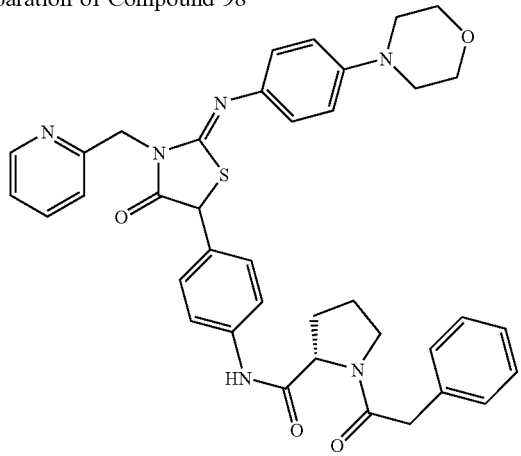

MS(ESI) m/z=675.3 (MH+); HPLC rt 1.17 min; Purity (99%).

Compound 98(c)—For comparison purposes, a D-proline analog of compound 98 where R and R' are joined with an R stereoconfiguration was also prepared following the general procedure for the preparation of compound 98.

Preparation of Compound 99

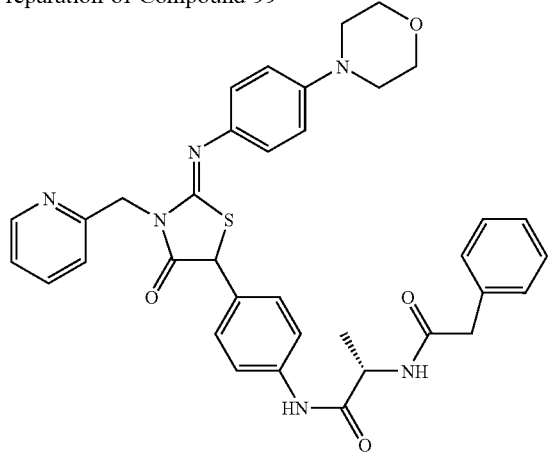

MS(ESI) m/z=649.3 (MH+); HPLC rt 1.15 min; Purity (99%).

Preparation of Compound 100

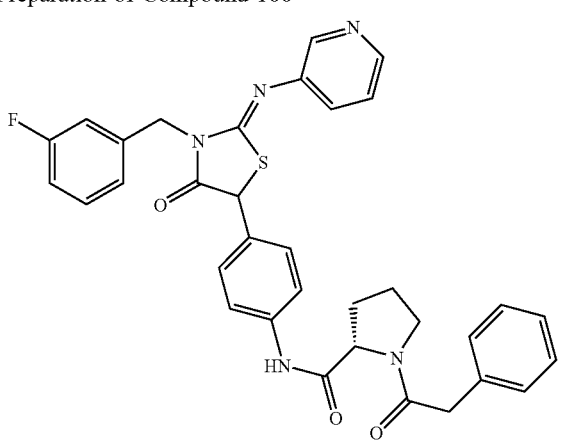

MS(ESI) m/z=608.3 (M+); HPLC rt 1.29 min; Purity (99%).

Preparation of Compound 101

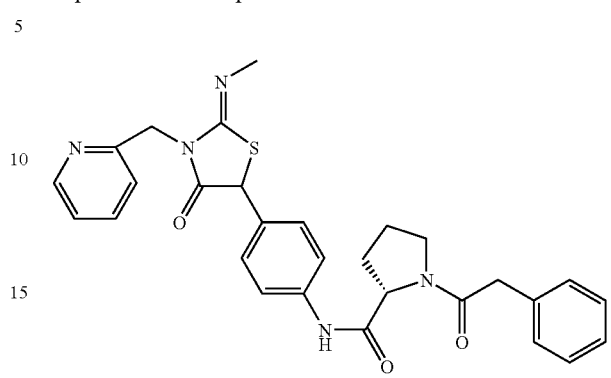

MS(ESI) m/z=528.2 (MH+); HPLC rt 1.02 min; Purity (88%).

Preparation of Compound 102

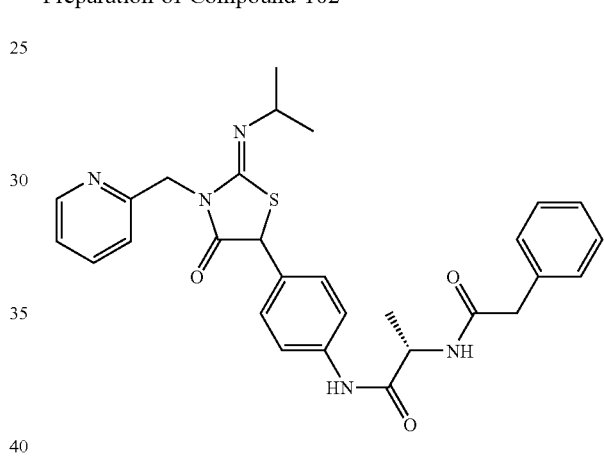

MS(ESI) m/z=530.3 (MH+); HPLC rt 3.04 min (3 min. grad.); Purity (99%).

Preparation of Compound 103

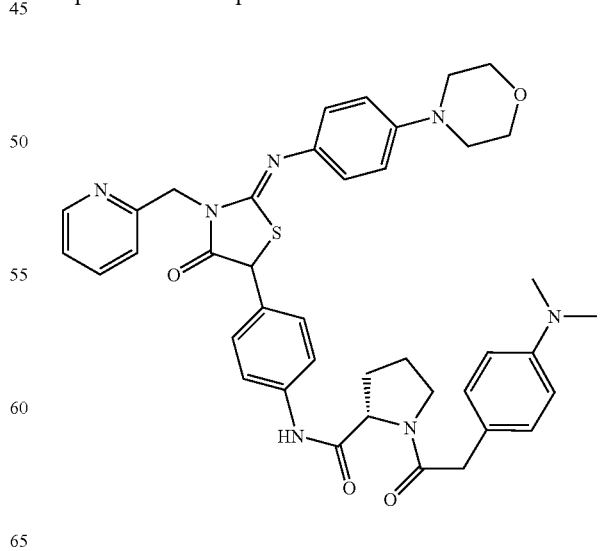

MS(ESI) m/z=718.2 (MH+); HPLC rt 0.91 min; Purity (99%).

Preparation of Compound 104
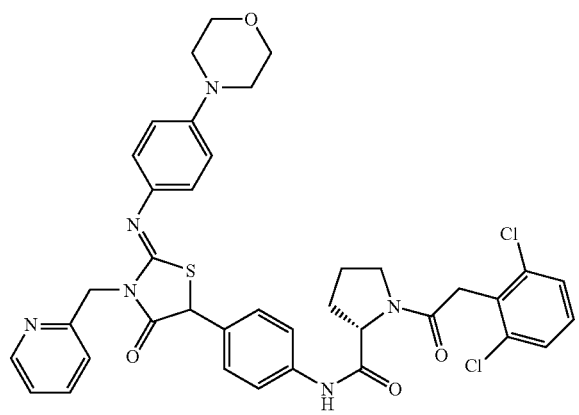
MS(ESI) m/z=743.3 (MH⁺); HPLC rt 1.24 min; Purity (99%).
Preparation of Compound 105
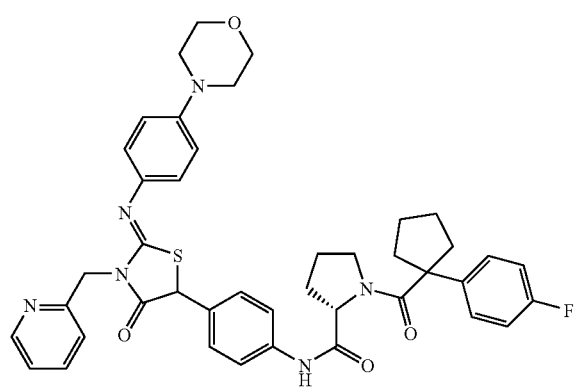
MS(ESI) m/z=747.3 (MH⁺); HPLC rt 1.39 min; Purity (99%).
Preparation of Compound 106
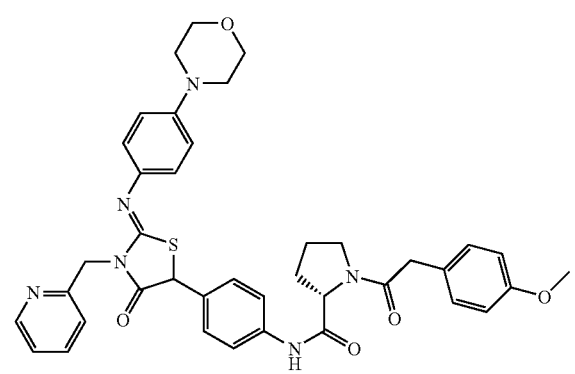
MS(ESI) m/z=705.4 (MH⁺); HPLC rt 1.12 min; Purity (99%).
Preparation of Compound 107
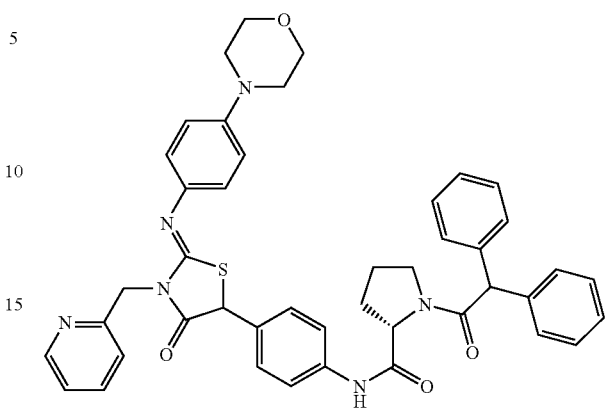
MS(ESI) m/z=751.4 (MH⁺); HPLC rt 1.32 min; Purity (99%).
Preparation of Compound 108
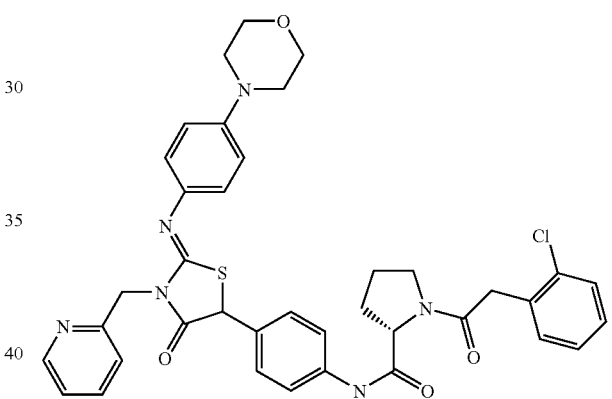
MS(ESI) m/z=709.2 (MH⁺); HPLC rt 1.36 min; Purity (99%).
Preparation of Compound 109
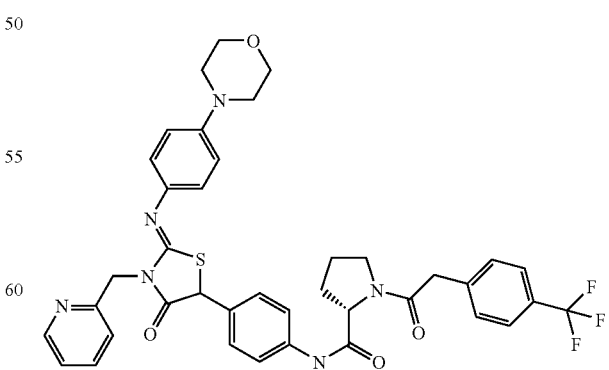
MS(ESI) m/z=743.3 (MH⁺); HPLC rt 1.46 min; Purity (99%).

Preparation of Compound 110
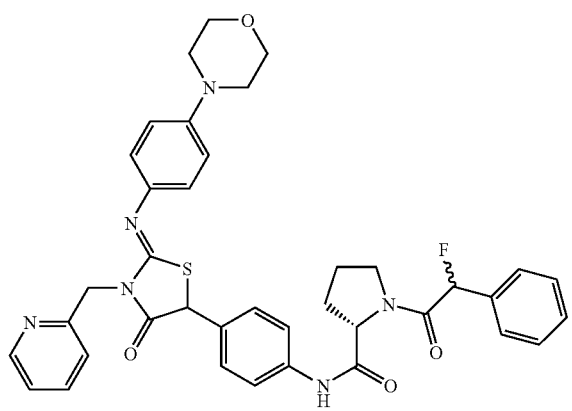
MS(ESI) m/z=693.3 (MH+); HPLC rt 1.17 min; Purity (99%).
Preparation of Compound 111
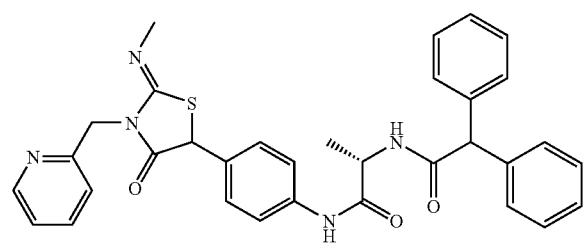
MS(ESI) m/z=578.1 (MH+); HPLC rt 1.98 and 2.09 min; Purity (99%).
Preparation of Compound 112
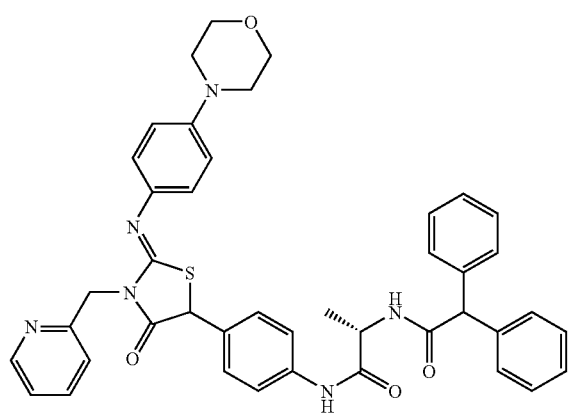
MS(ESI) m/z=725.2 (MH+); HPLC rt 1.91 min (3 min. grad.); Purity (99%).
Preparation of Compound 113
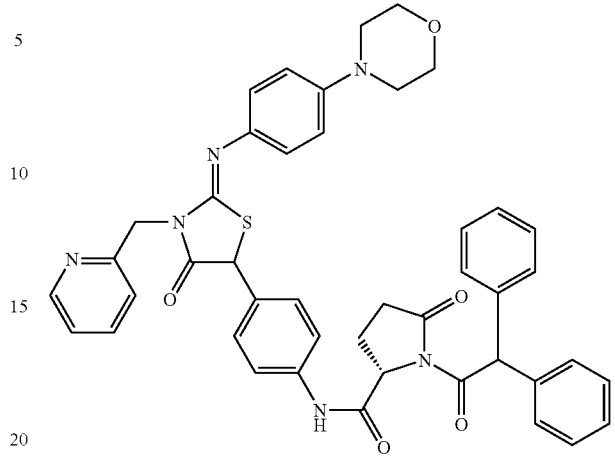
MS(ESI) m/z=765.3 (MH+); HPLC rt 2.01 min (3 min. grad.); Purity (98%).
Preparation of Compound 114
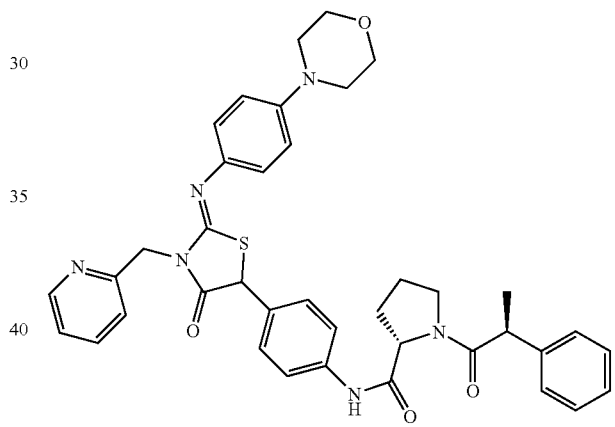
MS(ESI) m/z=689.3 (MH+); HPLC rt 1.82 min (3 min. grad.); Purity (98%).
Preparation of Compound 115
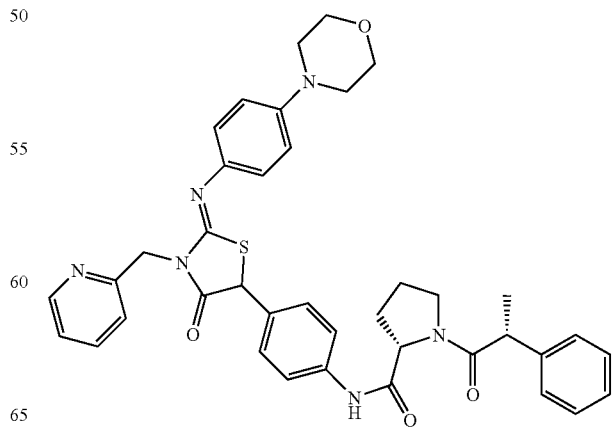

MS(ESI) m/z=689.3 (MH⁺); HPLC rt 1.82 min (3 min. grad.); Purity (99%).

Preparation of Compound 116

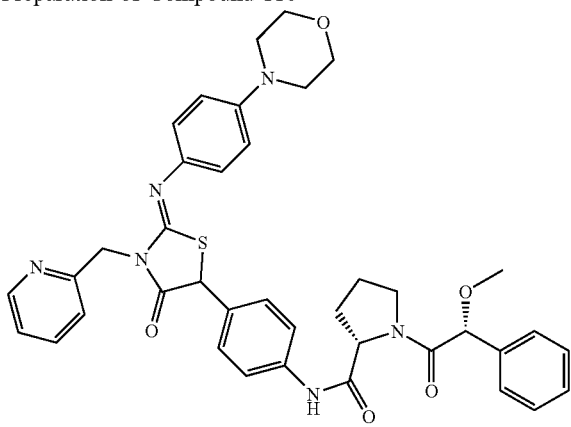

MS(ESI) m/z=705.3 (MH⁺); HPLC rt 1.67 min (3 min. grad.); Purity (99%).

Preparation of Compound 117

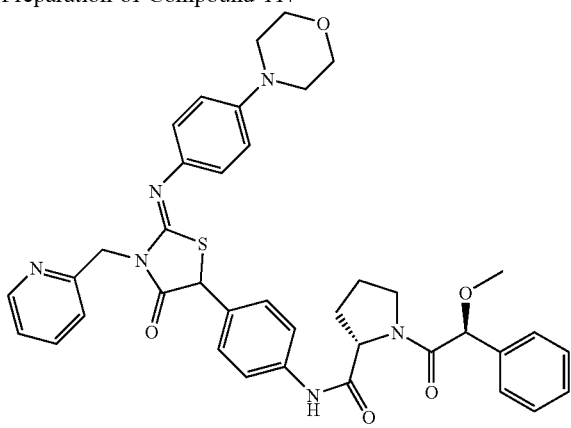

MS(ESI) m/z=705.3 (MH⁺); HPLC rt 1.70 min (3 min. grad.); Purity (99%).

Preparation of Compound 118

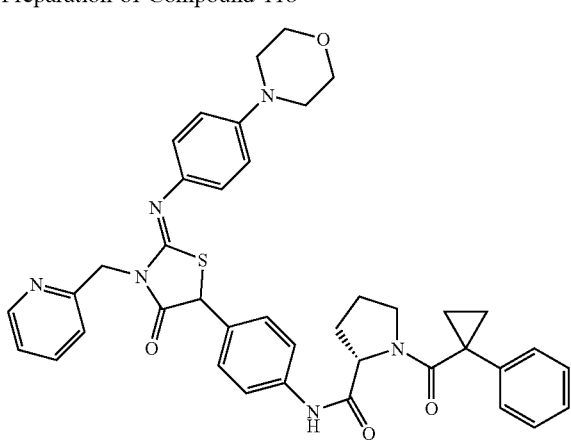

MS(ESI) m/z=701.3 (MH⁺); HPLC rt 1.86 min (3 min. grad.); Purity (99%).

Preparation of Compound 119

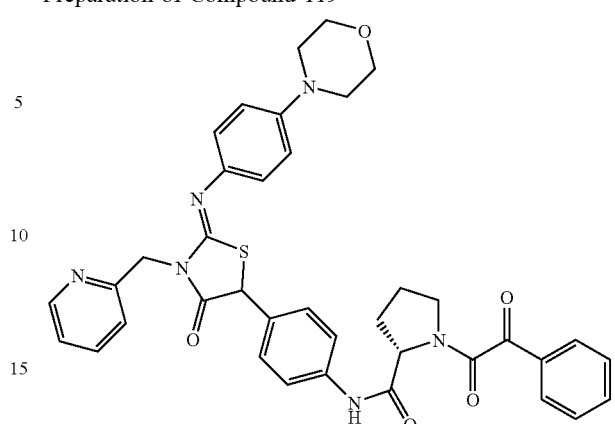

MS(ESI) m/z=689.3 (MH⁺); HPLC rt 1.72 (sh) & 1.75 min (3 min. grad.); Purity (99%).

Preparation of Compound 120

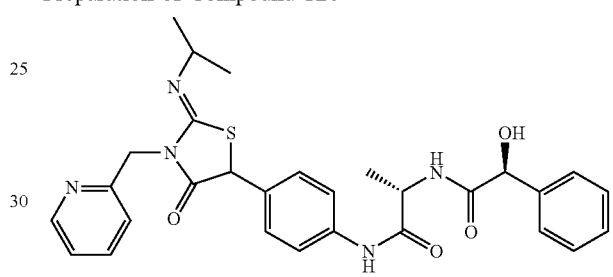

MS(ESI) m/z=546.3 (MH⁺); HPLC rt 3.02 min (3 min. grad.); Purity (99%).

Preparation of Compound 121

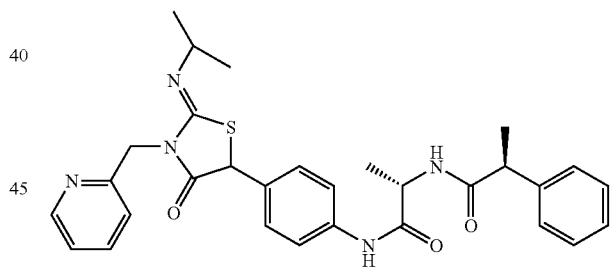

MS(ESI) m/z=544.3 (MH⁺); HPLC rt 3.12 min (3 min. grad.); Purity (95.2%).

Preparation of Compound 122

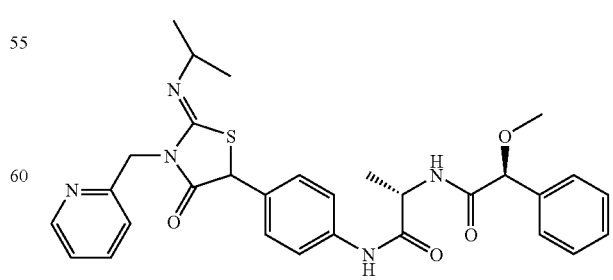

MS(ESI) m/z=560.3 (MH⁺); HPLC rt 3.14 min (3 min. grad.); Purity (91.4%).

Preparation of Compound 123

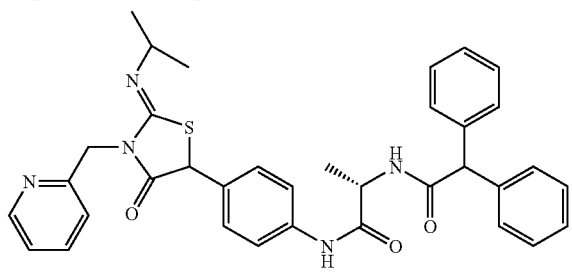

MS(ESI) m/z=606.3 (MH+); HPLC rt 3.20 min (3 min. grad.); Purity (98.5%).

Preparation of Compound 124

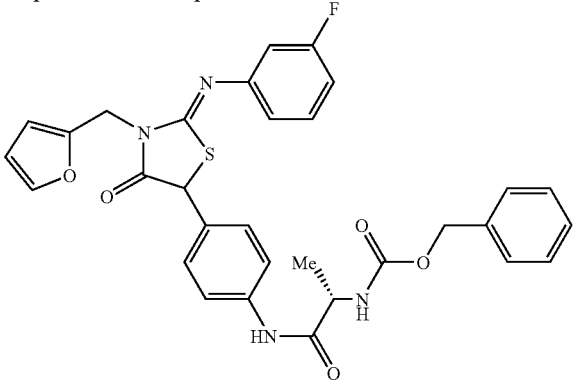

(N-{4-[2-(3-fluorophenylimino)-3-furan-2-ylmethyl-4-oxo-thiazolidin-5-yl]phenyl}-2S-(phenylacetylamino))propionamide. $^1$H NMR (300 MHz) (CD$_3$CN) δ 1.37 (d, J=7.0 Hz, 311); 3.56 (s, 2H); 4.43 (quint, J=7.0 Hz, 1H); 5.01 (s, 2H); 5.32 (s, 1H); 6.40–6.43 (m, 2H); 6.78 (dt, J=10.2 Hz, J=2.2 Hz, 1H); 6.83 (d, J=8.1 Hz, 1H); 6.92 (td, J=8.4, J=2.6, 1H); 7.01 (d, J=6.6 Hz, 1H); 7.24–7.43 (m, 8H); 7.48–7.52 (m, 3H); 8.69 (br.s, 1H); $^{13}$C NMR (75 MHz) (CD$_3$CN) δ 17.4 (CH$_3$), 39.8 (PhCH$_2$), 42.8 (Furan CH$_2$), 50.4 (CH-Ala), 51.4 (CH-thiazoline), 108.6 (J$_{CF}$=23.0 Hz), 109.1 (furan CH), 111.0 (furan CH), 111.5 (J$_{CF}$=21.3 Hz), 117.4 (J$_{CF}$=2.9 Hz), 120.3, 127.2, 128.9, 129.5 (J$_{CF}$=19.6 Hz), 131.3 (CH), 131.4 (CH), 131.6 (C quat.), 136.2 (C quat.), 139.3 (C quat.), 142.7 (furan CH), 149.8 (C quat. furan), 154.5 (C quat. imino), 171.5 (anilide C=O), 173.1 (thiazoline C=O) Some quaternary signals above 150 ppm are not resolved in S/N baseline. LC/MS (ESI) m/z=571.2 (MH+) High Resolution MS Calc: C$_{31}$H$_{27}$F$_1$N$_4$O$_4$S$_1$ [MH$^-$] 569.16588; Found: 569.1662; Dev: −0.5 ppm; HPLC rt 1.81 min; Purity (98%).

Preparation of Compound 125

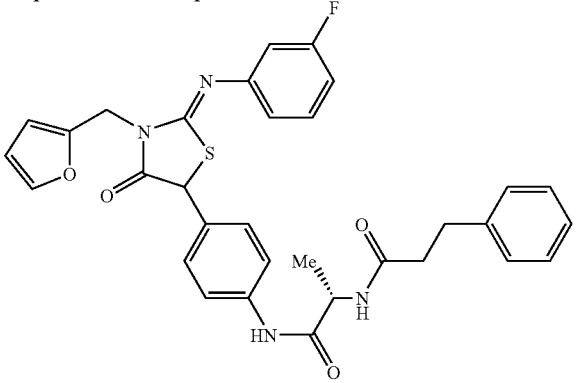

MS(ESI) m/z=585.3 (MH+); HPLC rt 1.75 min; Purity (96%).

Preparation of Compound 126

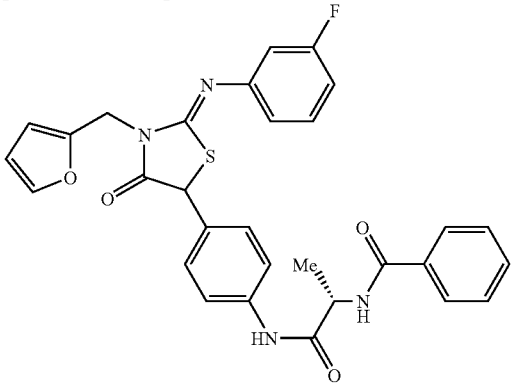

MS (ESI) m/z=557.2 (MH+); HPLC rt 1.85 min; Purity (>94%).

Preparation of Compound 127

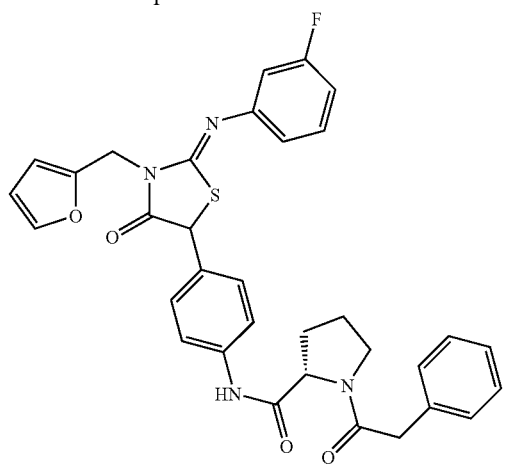

$^1$H NMR (300 MHz) δ: 1.78–1.86 (m, 1H); 1.97–2.18 (m, 2H); 2.49–2.55 (m, 3H, H$_2$O?); 3.45–3.63 (m, 2H); 3.73 (s, 2H); 4.78 (d, J=7.3 Hz, 1H); 4.99–5.06 (m, 2H); 5.11 (s, 1H); 6.33–6.39 (m, 2H); 6.70–6.85 (m, 3H); 7.17–7.37 (m, 9H); 7.46 (d, J=8.4 Hz, 2H); 9.66 (d, J=5.1 Hz, 1H); MS (ESI) m/z=595.09 (MH+); HPLC rt 1.21 min; Purity (98%).

Preparation of Compound 128

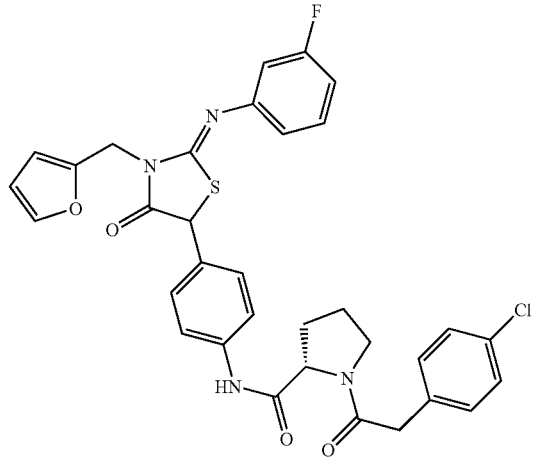

MS (ESI) m/z=632.2 (MH+); HPLC rt 1.31 min; Purity (97%).

Preparation of Compound 129

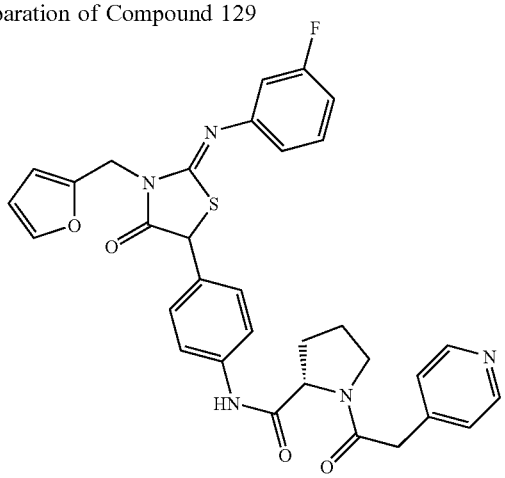

MS (ESI) m/z=598.3 (MH+); HPLC rt 0.68 min; Purity (94%).

Preparation of Compound 130

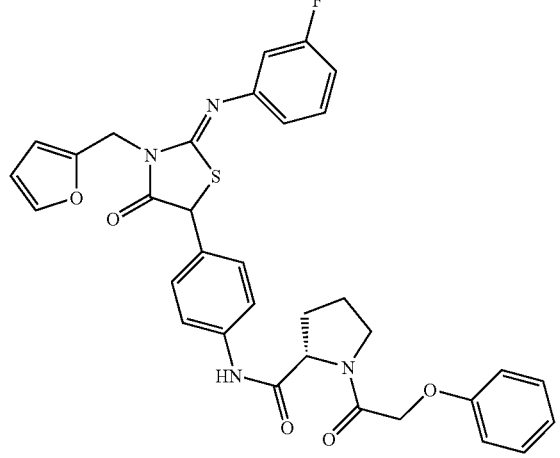

MS (ESI) m/z=613.3 (MH+); HPLC rt 1.19 min; Purity (97%).

Preparation of Compound 131

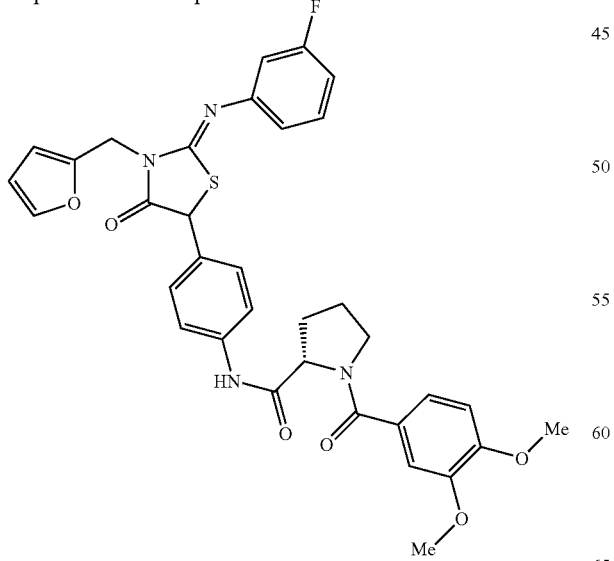

MS (ESI) m/z=657.3 (MH+); HPLC rt 1.10 min; Purity (98%).

Preparation of Compound 132

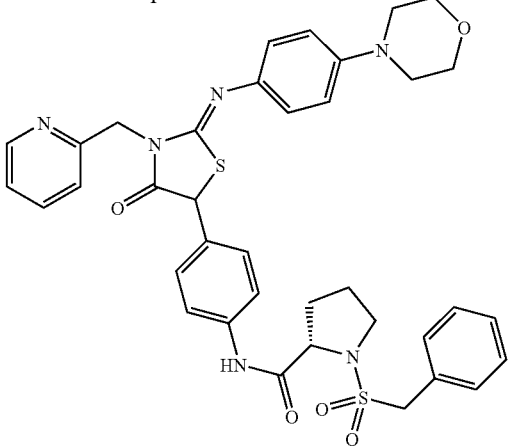

MS(ESI) m/z=711.4 (MH+); HPLC rt 1.12 min; Purity (99%).

General procedure for the formation of ureas: A 2 dram vial was charged with 1.0 ml stock solution 2S-amino-N-{4-[2-(3-fluorophenylimino)-3-furan-2yl-4-oxo-thiazolidin-5-yl]phenyl}-propionamide freebase (20 mg, 0.04 mmol), and isocyanate (0.06 mmol) was added. The reaction was shaken at 600 rpm for 18 h (additional isocyanate was added if starting amine still present). Volatile components were removed in vacuo and products purified by reverse phase preparative HPLC.

Compounds 133–136 were prepared according to the Continuation of General Synthesis Scheme 1/ureas.

Preparation of Compound 133

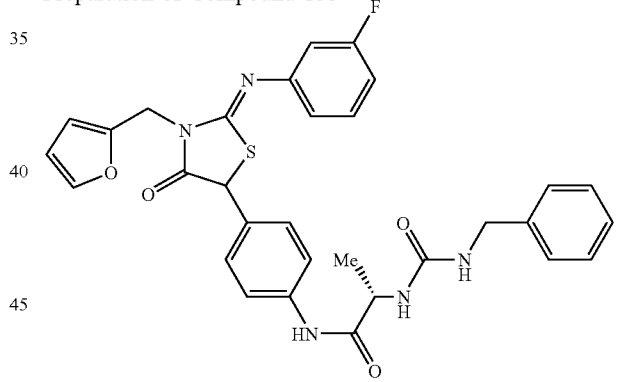

MS (ESI) m/z=586.2 (MH+); HPLC rt 1.87 min; Purity (>98%).

Preparation of Compound 134

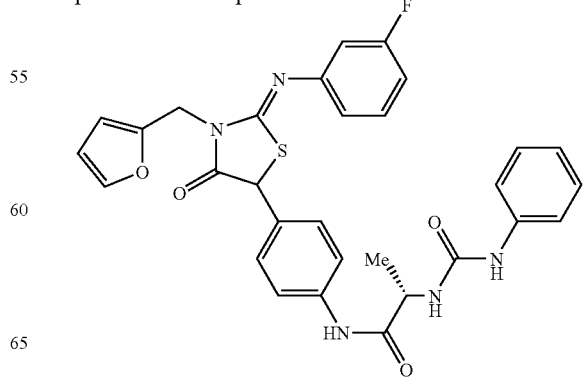

MS (ESI) m/z=572.2 (MH+); HPLC rt 1.84 min; Purity (>98%).

Preparation of Compound 135

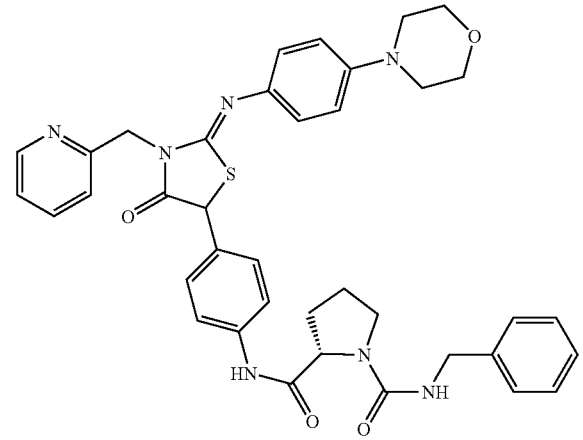

MS(ESI) m/z=690.5 (MH+); HPLC rt 1.07 min; Purity (91.5%).

Preparation of Compound 136

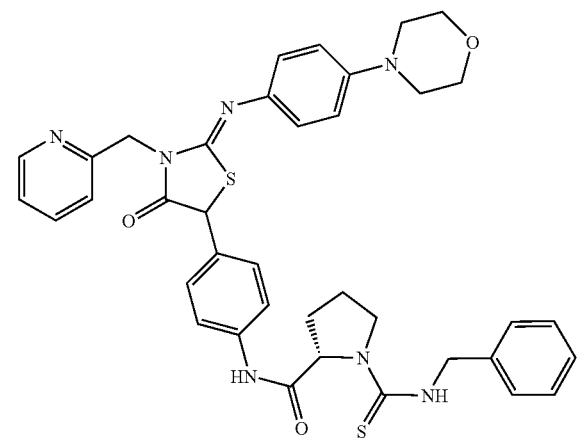

MS(ESI) m/z=706.2 (MH+); HPLC rt 1.13 min; Purity (99%).

Extention of General Synthesis to Bicyclic Analogs—General Synthesis Scheme 2

An example of bicyclic analogs wherein $R_2$ and $R_3$ of formula 1 are joined are prepared according to the following scheme. The cyclic thiourea (3,4-dihydro-1H-quinazoline-2-thione) was subjected to the synthetic procedures outlined above.

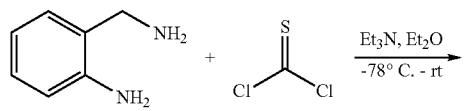

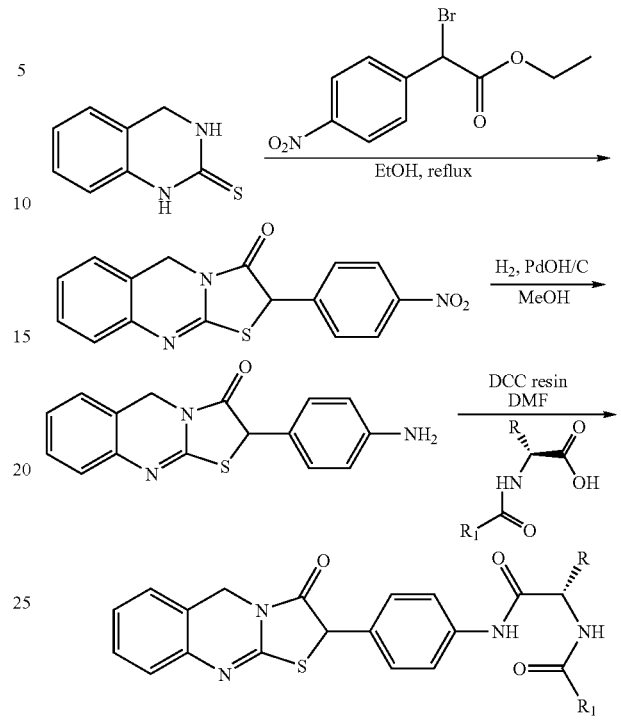

3,4-Dihydro-1H-quinazoline-2-thione

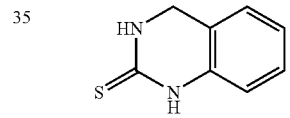

To a solution of 2-aminomethyl-phenylamine (6.35 g, 52 mmol) and triethylamine (16.8 ml, 120 mmol) in ether (150 ml) was added dropwise a solution of thiophosgene (4.6 ml, 60 mmol) in ether (40 mL), at −78° C. over 1 h. After warming to rt a precipitate was filtered, washed thoroughly with ether, dissolved in methanol (200 mL) and treated with solid KOH (6.7 g, 120 mmol). The mixture was stirred for 15 min, filtered, and the filtrate was concentrated under reduced pressure to obtain a residue which was recrystallized from methanol/water to give an off-white solid 7.43 g (87%). 1H NMR (500 MHz, DMSO-D6) δ 4.35 (s, 1H) 6.92 (d, J=7.93 Hz, 1H) 6.96 (m, 1H) 7.08 (d, J=7.32 Hz, 1H) 7.15 (m, 1H) 8.59 (s, 1H) 10.36 (s, 1H). MS (ESI) m/z 165 (MH+); HPLC (Column YMC Xterra OSD 4.6×33 mm S 7) Rt 0.81 min; Purity (96%).

2-(4-Nitrophenyl)-5H-thiazolo[2,3-b]quinazolin-3-one

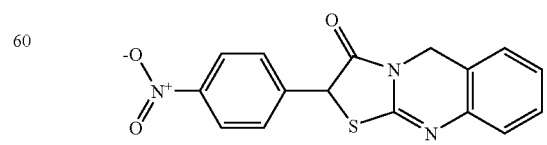

A solution of bromo-(4-nitrophenyl)acetic acid ethyl ester (0.92 g, 3.2 mmol) in ethanol (15 ml) was added to a suspension of 3,4-dihydro-1H-quinazoline-2-thione (0.5 g, 3.0 mmol) in ethanol (10 ml) and the resulting mixture was heated at reflux for 3 h. A brown solid was filtered, washed with ethanol, and dried under reduced pressure to yield 0.86 g (88%) of a yellowish solid. 1H NMR (500 MHz, DMSO-D6) δ ppm 4.89 (m, 2H) 5.95 (s, 1H) 7.12 (d, J=7.63 Hz, 1H) 7.17 (t, J=7.48 Hz, 1H) 7.26 (m, 2H) 7.82 (d, J=8.85 Hz, 2H) 8.25 (d, J=8.85 Hz, 2H). MS (ESI) m/z 326 (MH+); HPLC (Column YMC Xterra OSD 4.6×33 mm S 7) rt 1.53 min; Purity (93%).

2-(4-Aminophenyl)-5H-thiazolo[2,3-b]quinazolin-3-one

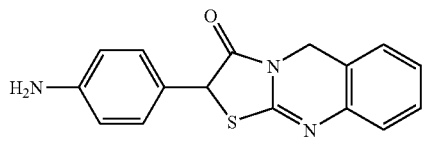

2-(4-Nitrophenyl)-5H-thiazolo[2,3-b]quinazolin-3-one (0.25 g, 0.77 mmol) was added to a suspension of 10% palladium hydroxide on carbon (50 mg) in methanol (10 ml) and the flask was flushed with N$_2$ (3×) and placed under H$_2$ (1 atm). The suspension was stirred for 3 h, filtered though a Celite plug, concentrated, and triturated with ethyl ether, filtered, to give 0.18 g (78%) of a pale yellow solid. 1H NMR (500 MHz, DMSO-D6) δ 4.88 (m, 2H) 5.75 (s, 1H) 7.10 (d, J=7.93 Hz, 1H) 7.16 (t, J=7.48 Hz, 1H) 7.25 (m, 6H) 7.54 (d, J=8.24 Hz, 2H). MS (ESI) m/z 296 (MH+): HPLC (Column YMC Xterra OSD 3.0×50 mm S 7) rt 0.96 min; Purity (92%).

General Procedure for the Coupling of Amino Acids to 2-(4-Aminophenyl)-5H-thiazolo[2,3-b]quinazolin-3-one The corresponding amino acid (0.50 to 0.70 mmol) and DCC resin (0.1 g to 0.35 g, 0.51 mmol to 0.66 mmol, 1.9 mmol/g) were mixed in DMF (7 ml) and stirred for 10 min, followed by addition of 2-(4-Aminophenyl)-5H-thiazolo[2,3-b]quinazolin-3-one (70 mg, 0.24 mmol) in DMF (2 mL). The suspension was then stirred for 24 h, filtered, and concentrated under reduced pressure. The remaining residue was then purified by preparative HPLC.

Compounds 137–139 were prepared according to General Synthesis Scheme 3 and completed according to steps 2a, 3a and 4a of General Synthesis Scheme 1.

Preparation of Compound 137

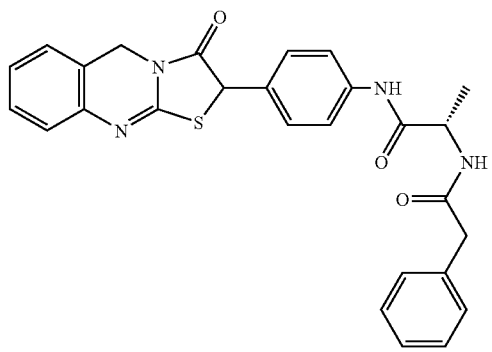

1H NMR (500 MHz, DMSO-D6) δ 1.29 (d, J=7.02 Hz, 3H) 3.49 (s, 2H) 4.41 (m, 2H) 4.87 (m, 2H) 5.65 (s, 1H) 7.09 (d, J=7.32 Hz, 1H) 7.14 (t, J=7.48 Hz, 1H) 7.22 (m, 2H) 7.27 (m, 4H) 7.40 (d, J=8.55 Hz, 2H) 7.59 (d, J=8.24 Hz, 2H) 8.41 (d, J=7.32 Hz, 1H) 10.11 (s, 1H). MS (ESI) m/z 485 (MH+). HPLC (Column YMC Xterra OSD 3.0×50 mm S 7) rt 1.52 min; Purity (95%).

Preparation of Compound 138

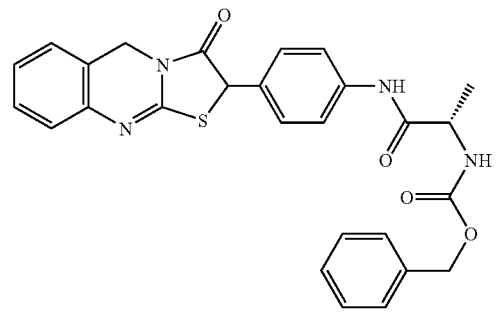

1H NMR (500 MHz, DMSO-D6) δ 1.29 (d, J=7.32 Hz, 3H) 4.19 (m, 2H) 4.88 (m, 2H) 5.03 (m, 2H) 5.66 (s, 1H) 7.09 (d, J=6.71 Hz, 1H) 7.14 (m, 1H) 7.23 (m, 2H) 7.33 (m, 5H) 7.41 (d, J=8.85 Hz, 2H) 7.61 (d, J=8.24 Hz, 2H) 10.09 (s, 1H). MS (ESI) m/z 501 (MH+); HPLC (Column YMC Xterra OSD 4.6×33 mm S 7) rt 1.58 min; Purity (94%).

Preparation of Compound 139

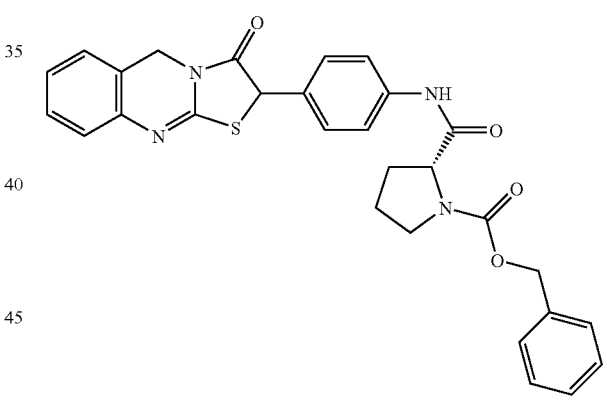

1H NMR (500 MHz, DMSO-D6) δ 1.88 (m, J=33.57 Hz, 4H) 2.22 (m, 2H) 4.35 (m, 2H) 4.90 (m, 3H) 5.07 (m, J=10.07 Hz, 2H) 5.66 (d, J=5.80 Hz, 1H) 7.12 (m, 3H) 7.21 (m, 2H) 7.37 (m, J=4.27 Hz, 2H) 7.41 (m, 2H) 7.60 (m, 2H) 10.14 (s, 1H). MS (ESI) m/z 527 (MH+); HPLC (Column YMC Xterra OSD 3.0×50 mm S 7) rt 1.61 min; Purity (96%).

Compound Activity

The compounds listed in Table below were tested for biological activity using the HCV replicon cell line and FRET assay described below. The activity ranges were classified into the following groups: A (least active)>5 μM; B 1–5 μM; C 0.1–1 μM; D (most active)<0.1 μM.

TABLE 2

COMPOUND ACTIVITY

| Compound | Replicon Inhibition Range $EC_{50}$ (μM) |
|---|---|
| 1 | C |
| 2 | A |
| 3 | D |
| 4 | D |
| 5 | D |
| 6 | D |
| 7 | D |
| 8 | C |
| 9 | |
| 10 | D |
| 11 | D |
| 12 | D |
| 13 | C |
| 14 | D |
| 15 | D |
| 16 | C |
| 17 | B |
| 18 | C |
| 19 | B |
| 20 | B |
| 21 | B |
| 22 | B |
| 23 | B |
| 24 | C |
| 25 | C |
| 26 | C |
| 27 | D |
| 28 | B |
| 29 | B |
| 30 | B |
| 31 | — |
| 32 | B |
| 33 | B |
| 34 | C |
| 35 | C |
| 36 | B |
| 37 | B |
| 38 | C |
| 39 | B |
| 40 | — |
| 41 | B |
| 42 | C |
| 43 | C |
| 44 | C |
| 45 | C |
| 46 | B |
| 47 | D |
| 48 | D |
| 49 | C |
| 50 | C |
| 51 | B |
| 52 | B |
| 53 | C |
| 54 | C |
| 55 | C |
| 56 | C |
| 57 | B |
| 58 | B |
| 59 | B |
| 60 | B |
| 61 | C |
| 62 | B |
| 63 | D |
| 64 | D |
| 65 | D |
| 66 | C |
| 67 | B |
| 68 | B |
| 69 | D |
| 70 | D |
| 71 | D |
| 72 | D |
| 72(c) | A |
| 73 | D |
| 74 | C |
| 75 | C |
| 76 | D |
| 77 | D |
| 78 | C |
| 79 | B |
| 80 | C |
| 81 | C |
| 82 | D |
| 83 | D |
| 84 | C |
| 85 | D |
| 86 | B |
| 87 | C |
| 88 | D |
| 89 | C |
| 90 | C |
| 91 | D |
| 92 | D |
| 93 | C |
| 94 | D |
| 95 | D |
| 96 | D |
| 97 | D |
| 98 | D |
| 98(c) | A |
| 99 | D |
| 100 | D |
| 101 | D |
| 102 | D |
| 103 | C |
| 104 | D |
| 105 | C |
| 106 | C |
| 107 | D |
| 108 | D |
| 109 | B |
| 110 | D |
| 111 | D |
| 112 | D |
| 113 | C |
| 114 | D |
| 115 | D |
| 116 | D |
| 117 | D |
| 118 | D |
| 119 | D |
| 120 | D |
| 121 | C |
| 122 | D |
| 123 | D |
| 124 | D |
| 125 | B |
| 126 | B |
| 127 | D |
| 128 | C |
| 129 | C |
| 130 | C |
| 131 | C |
| 132 | B |
| 133 | C |
| 134 | B |
| 135 | D |
| 136 | D |
| 137 | C |
| 138 | B |
| 139 | C |

Biological Studies

A HCV Replion assay was utilized in the present invention, and was prepared, conducted and validated as follows:

1. HCV Replicon Cell Line Preparation

The HCV replicon cell line was isolated from colonies as described by Lohman et. al. (Lohman et al., *Science* 285: 110–113 (1999), expressly incorporated by reference in its entirety) and used for all experiments. The HCV replicon has the nucleic acid sequence set forth in EMBL Accession No.: AJ242652, the coding sequence of which is from nt 1801 to 7758.

The coding sequence of the published HCV replicon was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions.

To generate cell lines, $4 \times 10^6$ Huh-7 cells (kindly provided by R. Bartenschlager and available from Health Science Research Resources Bank, Japan Health Sciences Foundation) were electroporated (GenePulser System, Bio-Rad) with 10 microgram ("μg") of RNA transcript and plated into 100-mm dishes. After 24 h, selective media containing 1.0 milligrams/milliliter ("mg/ml") G418 was added and media was changed every 3 to 5 days. Approximately 4 weeks after electroporation, small colonies were visible which were isolated and expanded for further analysis. These cell lines were maintained at 37° C., 5% $CO_2$, 100% relative humidity in DMEM (Cat# 11965-084) Gibco-BRL, Rockville, Md., with 10% heat inactivated calf serum (Sigma), 10 ml of 100× penicillin/streptomycin (Cat# 15140-122) Gibco-BRL, Rockville, Md., Geneticin (Cat# 10131-027) Gibco-BRL, Rockville, Md. at 1 mg/ml. One of the cell lines (deposited as ATCC Accession No. PTA-4583 in the American Type Culture Collection) which had approximately 3,000 copies of HCV replicon RNA/cell was used for development of the assay (HCV 1b-377-neo replicon cells).

2. FRET Assay Preparation

To perform the HCV FRET screening assay, 96-well cell culture plates were used. The FRET peptide (Anaspec, Inc., San Jose, Calif.) [Taliani et al., *Anal. Biochem.* 240:60–67 (1996), expressly incorporated by reference in its entirety] contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The assay reagent was made as follows: 5× luciferase cell culture lysis (Cat# E153A) Promega, Madison, Wis., diluted to 1× with $dH_2O$, NaCl added to 150 millimoles ("mM") final, the FRET peptide diluted to 20 micromolar ("μM") final from a 2 mM stock. Cells were trypsinized, placed into each well of a 96-well plate and allowed to attach overnight. The next day, the test compounds were added to columns 1 through 10; column 11 was media plus DMSO only, and column 12 contained a titration of interferon as a control (1000 units for A12, B12, 100 units for C12, D12, 10 units for E12, F12 and 1 unit for G12, H12). FIG. 1 shows the layout for the HTS of the replicon cells in 96-well plates. In addition, Naïve Huh-7 cells could also be used to replace wells A12 and B12 as a background control.

At various times later (typically 72 hours), 10% final volume Alamar blue (Cat# 00-100) Trek Diagnostics, Cleveland, Ohio was added per well. The plates were returned to the incubator for 5 hours and then read in the Cytoflour (PE Biosystems) to determine Alamar blue conversion in each well as a measure of cellular toxicity. After reading the Alamar blue fluorescence following the manufacturers directions, plates were rinsed 2× with PBS and then used for FRET assay by the addition of 30 ul of the FRET peptide assay reagent (described above) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold.

Compound analysis depended upon the quantification of the relative HCV replicon inhibition and the relative cytotoxicity values. To calculate cytotoxicity values, the average alamar blue fluorescence signals from the control wells in row 11 were set as 100% non-toxic. The individual signals in each of the compound test wells were then divided by the average control signal and multiplied by 100% to determine percent cytotoxicity. To calculate the HCV replicon inhibition values, an average background value FRET signal was obtained from the two wells containing the highest amount of interferon at the end of the assay period. These numbers were similar to those obtained from naïve Huh-7 cells (results not shown). The background numbers were then subtracted from the average FRET signal obtained from the control wells in row 11 and this number was used as 100% activity. The individual signals in each of the compound test wells were then divided by the averaged control values after background subtraction and multiplied by 100% to determine percent activity. $EC_{50}$ values for an interferon titration were calculated as the concentration which caused a 50% reduction in FRET activity. The two numbers generated for the compound plate, percent cytoxicity and percent activity, were used to determine compounds of interest for further analysis.

The assay was further adapted to accommodate titrations of compounds to determine $EC_{50}$ and $CC_{50}$ values. Briefly the plates were set-up with controls as before in column 11 and 12, but the first 10 columns were used for titration of compounds in duplicate starting at the highest concentration in row A to the most dilute in row H. The amount of compound which yielded a 50% reduction in HCV FRET activity determined the $EC_{50}$ while the amount which caused a 50% reduction in Alamar blue conversion was used for $CC_{50}$.

$EC_{50}$ values were confirmed by HCV RNA detection using RT-PCR, according to the manufacturer's instructions, with a Platinum Quantitative RT-PCR Thermoscript One-Step Kit (Cat# 11731-015) on a Perkin-Elmer ABI Prism Model 7700 sequence detector. The primers for TaqMan were selected for use following analysis of RNA sequences with Primer Express Software from ABI. Primers used for detection of the plus strand RNA were 131F-5' GGGAGAGCCATAGTGGTCTGC 3' (SEQ ID NO:1) and 231R-5'CCCAAATCTCCAGGCATTGA 3' (SEQ ID NO:2) which amplify the HCV 5'UTR from nucleotides 131 to 231. The probe used for detection, 5'FAM-CGGAATTGCCAG-GACGACCGG-BHQ1 3' (SEQ ID NO:3) was obtained from Biosearch Technologies, Novato, Calif. RNA's were purified from 96-wells using the RNAeasy 96 kit (Cat# 74181) Qiagen, Valencia, Calif.

$EC_{50}$ values were also determined by Western analysis performed according to the instructions for Chemiluminescence Immunology Kit (Cat# NEL105) Amersham, Arlington Heights, Ill. using a Molecular Dynamics Storm 860 phosphoimager and associated software. Experiments were done in duplicate. The primary and secondary antibody dilutions were at 1 to 5,000. Antisera was generated by immunizing rabbits with purified NS3 protease made from an *E. Coli* expression vector encoding the first 181 amino acids of HCV 1a NS3 with subsequent boosts. Bleeds were tested weekly and boosts continued until a positive signal on a control western was seen. Secondary antibody was a BioRad (#170-6515) Goat anti-Rabbit IgG HRP Conjugate (Cat# 170-6515) BioRad, Hercules, Calif. The protein samples for western analysis were from the same wells used for the FRET assay and were prepared by the addition of an equal volume of 2×SDS-PAGE buffer to the FRET assay mixture, heating and loading on a 10% gel for SDS-PAGE. Interferon alpha (Cat# I-4276) Sigma, St. Louis, Mo. (IFN-α) was obtained and stored as recommended.

Results of Western, FRET and RT-PCR assays indicate $EC_{50}$ values (in units of IFN-α per milliliter) of 1.9 for the Western, 2.9 for the FRET and 5.3 for RT-PCR. These values are within 3-fold of one another and indicate equivalency between the assay methods. This demonstrates the utility of the FRET assay method for inhibitor titration and provides a comparison of a HTS format to the standard qRT-PCR method of HCV quantification.

tested. In the initial test, approximately 60-fold resistance, judged by the FRET assay, was observed between wt replicon cells and selected replicon cells (designated as Compound 1-r replicon cells).

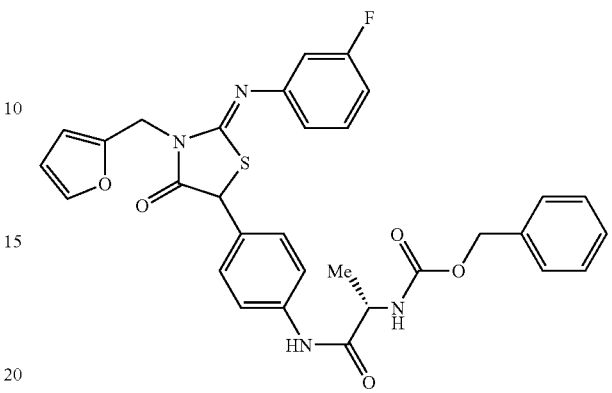

Compound I

Target Mapping

Materials and Methods cDNA cloning. To generate Compound 1 resistant cDNA, total RNA was isolated from Compound 1-r replicon cells using Trizol (Cat# 15596-026) Gibco-BRL, Rockville, Md. and precipitated with isopropanol. As a control, RNA was

TABLE 3

Diagram of 96-well plate layout for HCV replicon HTS

| | 1 | 2 | 3 | 4 | 5 | 6 | 7 | 8 | 9 | 10 | 11 | 12 |
|---|---|---|---|---|---|---|---|---|---|---|---|---|
| A | Screen | Screen | Screen | Screen | Screen | Screen | Screen | Screen | Screen | Screen | 1-HCV | Inhibited |
| B | Screen | Screen | Screen | Screen | Screen | Screen | Screen | Screen | Screen | Screen | 1-HCV | Inhibited |
| C | Screen | Screen | Screen | Screen | Screen | Screen | Screen | Screen | Screen | Screen | 1-HCV | Titration |
| D | Screen | Screen | Screen | Screen | Screen | Screen | Screen | Screen | Screen | Screen | 1-HCV | Titration |
| E | Screen | Screen | Screen | Screen | Screen | Screen | Screen | Screen | Screen | Screen | 1-HCV | Titration |
| F | Screen | Screen | Screen | Screen | Screen | Screen | Screen | Screen | Screen | Screen | 1-HCV | Titration |
| G | Screen | Screen | Screen | Screen | Screen | Screen | Screen | Screen | Screen | Screen | 1-HCV | Titration |
| H | Screen | Screen | Screen | Screen | Screen | Screen | Screen | Screen | Screen | Screen | 1-HCV | Titration |

In Table 3, "Screen" indicates wells with test compound, 1-HCV denotes control replicon wells (100% activity), "Inhibited" contains the highest amount of a control inhibitor (100% inhibited) and is used to determine background on each plate, titration indicates the titration of interferon and is used as a sensitivity control. Units of interferon from the top of row 12 in duplicate are 1000, 100, 10, and 1.

Isolation of Resistant Replicons:

HCV 377-neo replicon cells were plated in 100-mm plates with ~25% confluence after 24 hr seeding. Compound 1 was added at the final concentrations of 5, 10 and 20 μM in the presence of G418. Wild type replicon cells in the absence of the compound were used as a control. After 5–6 weeks, both wt replicon cells and selected cells were tested for their sensitivity to Compound 1. In addition, cell lines derived from individual colonies from different concentrations of selective Compound 1 were also isolated, expanded and isolated in parallel from wild-type replicon cells. The entire HCV ORF was generated and amplified in a single fragment using the SuperScript One-Step RT-PCR for Long Templates (Cat# 11922-028) Gibco-BRL, Rockville, Md. and primers BR735-5'TGAATGTCGTGAAGGAAGCAG3' and 3'Xba-5'TGGCAGTCTAGAAGTACTTGATCTGCAGAGAGG3'. Reaction products were gel purified and cloned directly into pCR2.1-TOPO using a TOPO TA cloning kit (Cat# 45-0641) Invitrogen, Carlsbad, Calif. The DNA sequence of the entire HCV nonstructural coding region was determined for multiple clones.

Plasmid construction. To put the Y2065H and Y2065C substitutions into the HCV 1b 377-neo replicon, cDNAs containing these changes were digested with EcoRI and HpaI, the correct size fragments were gel purified, and ligated into similarly digested HCV 1b-377-neo DNA. Clones containing the correct sequence were identified by restriction digestion and confirmed by sequence analysis. To move the Y2065H and Y2065C substitutions into the Blast/Luciferase replicon, a subregion of the 377-neo replicon containing these mutations was isolated by digestion with EcoRI and HindIII and ligated into similarly digested Blast/Luciferase replicon DNA. Clones containing the correct sequence were identified by restriction digestion and confirmed by sequence analysis.

Transient replication assays and generation of cell lines. Plasmid DNAs were linearized with ScaI, extracted two times with phenol, two times with chloroform, and precipitated with ethanol. DNA pellets were washed with 80% ethanol and resuspended in 10 mM tris-HCl and 1 mM EDTA. RNA transcripts were synthesized in vitro using the T7 MegaScript transcription kit (Ambion) according to manufacturer's directions. For transient replication assays, subconfluent cured Huh-7 cells in a 100-mm dish were transfected with 5 µg of RNA transcript using DMRIE-C (Cat# 10459-014) Gibco-BRL, Rockville, Md. according to manufacturers directions. Four hours later cells were trypsinized, and aliquots were plated into 6 well plates in the presence or absence of compound. At the time points given, cells were harvested and luciferase activity was determined using the Renilla Luciferase Assay kit (Cat# E2820) Promega, Madison, Wis. according to manufacturer's directions. To generate cell lines, $4 \times 10^6$ cured Huh-7 cells were electroporated with 10 µg of RNA transcript and plated into 100-mm dishes. After 24 h, selective media containing 0.3 mg/ml G418 was added and media was changed every 3 to 5 days. Approximately 3 weeks after electroporation, small colonies were visible which were isolated and expanded for further analysis.

Results

Mapping of Compound 1 resistance. To determine the target gene of Compound 1, sequencing was performed on the HCV nonstructural proteins NS3-NS5B from the resistant cells. Eight different cDNA clones were generated from 3 independently isolated resistant cell lines (cell lines B, C and D, all derived from 5 uM selection) and one from a wild-type cell line. All three clones from cell line B had a T-to-C substitution at nt 4943, resulting in an amino acid substitution of Tyr2065-to-His in NS5A. Likewise, all 4 clones from cell line C had an A-to-G substitution at nt 4944, resulting in an amino acid substitution of Tyr2065-to-Cys. The one clone from cell line D had the wild-type sequence at both of these nucleotide positions as did the clones generated from the wild-type cell line. Although cell line D was resistant to Compound 1, finding the wild-type sequence in the one clone examined suggests that it is a heterogeneous population.

To determine if the Y2065H change was necessary and sufficient to confer resistance to Compound 1, the single mutation was generated in the HCV 377-neo replicon. RNA transcripts of this clone, in parallel with the wild-type replicon clone, were transfected into Huh-7 cells and colony formation was examined after 3 weeks of G418-selection in the presence or absence of 2 µM Compound 1. As shown in Table 4, cells transfected with the wild-type replicon RNA had a 95% reduction in colony number in the presence of Compound 1. In contrast, similar numbers of colonies were observed for the Y2065H clone regardless of whether or not Compound 1 was present, suggesting the substitution conferred resistance to this compound. To further verify this, colonies formed in the absence of Compound 1 were isolated and expanded for both the wild-type and Y2065H clones. Sensitivity of these cells to Compound 1 was then examined using the FRET assay. On the wild-type cells, Compound 1 had an $EC_{50}$ of 1.5 µM (Table 5) while the Y2065H cell line showed no inhibition up to 5 µM, the highest concentration tested. Further testing with Compound 124, a more potent and soluble derivative of Compound 1, showed there was more than a 50-fold window of resistance in the Y2065H cells as compared to wild-type cells.

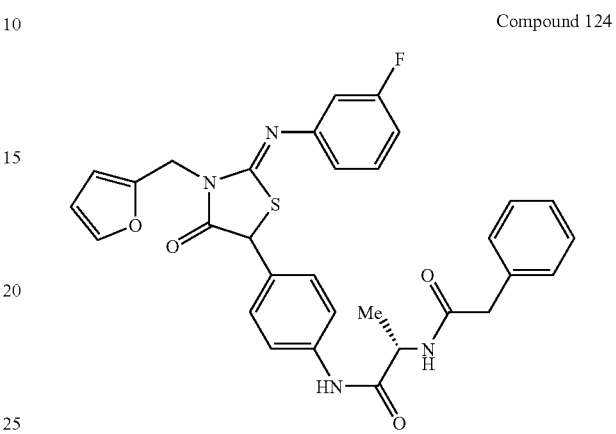

Compound 124

We next used a transient reporter system to look at resistance in a first-cycle analysis. The Y2065H and Y2065C mutations were made in a replicon that contains a blasticidin/luciferase fusion gene in place of the neomycin gene. Cells were transfected with RNA transcripts of the wild-type replicon, or the replicon containing either Y2065H or Y2065C, and incubated in the presence or absence of 0.5 µM Compound 124. Incubation with 1 µM of a HCV protease inhibitor, was included as a control. Transfected cells were harvested at 4, 48 and 72 h and cell lysates examined for luciferase activity. As shown in Table 6, all three replicons replicated in the absence of compound, although the replication efficiency of the wild-type replicon was about 4 times higher than that of the mutants. However, in the presence of Compound 124, replication of the wild-type replicon was completely inhibited, while the Y2065H and Y2065C replicons displayed only a 10–15% decrease in replication. As expected, replication of all three replicons was completely blocked in the presence of the HCV protease inhibitor. Taken together, these data demonstrate that the Y2065H/C mutation in NS5A is sufficient and necessary to confer resistance to the Compound 1 chemotype. Thus, the compounds of the invention can be effective to inhibit the function of the HCV NS5A protein. Further, the compounds of the invention can be effective against the HCV 1b genotype.

Combination Studies.

Since clinical drug resistance often develops in viral infections following single-agent therapies, there is a need to assess the additive, antagonistic, or synergistic properties of combination therapies. We used the HCV replicon system to assess the potential use of our NS5A inhibitor in combination therapies with Intron A and inhibitors targeting other HCV proteins. Three HCV antivirals, a protease inhibitor, replicase inhibitors (cmpd 2006 of WO 03/010141, and des fluoro analog of example 289 of EP 1162196A) as well as Intron A, were tested in combination with Compound 81 herein, an inhibitor of HCV NS5A. Drugs were tested at eleven concentrations each, diluted in DMSO by 3-fold dilutions. The highest concentration used for the four HCV inhibitors was 20 µM while the highest concentration for Intron A was 5,000 IU/ml. The drugs were tested as monotherapies and in combination with compound 81 at various concentration ratios. Cells were exposed to compounds for 72 h and the amount of HCV inhibition was then determined using the FRET assay. The potential cytotoxicities of these combined agents were also analyzed in parallel by Alamar blue staining. The degree of antagonism or synergy were determined over a range of drug concentrations, and the combination response curves were fit to assess the antiviral effects of the drug treatment combinations. The concentration ratios were analyzed using the method of Chou. Table 7 reports the combination indices (CI) and the asymptotic confidence intervals at the different concentration ratios. All combination indices were tested for departure from additivity using isobologram methods. In general, CIs near 1 indicate additive effects, while values less than 1 or much greater than 1 suggest synergy or antagonism, respectively.

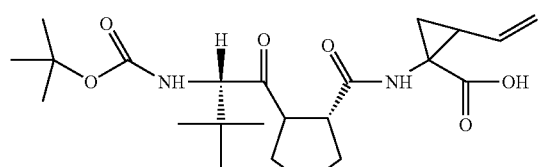

Protease Inhibitor

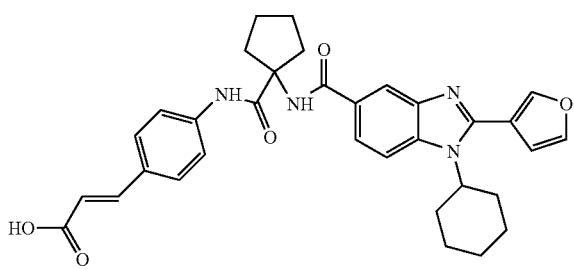

Replicase Inhibitor
cmpd 2006 of WO 03/010141

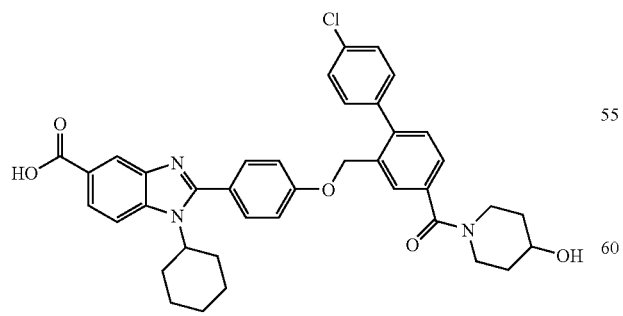

Replicase Inhibitor
des fluoro analog of example 289
of EP 1162196A

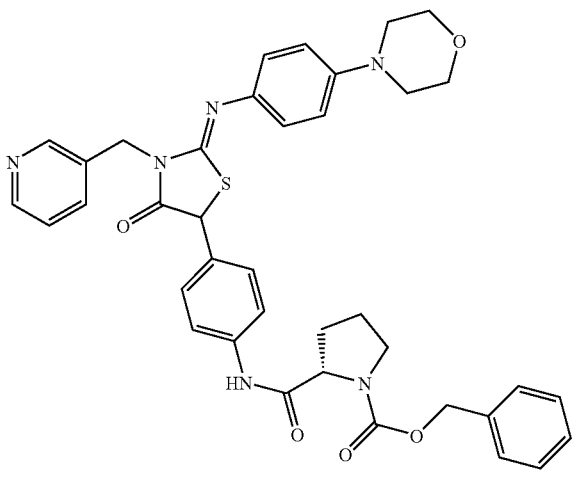

Compound 81
NS5A Inhibitor

The EC50s of these drugs in monotherapy are 9–11 nM Compound 81, 307 nM for protease inhibitor, 4.3 µM for compound 2006, 0.9 µM for des fluoro of example 289 and 9 U/ml for Intron A, in agreement with published values. Combining the protease inhibitor, with Compound 81 yielded an additive response and a CI near 1 with each drug ratio at both the 50 and 75% effective levels (Table 4). Likewise, the polymerase inhibitors (2006 and 289) in combination with Compound 81 also showed additivity at both the 50 and 75% effective levels (Table 7). Importantly, no significant drug antagonism was observed when Compound 81 was combined with any of the three HCV inhibitors. When Compound 81 was combined with Intron A, The CIs were significantly below one at all three ratios tested at both the 50 and 75% effective levels, suggesting a synergistic response (Table 7).

These results demonstrate that combination treatment of replicon cells with HCV NS5A inhibitors and either Intron A, or inhibitors targeting the HCV protease or polymerase, yields additive to synergistic antiviral effects. The ability to use these NS5A inhibitors in combination therapy can provide major advantages over single drug therapy for the treatment of HCV.

TABLE 4

Colony formation in the presence and absence of Compound 1.

| | Number of colonies | |
|---|---|---|
| RNA transfected | No compound | 2 µM Compound 1 |
| Wild-type | 60 | 3 |
| Y > H | 15 | 10 |

TABLE 5

Compound testing on wild-type and Y > H replicon cells.

| Cell Line | Compound 1 | | Compound 124 | |
|---|---|---|---|---|
| | $EC_{50}$ μM | $CC_{50}$ μM | $EC_{50}$ μM | $CC_{50}$ μM |
| Wild-type | 1.5 | >5 | 0.103 | >5 |
| Y > H | >5 | >5 | >5 | >5 |

TABLE 6

Compound testing on wt and mutant replicon RNAs

| Clone | compound | rlu* 48 h | rlu 72 h |
|---|---|---|---|
| wt | none | 14030 | 41770 |
| wt | PI** | 2977 | 2855 |
| wt | 124*** | 3237 | 3184 |
| Y > H | none | 8369 | 12612 |
| Y > H | PI | 3272 | 2616 |
| Y > H | 124 | 7505 | 11257 |
| Y > C | none | 6973 | 11797 |
| Y > C | PI | 4403 | 3294 |
| Y > C | 124 | 7186 | 9696 |

*rlu-relative light units
**1 μM PI
***0.5 μM 124

TABLE 7

Two Drug Combinations
Table 3. Two-drug combinations

| Drug combined with Compound 81 | Molar ratio* | CI at HCV inhibition of: | | Overall Result |
|---|---|---|---|---|
| | | 50% | 75% | |
| Protease Inhibitor | 1:1 | 1.09 +/− 0.14 | 1.13 +/− 0.22 | Additive |
| | 2.5:1 | 1.05 +/− 0.13 | 1.12 +/− 0.22 | Additive |
| | 1:2.5 | 0.94 +/− 0.09 | 0.91 +/− 0.11 | Additive |
| Compound 2006 | 1:1 | 1.18 +/− 0.2 | 1.2 +/− 0.32 | Additive |
| | 2.5:1 | 1.0 +/− 0.18 | 1.12 +/− 0.28 | Additive |
| | 1:2.5 | 1.1 +/− 0.17 | 1.21 +/− 0.26 | Additive |
| Example 289 des fluoro | 1:1 | 1.04 +/− 0.11 | 0.95 +/− 0.15 | Additive |
| | 2.5:1 | 1.08 +/− 0.13 | 0.97 +/− 0.17 | Additive |
| Intron A | 1:1 | 0.62 +/− 0.08 | 0.55 +/− 0.09 | Synergistic |
| | 2.5:1 | 0.65 +/− 0.08 | 0.51 +/− 0.07 | Synergistic |
| | 1:2.5 | 0.7 +/− 0.07 | 0.55 +/− 0.08 | Synergistic |

*The first number represents Compound 81

Although the invention has been described with respect to specific aspects, those skilled in the art will recognize that other aspects are to be included within the scope of the claims that follow.

---

What is claimed is:

1. A compound of formula I

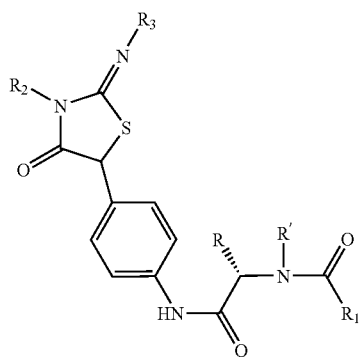

wherein R is $C_{1-4}$ alkyl, optionally substituted with 1–3 halogen atoms, 1–3 oxygen atoms or 1–3 nitrogen atoms, said R having an S stereoconfiguration; R' is H or a bond wherein R and R' are joined to form a cyclic structure;

$R_1$ is a member selected from the group consisting of $C_{1-6}$ alkyl, $C_{3-7}$ cycloalkyl, $C_{6-10}$ aryl, $C_{1-6}$ alkoxy, $C_{6-10}$ aryloxy, $C_{6-10}$ aryl ($C_{1-6}$) alkyl, $C_{6-10}$ aryl ($C_{1-6}$) alkoxy, aryl-substituted $C_{1-6}$ alkyl ($C_{6-10}$) aryl and Het; and $R_2$ and $R_3$ are each independently selected from the group consisting of $C_{1-6}$ alkyl, $C_{3-7}$ cycloalkyl, $C_{6-10}$ aryl, $C_{1-6}$ alkoxy, $C_{6-10}$ aryloxy, Het, $C_{6-10}$ aryl ($C_{1-6}$) alkyl, $C_{6-10}$ aryl ($C_{1-6}$) alkoxy, acyl ($C_{1-6}$) alkoxy, with the proviso that one of $R_2$ or $R_3$ can be a bond and $R_2$ and $R_3$ are joined to form a cyclic structure;

or pharmaceutically acceptable enantiomer, diastereomer, solvate, prodrug or salt thereof.

2. The compound according to claim 1 wherein R is methyl.

3. The compound according to claim 1 wherein R is selected from propyl forming a cyclic structure with R', or propionyl forming a cyclic structure with R'.

4. The compound according to claim 1 wherein $R_1$ is selected from the group consisting of $C_{6-10}$ aryl ($C_{1-6}$) alkyl, $C_{6-10}$ aryl ($C_{1-6}$) alkoxy and a 5–7 membered monocylic heterocycle.

5. The compound according to the claim 4 wherein $R_1$ is selected from the group consisting of $C_6$ aryl ($C_{1-3}$) alkyl and $C_6$ aryl ($C_{1-3}$) alkoxy.

6. The compound according to claim 1 wherein $R_2$ and $R_3$ are each independently selected from the group consisting of $C_{6-10}$ aryl, 5–7 membered monocyclic heterocycle, $C_{1-3}$ alkyl substituted with a 5–7 membered heterocycle, $C_{6-10}$ aryl substituted with a 5–7 membered heterocycle, and a 7–12 membered bicyclic heterocycle.

7. The compound according to claim 6 wherein $R_2$ and $R_3$ are each independently selected from a $C_{1-3}$ alkyl substituted with a 5–7 membered heterocycle and a halogenated 5–7 membered heterocycle.

8. The compound according to claim 1 wherein $R_1$ is selected from the group consisting of:

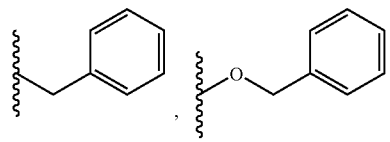

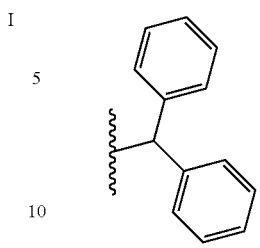

$R_2$ is selected from the group consisting of:

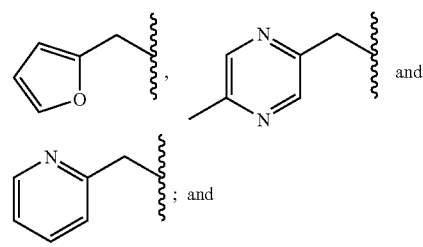

$R_3$ is selected from the group consisting of:

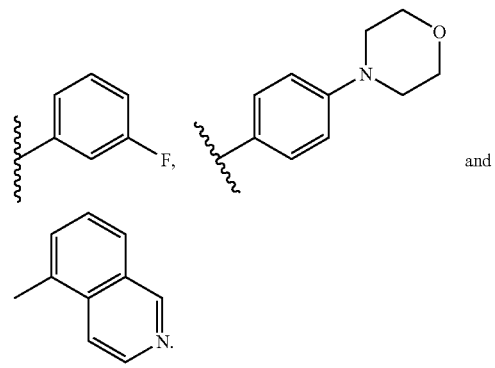

9. The compound according to claim 1 selected from the group consisting of:

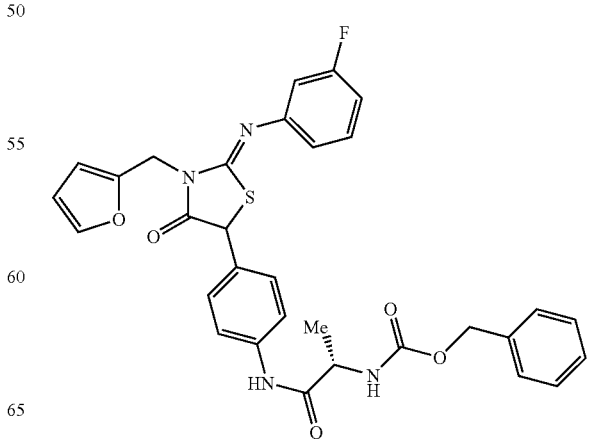

A

B
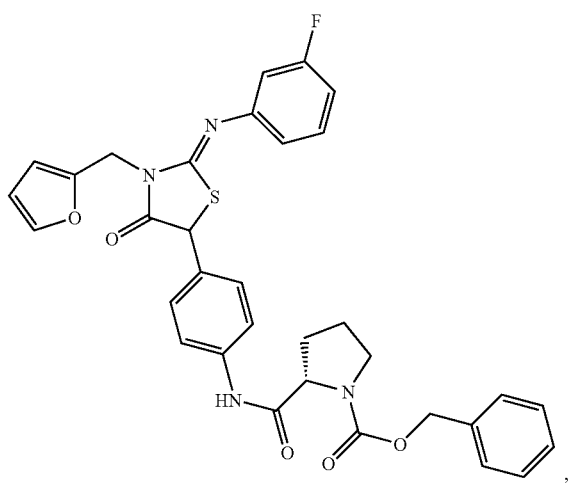
,
C
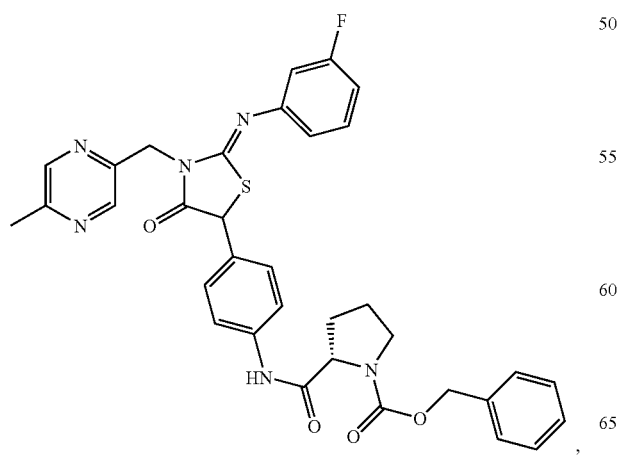
,
D
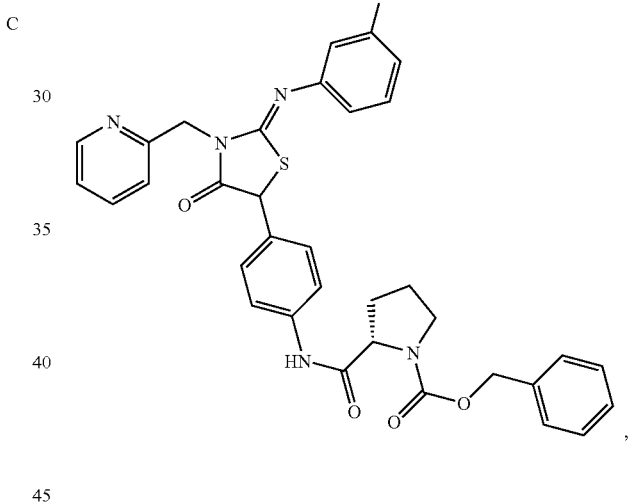
,
E
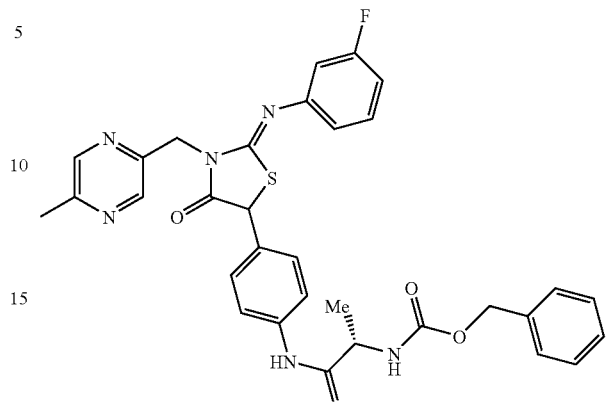
,
F
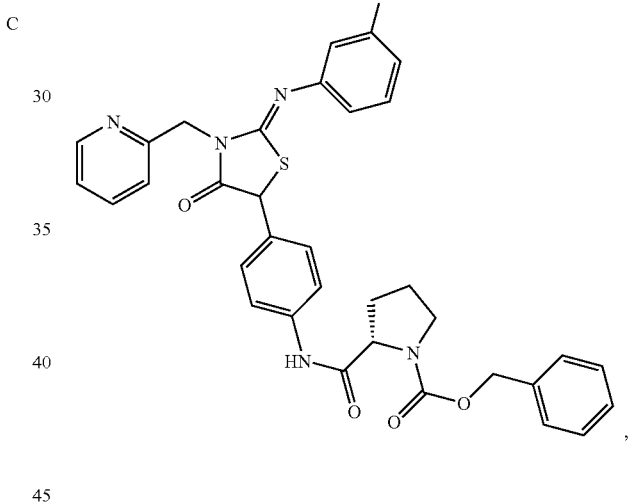
,
G
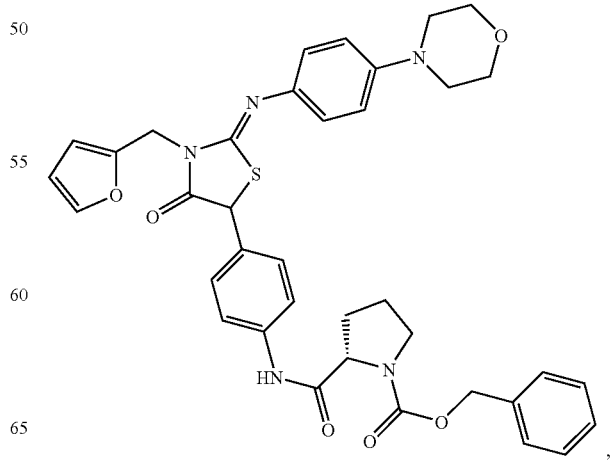
, H
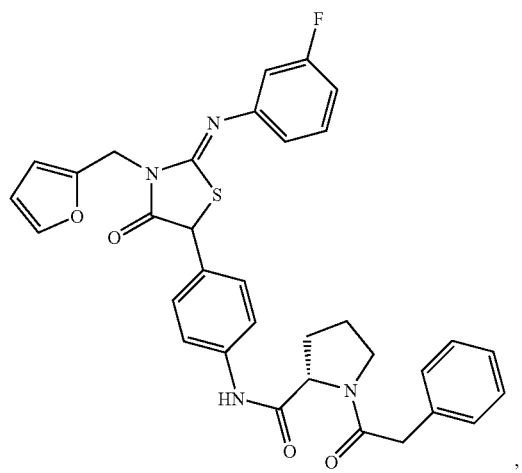
,
K
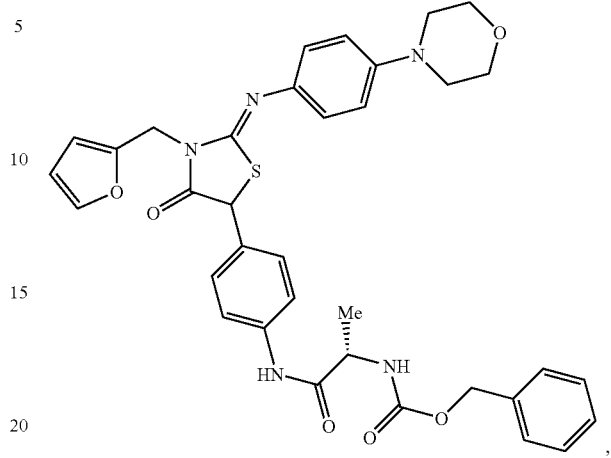
,
I
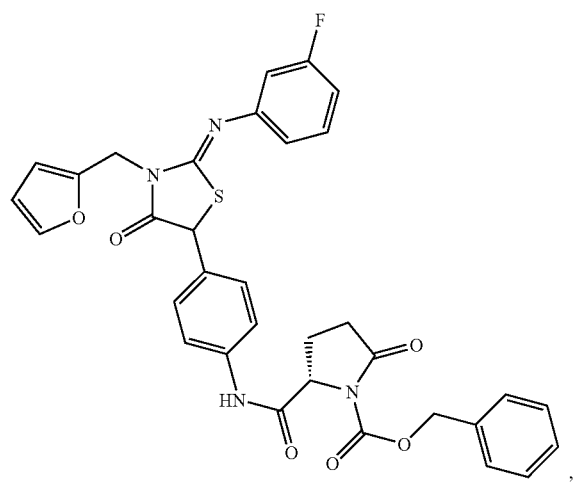
,
L
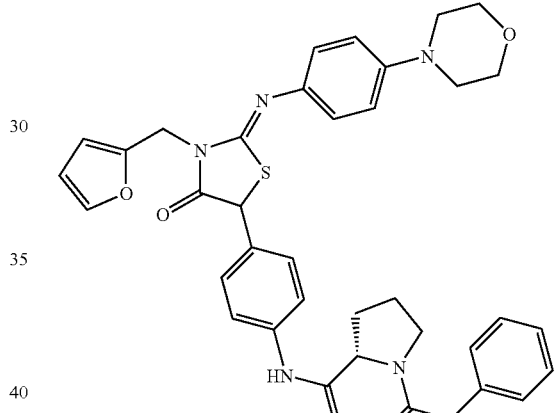
and
J
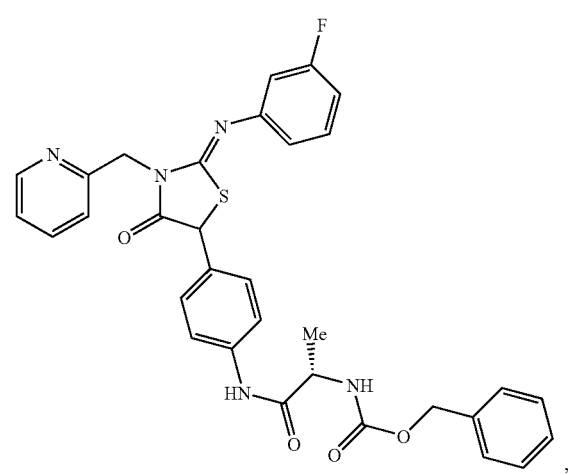
,
M
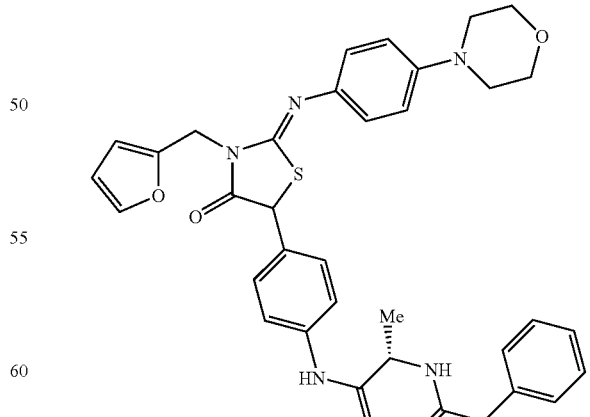
or pharmaceutically acceptable enantiamer, distereomer, solvate, prodrug or salt thereof.

10. A compound of formula II

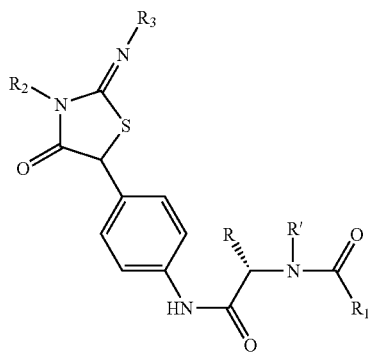

wherein R is $C_{1-4}$ alkyl, having an S stereoconfiguration;
R' is or a bond wherein R and R' are joined to form a cyclic structure;
$R_1$ is a member selected from the group consisting of $C_{6-10}$ aryl ($C_{1-6}$) alkyl, $C_{6-10}$ aryl ($C_{1-6}$) alkoxy and Het; and
$R_2$ and $R_3$ are each independently selected from the group consisting of $C_{6-10}$ aryl, 5–7 membered monocyclic heterocycle, $C_{1-3}$ alkyl substituted with a 5–7 membered heterocycle, $C_{6-10}$ aryl substituted with a 5–7 membered heterocycle, and a 7–12 membered bicyclic heterocycle.
or pharmaceutically acceptable enantiomer, diastereomer, solvate, prodrug or salt thereof.

11. The compound according to claim 10 wherein R is methyl.

12. The compound according to claim 11 wherein R is propyl forming a cyclic structure with R'.

13. The compound according to claim 10 wherein $R_1$ is selected from the group consisting of $C_6$ aryl ($C_{1-3}$) alkyl and $C_6$ aryl ($C_{1-3}$) alkoxy.

14. The compound according to claim 13 wherein $R_1$ is benzyl.

15. The compound according to claim 10 wherein $R_2$ is a 5–6 membered monocyclic heterocycle.

16. The compound according to claim 15 wherein $R_2$ is selected from the group consisting of:

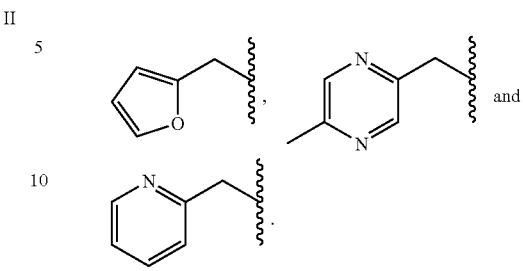

17. The compound according to claim 10 wherein $R_3$ is selected from the group consisting of a 5–6 membered monocyclic heterocycle, $C_{6-10}$ aryl substituted with a 5–7 membered heterocycle and a 7–12 membered bicyclic heterocycle.

18. The compound according to claim 17 wherein $R_3$ is selected from the group consisting of:

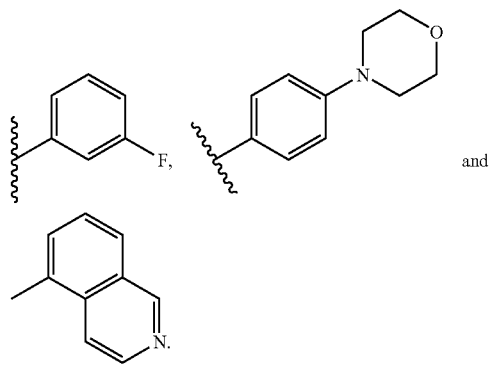

19. A composition comprising the compound of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,183,302 B2 |
| APPLICATION NO. | : 10/637099 |
| DATED | : February 27, 2007 |
| INVENTOR(S) | : Jeffrey Lee Romine et al. |

Page 1 of 1

It is certified that error appears in the above-identified patent and that said Letters Patent is hereby corrected as shown below:

Column 11, lines 24-45; claim 9, column 97, lines 25-45, structure C should appear as follows:

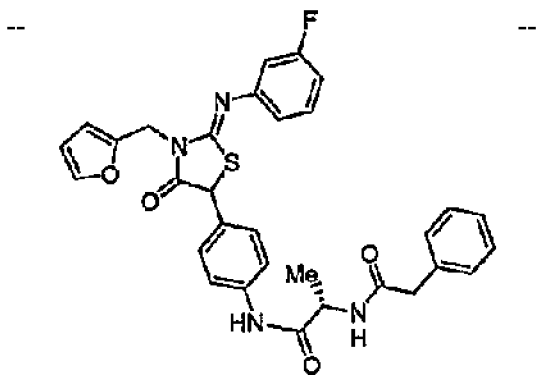

Claim 9, column 100, line 66, "distereomer" should be --diastereomer--.

Claim 10, column 101, line 20, "R' is or a bond" should be --R' is H or a bond--.

Claim 10, column 101, line 30, "heterocycle." should be --heterocycle;--.

Signed and Sealed this

Twenty-second Day of May, 2007

JON W. DUDAS
*Director of the United States Patent and Trademark Office*

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: 5' Cloning Primer

<400> SEQUENCE: 1
gggagagcca tagtggtctg c    21

<210> SEQ ID NO 2
<211> LENGTH: 20
<212> TYPE: DNA
<213> ORGANISM: Artificial Sequence
<220> FEATURE:
<223> OTHER INFORMATION: 5' Cloning Primer

<400> SEQUENCE: 2
cccaaatctc caggcattga    20

<210> SEQ ID NO 3
<211> LENGTH: 21
<212> TYPE: DNA
<213> ORGANISM: Artificial Sequence
<220> FEATURE:
<223> OTHER INFORMATION: 5' FAM Cloning Primer

<400> SEQUENCE: 3
cggaattgcc aggacgaccg g    21